US012715847B2

(12) United States Patent
Teng et al.

(10) Patent No.: US 12,715,847 B2
(45) Date of Patent: Aug. 25, 2026

(54) ANTIBACTERIAL COMPOUNDS

(71) Applicant: Blacksmith Medicines, Inc., San Diego, CA (US)

(72) Inventors: Min Teng, San Diego, CA (US); Baskar Nammalwar, San Diego, CA (US); Xiaoming Li, San Diego, CA (US); Christian Perez, San Diego, CA (US); David T. Puerta, San Diego, CA (US)

(73) Assignee: BLACKSMITH MEDICINES, INC., San Diego, CA (US)

( * ) Notice: Subject to any disclaimer, the term of this patent is extended or adjusted under 35 U.S.C. 154(b) by 399 days.

(21) Appl. No.: 18/264,838

(22) PCT Filed: Feb. 8, 2022

(86) PCT No.: PCT/US2022/015682
§ 371 (c)(1),
(2) Date: Aug. 9, 2023

(87) PCT Pub. No.: WO2022/173758
PCT Pub. Date: Aug. 18, 2022

(65) Prior Publication Data

US 2024/0166609 A1 May 23, 2024

Related U.S. Application Data

(60) Provisional application No. 63/148,261, filed on Feb. 11, 2021.

(51) Int. Cl.
*C07D 233/64* (2006.01)
*A61P 31/04* (2006.01)

(52) U.S. Cl.
CPC ............ *C07D 233/64* (2013.01); *A61P 31/04* (2018.01)

(58) Field of Classification Search
CPC .. C07D 233/64; C07D 403/12; C07D 405/12; C07D 413/12; A61P 31/04; A61P 11/00; A61K 9/4866
See application file for complete search history.

(56) References Cited

U.S. PATENT DOCUMENTS

| | | | |
|---|---|---|---|
| 2017/0088525 | A1 | 3/2017 | Fu et al. |
| 2021/0221796 | A1 | 7/2021 | Teng et al. |
| 2021/0309651 | A1 | 10/2021 | Teng et al. |
| 2022/0002279 | A1 | 1/2022 | Takashima et al. |
| 2024/0150298 | A1 | 5/2024 | Teng et al. |
| 2026/0049092 | A1 | 2/2026 | Lonergan et al. |

FOREIGN PATENT DOCUMENTS

| | | | |
|---|---|---|---|
| JP | 2013100277 | A | 5/2013 |
| WO | WO-2008027466 | A1 | 3/2008 |
| WO | WO-2015024021 | A2 | 2/2015 |
| WO | WO-2015085238 | A1 | 6/2015 |
| WO | WO-2017083434 | A1 | 5/2017 |
| WO | WO-2018208985 | A2 | 11/2018 |
| WO | WO-2018208987 | A2 | 11/2018 |
| WO | WO-2018216822 | A1 | 11/2018 |
| WO | WO-2020061375 | A1 | 3/2020 |
| WO | WO-2020102572 | A1 | 5/2020 |
| WO | WO-2020105660 | A1 | 5/2020 |
| WO | WO-2021195260 | A1 | 9/2021 |
| WO | WO-2022173756 | A1 | 8/2022 |
| WO | WO-2022173758 | A1 | 8/2022 |
| WO | WO-2024036170 | A1 | 2/2024 |
| WO | WO-2024036176 | A1 | 2/2024 |
| WO | WO-2025174868 | A1 | 8/2025 |
| WO | WO-2025174875 | A1 | 8/2025 |

OTHER PUBLICATIONS

PCT/US2023/071868 International Search Report and Written Opinion dated Oct. 6, 2023.
PCT/US2025/015571 International Search Report and Written Opinion dated Apr. 1, 2025.
PCT/US2025/015580 International Search Report and Written Opinion dated Apr. 1, 2025.
Yamada, Yousuke. et al. Fragment-Based Discovery of Novel Non-Hydroxamate LpxC Inhibitors with Antibacterial Activity. Journal of medicinal chemistry 63(23):14805-14820 (2020).
Berge et al. Pharmaceutical Salts. Journal of Pharmaceutical Sciences 66(1):1-19 (Jan. 1977).
Bundgaard. Chapter 5: Design and Application of Prodrugs. A Textbook of Drug Design and Development. (pp. 113-191) (1991).
Bundgaard. Means to Enhance Penetration: Prodrugs as a Means to Improve the Delivery of Peptide Drugs. Advanced Drug Delivery Review 8:1-38 (1992).
Bundgard, H. Design of Prodrugs. 1985; pp. 7-9, 21-24 (Elsevier, Amsterdam).
Montgomery et al. Pyridone methylsulfone hydroxamate LpxC inhibitors for the treatment of serious gram-negative infections. J Med Chem 55:1662-1670 (2012).
PCT/US2022/015679 International Search Report and Written Opinion dated May 31, 2022.
PCT/US2022/015682 International Search Report and Written Opinion dated May 31, 2022.
PCT/US2023/071877 International Search Report and Written Opinion dated Oct. 10, 2023.
Ushiyama et al., Lead optimization of 2-hydroxymethyl imidazoles as non-hydroxamate LpxC inhibitors: Discovery of TP0586532. Bioorg Med Chem. 30:115964 (2021).

(Continued)

*Primary Examiner* — Sahar Javanmard

(74) *Attorney, Agent, or Firm* — WILSON SONSINI GOODRICH & ROSATI

(57) ABSTRACT

Provided herein are heterocyclic compounds and pharmaceutical compositions comprising said compounds that are useful for inhibiting the growth of gram-negative bacteria. The subject compounds and compositions are useful for the treatment of bacterial infections, such as pneumonia.

20 Claims, No Drawings

(56) References Cited

OTHER PUBLICATIONS

Vaara. Agents that increase the permeability of the outer membrane. Microbiol. Rev. 56(3):395-411 (Sep. 1992).

Widder et al. Section III: Prodrugs Kinetics. Method in Enzymology. 112:309-396 (1985).

Young et al. Leakage of periplasmic enzymes from envA1 strains of *Escherichia coli*. J. Bacteriol.173(12):3609-3614 (1991).

ANTIBACTERIAL COMPOUNDS

CROSS-REFERENCE TO RELATED APPLICATIONS

This application is a § 371 U.S. National Stage Entry of International Application No. PCT/US2022/015682, filed Feb. 8, 2022, which claims the benefit of U.S. Provisional Patent Application No. 63/148,261, filed on Feb. 11, 2021, which are herein incorporated by reference in their entirety.

STATEMENT AS TO FEDERALLY SPONSORED RESEARCH

This invention was made with government support under IDSEP160030 awarded by the U.S. Department of Health & Human Services. The government has certain rights in the invention.

BACKGROUND OF THE INVENTION

A need exists in the medicinal arts for the effective treatment of illness caused by bacterial infection.

SUMMARY OF THE INVENTION

Provided herein are heterocyclic compounds and pharmaceutical compositions comprising said compounds that are useful for inhibiting the growth of gram-negative bacteria. The subject compounds and compositions are useful for the treatment of bacterial infection, such as pneumonia and the like. In some embodiments, compounds described herein are UDP-{3-O—[(R)-3-hydroxymyristoyl]}-N-acetylglucosamine deacetylase (LpxC) modulator compounds. In some embodiments, the compounds described herein are UDP-{3-O—[(R)-3-hydroxymyristoyl]}-N-acetylglucosamine deacetylase (LpxC) antagonists. In some embodiments, the compounds described herein are UDP-{3-O—[(R)-3-hydroxymyristoyl]}-N-acetylglucosamine deacetylase (LpxC) inhibitors.

In one aspect, described herein is a compound of Formula (I):

Formula (I)

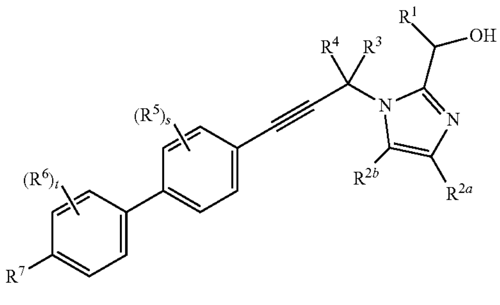

or a pharmaceutically acceptable salt, or solvate thereof, wherein:

$R^1$ is $C_1$-$C_4$ alkyl;

$R^{2a}$ and $R^{2b}$ are each independently hydrogen, halogen, or $C_1$-$C_4$ alkyl;

$R^3$ is hydrogen, —($C_1$-$C_4$ alkylene)-OH, or —($C_1$-$C_4$ alkylene)-$NH_2$;

$R^4$ is hydrogen or $C_1$-$C_4$ alkyl;

each $R^5$ and $R^6$ is independently hydrogen, halogen, or $C_1$-$C_4$ alkyl;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R^8)_2$, —$CH_2N(R')_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl;

each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$;

or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$;

s is 1 or 2; and t is 1 or 2.

In some embodiments, the compound of Formula (I) is a compound of Formula (IIa):

Formula (IIa)

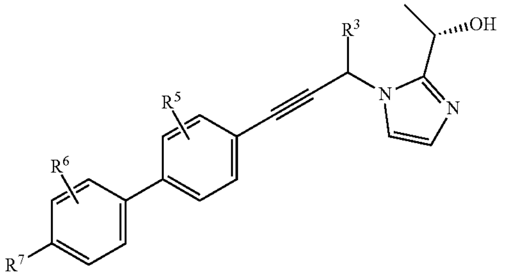

or a pharmaceutically acceptable salt, or solvate thereof, wherein:

$R^3$ is hydrogen, —($C_1$-$C_4$ alkylene)-OH, or —($C_1$-$C_4$ alkylene)-$NH_2$;

$R^5$ is hydrogen or fluoro;

$R^6$ is hydrogen or fluoro;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$—$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R^8)_2$, —$CH_2N(R')_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$;

or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, the compound of Formula (I) or (IIa) is a compound of Formula (III):

Formula (III)

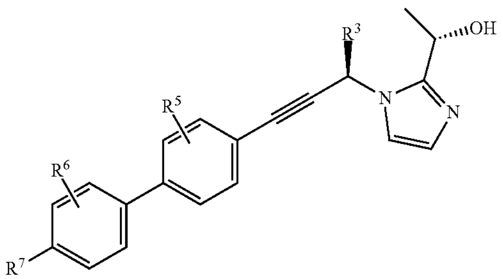

or a pharmaceutically acceptable salt, or solvate thereof, wherein:

$R^3$ is hydrogen, —($C_1$-$C_4$ alkylene)-OH, or —($C_1$-$C_4$ alkylene)-$NH_2$;

$R^5$ is hydrogen or fluoro;

$R^6$ is hydrogen or fluoro;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R^8)_2$, —$CH_2N(R')_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$;

or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, the compound of Formula (I) is a compound of Formula (IV):

Formula (IV)

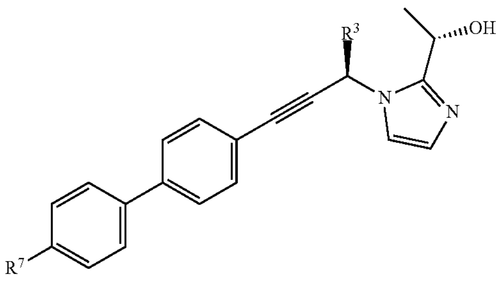

or a pharmaceutically acceptable salt, or solvate thereof, wherein:

$R^3$ is hydrogen, —($C_1$-$C_4$ alkylene)-OH, or —($C_1$-$C_4$ alkylene)-$NH_2$;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ methoxyalkyl, and $C_1$-$C_4$ hydroxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH)$NH_2$, and monocyclic heteroaryl which is unsubstituted or substituted by 1 —$CONH_2$ group.

Any combination of the groups described above for the various variables is contemplated herein. Throughout the specification, groups and substituents thereof are chosen by one skilled in the field to provide stable moieties and compounds.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In another aspect provided herein is a method of treating or preventing a gram-negative bacterial infection in a patient in need thereof comprising administering to the patient a pharmaceutical composition comprising a compound described herein, or a pharmaceutically acceptable salt thereof, and a pharmaceutically acceptable excipient. In some embodiments, the gram-negative bacterial infection is associated with *Pseudomonas aeruginosa*. In some embodiments, the gram-negative bacterial infection is a respiratory infection. In some embodiments, the gram-negative bacterial infection is pneumonia. In some embodiments, provided herein, the gram-negative bacterial infection is community-acquired pneumonia (CAP), health care-associated pneumonia (HCAP), hospital-acquired pneumonia (HAP), ventilator-associate pneumonia (VAP), or a combination thereof. In some embodiments, the patient has been identified as having a lung disease. In some embodiments, the lung disease is a structural lung disease. In some embodiments, the lung disease is cystic fibrosis, bronchiectasis, emphysema, chronic obstructive pulmonary disease (COPD), chronic destroyed lung disease, or a combination thereof. In some embodiments, the administration is to treat an existing infection.

In some embodiments, the administration is provided as prophylaxis. In some embodiments, the compound or a pharmaceutically acceptable salt, or solvate thereof, or the pharmaceutical composition described herein is administered in a solution by inhalation, intravenous injection, or intraperitoneal injection.

In another aspect provided herein is a method of inhibiting UDP-{3-O—[(R)-3-hydroxymyristoyl]}-N-acetylglucosamine deacetylase enzyme comprising contacting the enzyme with a compound described herein.

In another aspect provided herein is a method for treating bacterial infection in a patient in need thereof comprising administering to the patient a composition comprising a compound described herein, or a pharmaceutically acceptable salt thereof, and a pharmaceutically acceptable excipient.

In any of the aforementioned aspects are further embodiments in which the effective amount of the compound of Formula (I), or a pharmaceutically acceptable salt, or solvate thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating UDP-{3-O—[(R)-3-hydroxymyristoyl]}-N-acetylglucosamine deacetylase (LpxC), or for the treatment, prevention or amelioration of one or more symptoms of a disease or condition that would benefit from modulating UDP-{3-O—[(R)-3-hydroxymyristoyl]}-N-acetylglucosamine deacetylase (LpxC), are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference for the specific purposes identified herein.

DETAILED DESCRIPTION OF THE INVENTION

LpxC, Lipid A and Gram-Negative Bacteria

Metalloproteins influence a vast diversity of biological systems, biological processes, and diseases. For example, UDP-{3-O—[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of gram-negative bacteria. LpxC is a zinc(II)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of gram-negative bacteria, making LpxC an attractive target to treat gram-negative infections. To the contrary, LpxC is not a component of Gram-positive bacteria, such as *Staphylococcus aureus*.

In recent years, there has been an increase in resistant and multi-drug resistant strains of bacteria. Thus, there is a need for new antibiotics, especially with new mechanisms of action.

There remains a need for metalloprotein modulators of LpxC useful in the field of therapeutics, diagnostics, and research.

Some embodiments provide a method of inhibiting UDP-{3-O—[(R)-3-hydroxymyristoyl]}-N-acetylglucosamine deacetylase enzyme comprising contacting the enzyme with a compound of Formula (I).

In some embodiments provided herein is a pharmaceutical composition comprising a compound of Formula (I) or a pharmaceutically acceptable salt thereof, and a pharmaceutically acceptable excipient.

Methods of Use

Disclosed herein are methods of treating disease wherein the inhibition of bacterial growth is indicated. Such disease includes gram-negative bacterial infection. In some embodiments, the gram-negative bacterial infection is associated with *Pseudomonas aeruginosa.*

In some embodiments, the method of treating a gram-negative bacterial infection in a patient in need thereof comprises administering to the patient a compound of Formula (I), a pharmaceutical composition comprising a compound of Formula (I), or a pharmaceutically acceptable salt thereof, and a pharmaceutically acceptable excipient. In some embodiments, the method of treating a *Pseudomonas aeruginosa* infection in a patient in need thereof comprises administering to the patient the compound of Formula (I), a pharmaceutical composition comprising a compound of Formula (I), or a pharmaceutically acceptable salt thereof, and a pharmaceutically acceptable excipient.

In some embodiments, the gram-negative bacterial infection is associated with *Pseudomonas aeruginosa*. In some embodiments, the gram-negative bacterial infection is a respiratory infection. In some embodiments, the gram-negative bacterial infection is pneumonia.

In some embodiments, the gram-negative bacterial infection is community-acquired pneumonia (CAP), health care-associated pneumonia (HCAP), hospital-acquired pneumonia (HAP), ventilator-associate pneumonia (VAP), or a combination thereof. In some embodiments, the gram-negative bacterial infection is community-acquired pneumonia (CAP). In some embodiments, the gram-negative bacterial infection is health care-associated pneumonia (HCAP). In some embodiments, the gram-negative bacterial infection is hospital-acquired pneumonia (HAP). In some embodiments, the gram-negative bacterial infection is ventilator-associate pneumonia (VAP).

In some embodiments, the patient has been identified as having a lung disease. In some embodiments, the lung disease is a structural lung disease. In some embodiments, the lung disease is cystic fibrosis, bronchiectasis, emphysema, chronic obstructive pulmonary disease (COPD), chronic destroyed lung disease, or a combination thereof. In some embodiments, the patient has cystic fibrosis. In some embodiments, the patient has bronchiectasis. In some embodiments, the patient has emphysema. In some embodiments, the patient has chronic obstructive pulmonary disease (COPD). In some embodiments, the patient has chronic destroyed lung disease.

In some embodiments the administration is to treat an existing infection.

In some embodiments the administration is provided as prophylaxis.

In some embodiments, the LpxC inhibitory compound as described herein is used for treating or preventing conditions caused by the bacterial production of endotoxin and, in particular, by gram-negative bacteria and bacteria that use LpxC in the biosynthesis of lipopolysaccharide (LPS) or endotoxin. In some embodiments, the method of treating or preventing a condition caused by endotoxin or LPS in a patient in need thereof comprises administering to the patient a pharmaceutical composition comprising a compound of Formula (I), or a pharmaceutically acceptable salt thereof, and a pharmaceutically acceptable excipient.

In another embodiment, the heterocyclic LpxC inhibitory compounds as described herein are useful in the treatment of conditions that are caused or exacerbated by the bacterial production of lipid A and LPS or endotoxin, such as chronic obstructive pulmonary disease (COPD) and acute exacerbations of chronic bronchitis (AECB). In some embodiments, the method of treating or preventing a condition caused by endotoxin or LPS in a patient in need thereof comprises administering to the patient a pharmaceutical composition comprising a compound of Formula (I), or a pharmaceutically acceptable salt thereof, and a pharmaceutically acceptable excipient, wherein the condition caused by endotoxin or LPS is selected from chronic obstructive pulmonary disease (COPD) and acute exacerbations of chronic bronchitis (AECB).

In other embodiments, the compounds of the disclosure can be used for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Kuyvera ascorbata, Kuyvera cryocrescense, Shigella sonnei, Proteus mirabilis, Serratia marcescens, Stenotrophomonas maltophilia, Pseudomonas aeruginosa, Burkholderia cepacia, Acinetobacter baumannii, Alcaligenes xylosoxidans, Flavobacterium meningosepticum*, and *Citrobacter freundi, Haemophilus influenzae, Kluyvera species, Legionella species, Moraxella catarrhalis, Enterobacter species, Acinetobacter species, Klebsiella species, Burkholderia* species and *Proteus* species, and infections caused by other bacterial species such as *Neisseria* species, *Shigella* species, *Salmonella* species, *Helicobacter pylori, Vibrionaceae* and *Bordetella* species as well as the infections caused by a *Brucella* species, *Francisella tularensis* and/or *Yersinia pestis*. In some embodiments, the infection is associated with a *Pseudomonas* species. In some embodiments, the infection is associated with *Pseudomonas aeruginosa*. In some embodiments, the compounds of the disclosure do not inhibit the growth of Gram-positive bacteria, such as *Staphylococcus aureus.*

In some embodiments, the LpxC inhibitory compound as described herein is used in a method of preventing growth of a *Pseudomonas* species. In some embodiments, the *Pseudomonas* species is *Pseudomonas aeruginosa.*

In some instances, antibiotics have suboptimal concentrations in the lung leading to therapeutic failures for lung infections. In some embodiments, the heterocyclic LpxC inhibitory compound of Formula (I) have optimal concentrations in the lung for treating or preventing a gram-negative bacterial infection in the lung. In some embodiments, the compounds are present in the lung in a therapeutically effective amount after administration.

In some embodiments, disclosed herein is a compound described herein, or a pharmaceutically acceptable salt thereof, for use as therapeutically active substance.

In some embodiments, disclosed herein is a compound described herein, or a pharmaceutically acceptable salt thereof, for use in treating or preventing a gram-negative bacterial infection. In some embodiments, the gram-negative bacterial infection is associated with *Pseudomonas aeruginosa*. In some embodiments, the gram-negative bacterial infection is a respiratory infection. In some embodiments, the respiratory infection is pneumonia.

In some embodiments, disclosed herein is the use of a compound described herein, or a pharmaceutically acceptable salt thereof, for the preparation of a medicament for treating or preventing a gram-negative bacterial infection. In some embodiments, the gram-negative bacterial infection is associated with *Pseudomonas aeruginosa*. In some embodiments, the gram-negative bacterial infection is a respiratory infection. In some embodiments, the respiratory infection is pneumonia.

LpxC Inhibitory Compounds

Provided herein, in some embodiments, are heterocyclic LpxC inhibitory compounds and pharmaceutical compositions comprising said compounds. The subject compounds and compositions are useful for inhibiting UDP-{3-O—[(R)-3-hydroxymyristoyl]}-N-acetylglucosamine deacetylase (LpxC) and for the treatment of bacterial infection.

In some embodiments, compounds of Formula (I), including pharmaceutically acceptable salts, prodrugs, active metabolites, and pharmaceutically acceptable solvates thereof, are UDP-{3-O—[(R)-3-hydroxymyristoyl]}-N-acetylglucosamine deacetylase (LpxC) modulators. In some embodiments, the compounds of Formula (I), including pharmaceutically acceptable salts, prodrugs, active metabolites, and pharmaceutically acceptable solvates thereof, are UDP-{3-O—[(R)-3-hydroxymyristoyl]}-N-acetylglucosamine deacetylase (LpxC) antagonists. In some embodiments, the compounds of Formula (I), including pharmaceutically acceptable salts, prodrugs, active metabolites, and pharmaceutically acceptable solvates thereof, are UDP-{3-O—[(R)-3-hydroxymyristoyl]}-N-acetylglucosamine deacetylase (LpxC) inhibitors.

One aspect of the disclosure provides a compound having the structure of Formula (I):

Formula (I)

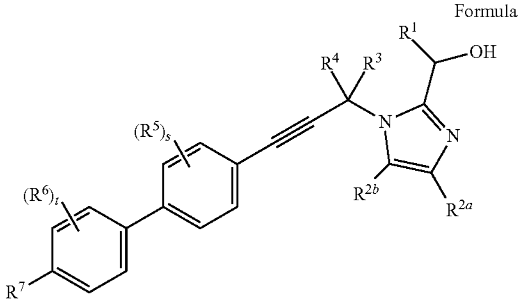

or a pharmaceutically acceptable salt, solvate, or prodrug thereof, wherein:

$R^1$ is $C_1$-$C_4$ alkyl;

$R^{2a}$ and $R^{2b}$ are each independently hydrogen, halogen, or $C_1$-$C_4$ alkyl;

$R^3$ is hydrogen, —($C_1$-$C_4$ alkylene)-OH, or —($C_1$-$C_4$ alkylene)-$NH_2$;

$R^4$ is hydrogen or $C_1$-$C_4$ alkyl;

each $R^5$ and $R^6$ is independently hydrogen, halogen, or $C_1$-$C_4$ alkyl;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R^8)_2$, —$CH_2N(R')_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl;

each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$;

or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$;

s is 1 or 2; and t is 1 or 2.

In some embodiments, $R^1$ is $C_1$-$C_4$ alkyl;

$R^{2a}$ and $R^{2b}$ are each independently hydrogen, halogen, or $C_1$-$C_4$ alkyl;

$R^3$ is hydrogen, —($C_1$-$C_4$ alkylene)-OH, or —($C_1$-$C_4$ alkylene)-$NH_2$;

$R^4$ is hydrogen or $C_1$-$C_4$ alkyl;

each $R^5$ and $R^6$ is independently hydrogen, halogen, or $C_1$-$C_4$ alkyl;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R^8)_2$, —$CH_2N(R')_2$, —$NHCOR^8$, —$NHSO_2R^8$, $C_1$-$C_4$ alkyl, $C_1$-$C_4$ hydroxyalkyl, —C(═O)—$C_1$-$C_4$ hydroxyalkyl, and $C_1$-$C_4$ aminoalkyl;

each $R^8$ is independently hydrogen, $C_1$-$C_4$ alkyl, or 4- to 6-membered heterocycloalkyl, wherein the alkyl or heterocycloalkyl is unsubstituted or substituted by 1, 2, or 3 groups independently selected from —F, —CN, —OH, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$;

or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$;

s is 1 or 2; and t is 1 or 2.

In some embodiments, the compound of Formula (I) is a compound of Formula (Ia) or Formula (Ib):

Formula (Ia)

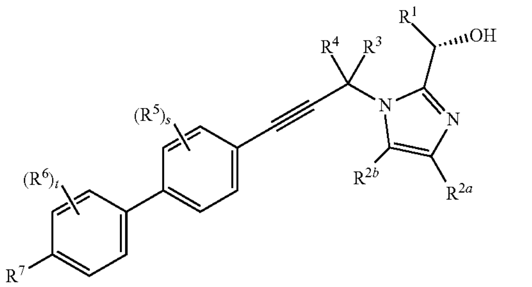

Formula (Ib)

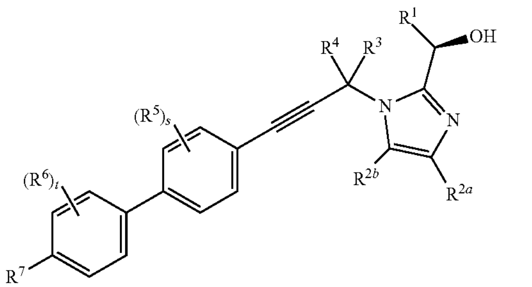

or a pharmaceutically acceptable salt, or solvate thereof.

In some embodiments, the compound is a compound of Formula (Ia), or a pharmaceutically acceptable salt, or solvate thereof. In some embodiments, the compound is a compound of Formula (Ib), or a pharmaceutically acceptable salt, or solvate thereof.

For any and all of the embodiments, substituents are selected from among a subset of the listed alternatives. For example, in some embodiments of a compound of Formula (I), (Ia), or (Ib), $R^1$ is unsubstituted $C_1$-$C_4$ alkyl. In some embodiments, $R^1$ is $C_1$-$C_2$ alkyl. In some embodiments, $R^1$ is $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, $—C(CH_3)_3$. In some embodiments, $R^1$ is $—CH_3$ or $—CH_2CH_3$. In some embodiments, $R^1$ is $—CH_3$.

In some embodiments of a compound of Formula (I), (Ia), or (Ib), $R^{2a}$ and $R^{2b}$ are each independently $R^{2a}$ and $R^{2b}$ are each independently hydrogen, halogen, or unsubstituted $C_1$-$C_4$ alkyl. In some embodiments, $R^{2a}$ and $R^{2b}$ are each independently hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, or $—C(CH_3)_3$. In some embodiments, $R^{2a}$ and $R^{2b}$ are each independently hydrogen, —F, —Cl, $—CH_3$, $—CH_2CH_3$, or $—CH(CH_3)_2$.

In some embodiments of a compound of Formula (I), (Ia), or (Ib), $R^{2a}$ is hydrogen. In some embodiments, $R^{2b}$ is hydrogen. In some embodiments, $R^{2a}$ and $R^{2b}$ are each hydrogen.

In some embodiments of a compound of Formula (I), (Ia), or (Ib), $R^1$ is $—CH_3$; $R^{2'}$ is hydrogen; and $R^{2b}$ is hydrogen.

In some embodiments of a compound of Formula (I), (Ia), or (Ib), $R^4$ is hydrogen or unsubstituted $C_1$-$C_4$ alkyl. In some embodiments, $R^4$ is hydrogen or $C_1$-$C_2$ alkyl. In some embodiments, $R^4$ is hydrogen, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, $—C(CH_3)_3$. In some embodiments, $R^4$ is hydrogen, $—CH_3$ or $—CH_2CH_3$. In some embodiments, $R^4$ is hydrogen or $—CH_3$. In some embodiments, $R^4$ is hydrogen.

In some embodiments, $R^4$ is $—CH_3$.

In some embodiments of a compound of Formula (I), (Ia), or (Ib), each $R^5$ and $R^6$ is independently hydrogen, halogen, or unsubstituted $C_1$-$C_4$ alkyl. In some embodiments, each $R^5$ and $R^6$ is independently hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, or $—C(CH_3)_3$. In some embodiments, each $R^5$ and $R^6$ is independently hydrogen, —F, —Cl, $—CH_3$, $—CH_2CH_3$, or $—CH(CH_3)_2$. In some embodiments, each $R^5$ and $R^6$ is independently hydrogen, fluoro, chloro, or $—CH_3$.

In some embodiments of a compound of Formula (I), (Ia), or (Ib), each $R^5$ is independently hydrogen, halogen, or unsubstituted $C_1$-$C_4$ alkyl. In some embodiments, each $R^5$ is independently hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, or $—C(CH_3)_3$. In some embodiments, each $R^5$ is independently hydrogen, —F, —Cl, $—CH_3$, $—CH_2CH_3$, or $—CH(CH_3)_2$. In some embodiments, each $R^5$ is independently hydrogen, fluoro, chloro, or $—CH_3$.

In some embodiments of a compound of Formula (I), (Ia), or (Ib), each $R^6$ is independently hydrogen, halogen, or unsubstituted $C_1$-$C_4$ alkyl. In some embodiments, each $R^6$ is independently hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, or $—C(CH_3)_3$. In some embodiments, each $R^6$ is independently hydrogen, —F, —Cl, $—CH_3$, $—CH_2CH_3$, or $—CH(CH_3)_2$. In some embodiments, each $R^6$ is independently hydrogen, fluoro, chloro, or $—CH_3$.

In some embodiments of a compound of Formula (I), (Ia), or (Ib), each $R^5$ is independently hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, or $—C(CH_3)_3$; and each $R^6$ is hydrogen. In some embodiments, each $R^5$ is independently hydrogen, —F, —Cl, $—CH_3$, $—CH_2CH_3$, or $—CH(CH_3)_2$; and each $R^6$ is hydrogen. In some embodiments, each $R^5$ is independently hydrogen, fluoro, chloro, or $—CH_3$; and each $R^6$ is hydrogen.

In some embodiments of a compound of Formula (I), (Ia), or (Ib), each $R^5$ is hydrogen; and each $R^6$ is independently hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, or $—C(CH_3)_3$. In some embodiments, each $R^5$ is hydrogen; and each $R^6$ is independently hydrogen, —F, —Cl, $—CH_3$, $—CH_2CH_3$, or $—CH(CH_3)_2$. In some embodiments, each $R^5$ is hydrogen; and each $R^6$ is independently hydrogen, fluoro, chloro, or $—CH_3$.

In some embodiments of a compound of Formula (I), (Ia), or (Ib), each $R^5$ and $R^6$ is hydrogen.

In some embodiments of a compound of Formula (I), (Ia), or (Ib), s is 1. In some embodiments, s is 2.

In some embodiments of a compound of Formula (I), (Ia), or (Ib), t is 1. In some embodiments, t is 2.

In some embodiments of a compound of Formula (I), (Ia), or (Ib), s is 1 or 2; and t is 1.

In some embodiments, s is 1 or 2; and t is 2. In some embodiments, s is 1 and t is 1. In some embodiments, s is 2 and t is 1.

In some embodiments of a compound of Formula (I), (Ia), or (Ib), t is 1 or 2; and s is 1.

In some embodiments, t is 1 or 2; and s is 2. In some embodiments, t is 1 and s is 1. In some embodiments, t is 2 and s is 1.

In some embodiments of a compound of Formula (I), (Ia), or (Ib), each $R^5$ and $R^6$ is independently hydrogen, fluoro, chloro, or —$CH_3$; s is 1; and t is 1.

In some embodiments, the compound of Formula (I) is a compound of Formula (II):

Formula (II)

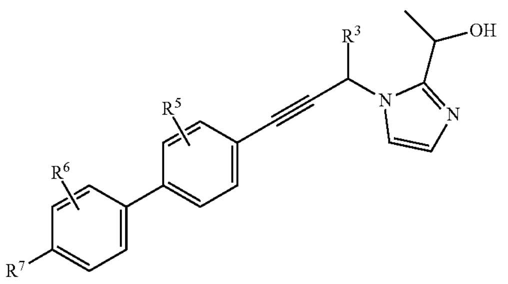

or a pharmaceutically acceptable salt, or solvate thereof.

In some embodiments, $R^5$ is hydrogen or fluoro; and $R^6$ is hydrogen or fluoro.

In some embodiments, $R^3$ is hydrogen, —($C_1$-$C_4$ alkylene)-OH, or —($C_1$-$C_4$ alkylene)-$NH_2$; $R^5$ is hydrogen or fluoro; $R^6$ is hydrogen or fluoro; $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R')_2$, —$CH_2N(R')_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$; or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, $R^3$ is hydrogen, —($C_1$-$C_4$ alkylene)-OH, or —($C_1$-$C_4$ alkylene)-$NH_2$; $R^5$ is hydrogen or fluoro; $R^6$ is hydrogen or fluoro; $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R')_2$, —$CH_2N(R')_2$, —$NHCOR^8$, —$NHSO_2R^8$, $C_1$-$C_4$ alkyl, $C_1$-$C_4$ hydroxyalkyl, —C(═O)—$C_1$-$C_4$ hydroxyalkyl, and $C_1$-$C_4$ aminoalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$; or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, the compound of Formula (I) or (II) is a compound of Formula (IIa) or Formula (IIb):

Formula (IIa)

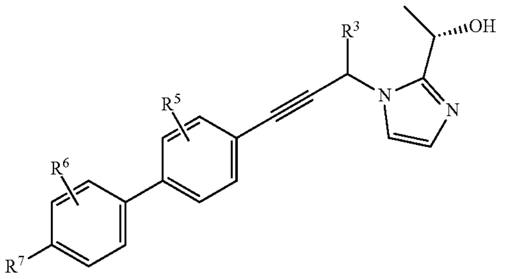

Formula (IIb)

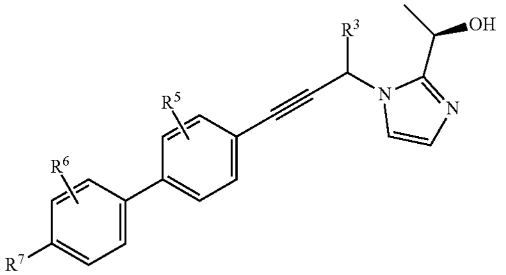

or a pharmaceutically acceptable salt, or solvate thereof.

In some embodiments, $R^5$ is hydrogen or fluoro; and $R^6$ is hydrogen or fluoro.

In some embodiments, $R^3$ is hydrogen, —($C_1$-$C_4$ alkylene)-OH, or —($C_1$-$C_4$ alkylene)-$NH_2$; $R^5$ is hydrogen or fluoro; $R^6$ is hydrogen or fluoro; $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R')_2$, —$CH_2N(R')_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$; or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, $R^3$ is hydrogen, —($C_1$-$C_4$ alkylene)-OH, or —($C_1$-$C_4$ alkylene)-$NH_2$; $R^5$ is hydrogen or fluoro; $R^6$ is hydrogen or fluoro; $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R')_2$, —$CH_2N(R')_2$, —$NHCOR^8$, —$NHSO_2R^8$, $C_1$-$C_4$ alkyl, $C_1$-$C_4$ hydroxyalkyl, —C(═O)—$C_1$-$C_4$ hydroxyalkyl, and $C_1$-$C_4$ aminoalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$; or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, the compound is a compound of Formula (IIa), or a pharmaceutically acceptable salt, or solvate thereof. In some embodiments, the compound is a compound of Formula (IIb), or a pharmaceutically acceptable salt, or solvate thereof.

In some embodiments of a compound of Formula (II), (IIa), or (IIb), $R^5$ is hydrogen. In some embodiments, $R^5$ is fluoro.

In some embodiments of a compound of Formula (II), (IIa), or (IIb), $R^6$ is hydrogen. In some embodiments, $R^6$ is fluoro.

In some embodiments of a compound of Formula (II), (IIa), or (IIb), $R^5$ is hydrogen; and $R^6$ is hydrogen. In some embodiments, $R^5$ is fluoro; and $R^6$ is hydrogen. In some embodiments, $R^5$ is hydrogen; and $R^6$ is fluoro. In some embodiments, $R^5$ is fluoro; and $R^6$ is fluoro.

In some embodiments, the compound of Formula (I) or (II) is a compound of Formula (IIIa), Formula (IIIb), Formula (IIIc), or Formula (IIId):

Formula (IIIa)

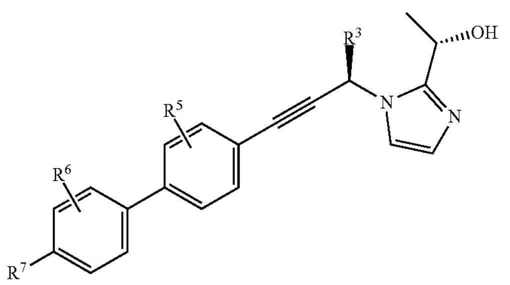

Formula (IIIb)

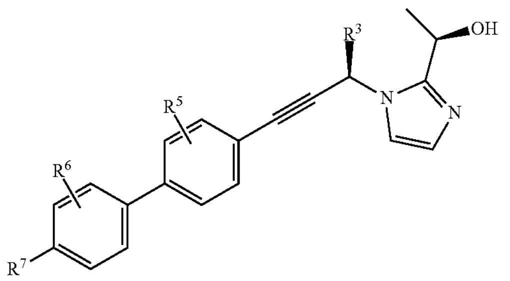

Formula (IIIc)

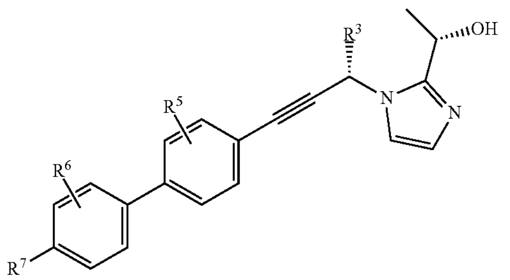

Formula (IIId)

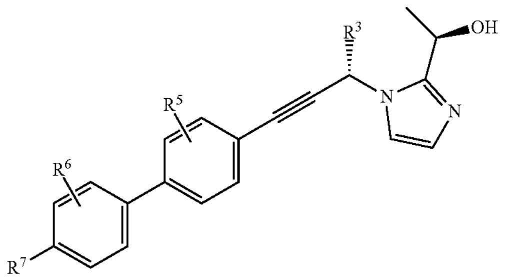

or a pharmaceutically acceptable salt, or solvate thereof.

In some embodiments, $R^5$ is hydrogen or fluoro; and $R^6$ is hydrogen or fluoro.

In some embodiments, $R^3$ is hydrogen, —($C_1$-$C_4$ alkylene)-OH, or —($C_1$-$C_4$ alkylene)-$NH_2$; $R^5$ is hydrogen or fluoro; $R^6$ is hydrogen or fluoro; $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —CON(R')$_2$, —$CH_2$N(R')$_2$, —$NHCOR^8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$; or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, $R^3$ is hydrogen, —($C_1$-$C_4$ alkylene)-OH, or —($C_1$-$C_4$ alkylene)-$NH_2$; $R^5$ is hydrogen or fluoro; $R^6$ is hydrogen or fluoro; $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —CON(R')$_2$, —$CH_2$N(R')$_2$, —$NHCOR^8$, —$NHSO_2R^8$, $C_1$-$C_4$ alkyl, $C_1$-$C_4$ hydroxyalkyl, —C(═O)—$C_1$-$C_4$ hydroxyalkyl, and $C_1$-$C_4$ aminoalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$NH_2$, —OMe, —$N(CH_3)_2$, —$CO_2H$, —$CONH_2$, —$SO_2CH_3$, —C(═NH)$NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$; or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$.

In some embodiments, the compound is a compound of Formula (IIIa), or a pharmaceutically acceptable salt, or solvate thereof. In some embodiments, the compound is a compound of Formula (IIIb), or a pharmaceutically acceptable salt, or solvate thereof. In some embodiments, the compound is a compound of Formula (IIIc), or a pharmaceutically acceptable salt, or solvate thereof. In some embodiments, the compound is a compound of Formula (IIId), or a pharmaceutically acceptable salt, or solvate thereof.

In some embodiments of a compound of Formula (III), (IIIa), or (IIIb), $R^5$ is hydrogen. In some embodiments, $R^5$ is fluoro.

In some embodiments of a compound of Formula (III), (IIIa), or (IIIb), $R^6$ is hydrogen. In some embodiments, $R^6$ is fluoro.

In some embodiments of a compound of Formula (III), (IIIa), or (IIIb), $R^5$ is hydrogen; and $R^6$ is hydrogen. In some embodiments, $R^5$ is fluoro; and $R^6$ is hydrogen. In some embodiments, $R^5$ is hydrogen; and $R^6$ is fluoro. In some embodiments, $R^5$ is fluoro; and $R^6$ is fluoro.

In some embodiments of a compound of Formula (I), (Ia), (Ib), (II), (IIa), (IIb), (IIIa), (IIIb), (IIIc), or (IIId), $R^3$ is hydrogen.

In some embodiments of a compound of Formula (I), (Ia), (Ib), (II), (IIa), (IIb), (IIIa), (IIIb), (IIIc), or (IIId), $R^3$ is —($C_1$-$C_4$ alkylene)-OH. In some embodiments, $R^3$ is —($C_1$-$C_2$ alkylene)-OH. In some embodiments, $R^3$ is —$CH_2OH$, —$CH_2CH_2OH$, —$CH_2CH_2CH_2OH$, —$CH_2CH_2CH_2CH_2OH$, —$CH(CH_3)OH$, —$CH_2CH(CH_3)OH$, —$CH(CH_3)CH_2OH$, —$CH_2CH(CH_2CH_3)OH$, or —$CH(CH_2CH_3)CH_2OH$. In some embodiments, $R^3$ is —$CH_2OH$, —$CH_2CH_2OH$, or —$CH(CH_3)OH$. In some embodiments, $R^3$ is —$CH_2OH$ or —$CH_2CH_2OH$. In some embodiments, $R^3$ is —$CH_2OH$. In some embodiments, $R^3$ is —$CH_2CH_2OH$.

In some embodiments of a compound of Formula (I), (Ia), (Ib), (II), (IIa), (IIb), (IIIa), (IIIb), (IIIc), or (IIId), $R^3$ is —($C_1$-$C_4$ alkylene)-$NH_2$. In some embodiments, $R^3$ is —($C_1$-$C_2$ alkylene)-$NH_2$. In some embodiments, $R^3$ is —$CH_2NH_2$, —$CH_2CH_2NH_2$, —$CH_2CH_2CH_2NH_2$, —$CH_2CH_2CH_2CH_2NH_2$, —$CH(CH_3)NH_2$, —$CH_2CH(CH_3)NH_2$, —$CH(CH_3)CH_2NH_2$, —$CH_2CH(CH_2CH_3)NH_2$, or —$CH(CH_2CH_3)CH_2NH_2$. In some embodiments, $R^3$ is —$CH_2NH_2$, —$CH_2CH_2NH_2$, or —$CH(CH_3)NH_2$. In some embodiments, $R^3$ is —$CH_2NH_2$ or —$CH_2CH_2NH_2$. In some embodiments, $R^3$ is —$CH_2NH_2$.

In some embodiments of a compound of Formula (I), (Ia), (Ib), (II), (IIa), (IIb), (IIIa), (IIIb), (IIIc), or (IIId), $R^3$ is hydrogen or —($C_1$-$C_4$ alkylene)-OH. In some embodiments, $R^3$ is hydrogen or —($C_1$-$C_2$ alkylene)-OH. In some embodiments, $R^3$ is hydrogen, —$CH_2OH$, —$CH_2CH_2OH$, —$CH_2CH_2CH_2OH$, —$CH_2CH_2CH_2CH_2OH$, —$CH(CH_3)OH$, —$CH_2CH(CH_3)OH$, —$CH(CH_3)CH_2OH$, —$CH_2CH(CH_2CH_3)OH$, or —$CH(CH_2CH_3)CH_2OH$. In some embodiments, $R^3$ is hydrogen, —$CH_2OH$, —$CH_2CH_2OH$, or —$CH(CH_3)OH$. In some embodiments, $R^3$ is hydrogen, —$CH_2OH$ or —$CH_2CH_2OH$. In some embodiments, $R^3$ is hydrogen or —$CH_2OH$.

In some embodiments of a compound of Formula (I), (Ia), (Ib), (II), (IIa), (IIb), (IIIa), (IIIb), (IIIc), or (IIId), $R^3$ is hydrogen, —($C_1$-$C_2$ alkylene)-OH, or —($C_1$-$C_2$ alkylene)-$NH_2$. In some embodiments, $R^3$ is hydrogen, —$CH_2OH$, —$CH_2CH_2OH$, or —$CH_2NH_2$. In some embodiments, $R^3$ is hydrogen, —$CH_2OH$, or —$CH_2NH_2$.

In some embodiments of a compound of Formula (I), (Ia), (Ib), (II), (IIa), (IIb), (IIIa), (IIIb), (IIIc), or (IIId), In some embodiments, $R^7$ is $C_1$-$C_6$ alkyl, $C_1$-$C_6$ alkoxy, $C_1$-$C_6$ heteroalkyl, $C_3$-$C_6$ cycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl). In some embodiments, $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ methoxyalkyl, and $C_1$-$C_4$ hydroxyalkyl. In some embodiments, $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl. In some embodiments, $R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ hydroxyalkyl, and $C_1$-$C_4$ methoxyalkyl. In some embodiments, $R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl. In some embodiments, $R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, $NHSO_2R^8$, and —$CH_2CN$. In some embodiments, $R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, and $NHSO_2R^8$.

In some embodiments of a compound of Formula (I), (Ia), (Ib), (II), (IIa), (IIb), (IIIa), (IIIb), (IIIc), or (IIId), each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH)$NH_2$, and monocyclic heteroaryl which is unsubstituted or substituted by 1 —$CONH_2$ group. In some embodiments, each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and monocyclic heteroaryl which is unsubstituted or substituted by 1 —$CONH_2$ group. In some embodiments, each $R^8$ is independently hydrogen, $C_1$-$C_4$ alkyl, —C(═O)—$C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group. In some embodiments, each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group. In some embodiments, each $R^8$ is independently hydrogen, $C_1$-$C_2$ alkyl, or —C(═O)—$C_1$-$C_2$ alkyl, wherein the alkyl is unsubstituted or substituted by 1 or 2 groups independently selected from —CN, —OH, and oxadiazolyl. In some embodiments, each $R^8$ is independently hydrogen or $C_1$-$C_2$ alkyl which is unsubstituted or substituted by 1 or 2 groups independently selected from —CN, —OH, and oxadiazolyl.

In some embodiments of a compound of Formula (I), (Ia), (Ib), (II), (IIa), (IIb), (IIIa), (IIIb), (IIIc), or (IIId), $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ methoxyalkyl, and $C_1$-$C_4$ hydroxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH)$NH_2$, and monocyclic heteroaryl which is unsubstituted or substituted by 1 —$CONH_2$ group. In some embodiments, $R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and monocyclic heteroaryl which is unsubstituted or substituted by 1 —$CONH_2$ group.

In some embodiments of a compound of Formula (I), (Ia), (Ib), (II), (IIa), (IIb), (IIIa), (IIIb), (IIIc), or (IIId), $R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ hydroxyalkyl, and $C_1$-$C_4$ methoxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group. In some embodiments, $R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group.

In some embodiments of a compound of Formula (I), (Ia), (Ib), (II), (IIa), (IIb), (IIIa), (IIIb), (IIIc), or (IIId), $R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, —$NHSO_2R^8$, and —$CH_2CN$; and each $R^8$ is independently hydrogen, $C_1$-$C_2$ alkyl, or —C(═O)—$C_1$-$C_2$ alkyl, wherein the alkyl is unsubstituted or substituted by 1 or 2 groups independently selected from —CN, —OH, and oxadiazolyl. In some embodiments, $R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, —$NHSO_2R^8$, and —$CH_2CN$; and each $R^8$ is independently hydrogen or $C_1$-$C_2$ alkyl which is unsubstituted or substituted by 1 or 2 groups independently selected from —CN, —OH, and oxadiazolyl.

In some embodiments of a compound of Formula (I), (Ia), (Ib), (II), (IIa), (IIb), (IIIa), (IIIb), (IIIc), or (IIId), $R^7$ is $C_1$-$C_6$ alkyl, $C_1$-$C_6$ alkoxy, or $C_1$-$C_6$ heteroalkyl; wherein the alkyl, alkoxy, or heteroalkyl is optionally substituted by 1, 2, or 3 groups independently selected from —OH, —$OCH_3$, —$NH_2$, and —$N(CH_3)_2$.

In some embodiments of a compound of Formula (I), (Ia), (Ib), (II), (IIa), (IIb), (IIIa), (IIIb), (IIIc), or (IIId), $R^7$ is $C_1$-$C_6$ alkoxy. In some embodiments, $R^7$ is $C_1$-$C_5$ alkoxy. In some embodiments, $R^7$ is $C_3$-$C_5$ alkoxy.

In some embodiments of a compound of Formula (I), (Ia), (Ib), (II), (IIa), (IIb), (IIIa), (IIIb), (IIIc), or (IIId), $R^7$ is $C_1$-$C_6$ alkoxy. In some embodiments, $R^7$ is $C_1$-$C_6$ alkoxy; wherein the alkoxy is unsubstituted or substituted by 1, 2, or 3 groups independently selected from —$OR^8$ and —$N(R^8)_2$; and each $R^8$ is independently hydrogen or $C_1$-$C_4$ alkyl. In some embodiments, $R^7$ is $C_1$-$C_6$ alkoxy; wherein the alkoxy is substituted by 1, 2, or 3 groups independently selected from —$OR^8$ and —$N(R^8)_2$; and each $R^8$ is independently hydrogen or $C_1$-$C_4$ alkyl. In some embodiments, $R^7$ is $C_1$-$C_6$ alkoxy; wherein the alkoxy is unsubstituted or substituted by 1, 2, or 3 groups independently selected from —$OR^8$ and —$N(R^8)_2$; and each $R^8$ is independently hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, or —$C(CH_3)_3$. In some embodiments, $R^7$ is $C_1$-$C_6$ alkoxy; wherein the alkoxy is substituted by 1, 2, or 3 groups independently selected from —$OR^8$ and —$N(R^8)_2$; and each $R^8$ is independently hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, or —$C(CH_3)_3$. In some embodiments, $R^7$ is $C_1$-$C_6$ alkoxy; wherein the alkoxy is unsubstituted or substituted by 1, 2, or 3 groups independently selected from —$OR^8$ and —$N(R^8)_2$; and each $R^8$ is independently hydrogen, —$CH_3$, —$CH_2CH_3$, or —$CH(CH_3)_2$. In some embodiments, $R^7$ is $C_1$-$C_6$ alkoxy; wherein the alkoxy is substituted by 1, 2, or 3 groups independently selected from —$OR^8$ and —$N(R^8)_2$; and each $R^8$ is independently hydrogen, —$CH_3$, —$CH_2CH_3$, or —$CH(CH_3)_2$. In some embodiments, $R^7$ is $C_1$-$C_6$ alkoxy; wherein the alkoxy is unsubstituted or substituted by 1, 2, or 3 groups independently selected from —OH, —$OCH_3$, —$NH_2$, and —$N(CH_3)_2$. In some embodiments, $R^7$ is $C_1$-$C_6$ alkoxy; wherein the alkoxy is substituted by 1, 2, or 3 groups independently selected from —OH, —$OCH_3$, —$NH_2$, and —$N(CH_3)_2$. In some embodiments, $R^7$ is $C_1$-$C_6$ alkoxy; wherein the alkoxy is unsubstituted or substituted by 1 or 2 groups independently selected from —OH, —$OCH_3$, —$NH_2$, and —$N(CH_3)_2$. In some embodiments, $R^7$ is $C_1$-$C_6$ alkoxy; wherein the alkoxy is substituted by 1 or 2 groups independently selected from —OH, —$OCH_3$, —$NH_2$, and —$N(CH_3)_2$.

In some embodiments of a compound of Formula (I), (Ia), (Ib), (II), (IIa), (IIb), (IIIa), (IIIb), (IIIc), or (IIId), $R^7$ is $C_1$-$C_5$ alkoxy. In some embodiments, $R^7$ is $C_1$-$C_5$ alkoxy; wherein the alkoxy is unsubstituted or substituted by 1, 2, or 3 groups independently selected from —$OR^8$ and —$N(R^8)_2$; and each $R^8$ is independently hydrogen or $C_1$-$C_4$ alkyl. In some embodiments, $R^7$ is $C_1$-$C_5$ alkoxy; wherein the alkoxy is unsubstituted or substituted by 1, 2, or 3 groups independently selected from —OH, —$OCH_3$, —$NH_2$, and —$N(CH_3)_2$. In some embodiments, $R^7$ is $C_1$-$C_5$ alkoxy; wherein the alkoxy is substituted by 1, 2, or 3 groups independently selected from —OH, —$OCH_3$, —$NH_2$, and —$N(CH_3)_2$. In some embodiments, $R^7$ is $C_1$-$C_5$ alkoxy; wherein the alkoxy is unsubstituted or substituted by 1 or 2 groups independently selected from —OH, —$OCH_3$, —$NH_2$, and —$N(CH_3)_2$. In some embodiments, $R^7$ is $C_1$-$C_5$ alkoxy; wherein the alkoxy is substituted by 1 or 2 groups independently selected from —OH, —$OCH_3$, —$NH_2$, and —$N(CH_3)_2$. In some embodiments, $R^7$ is $C_1$-$C_5$ alkoxy; wherein the alkoxy is substituted by 1 or 2 groups independently selected from —OH, —$OCH_3$, and —$NH_2$.

In some embodiments of a compound of Formula (I), (Ia), (Ib), (II), (IIa), (IIb), (IIIa), (IIIb), (IIIc), or (IIId), $R^7$ is $C_3$-$C_5$ alkoxy. In some embodiments, $R^7$ is $C_3$-$C_5$ alkoxy; wherein the alkoxy is unsubstituted or substituted by 1, 2, or 3 groups independently selected from —$OR^8$ and —$N(R^8)_2$; and each $R^8$ is independently hydrogen or $C_1$-$C_4$ alkyl. In some embodiments, $R^7$ is $C_3$-$C_5$ alkoxy; wherein the alkoxy is unsubstituted or substituted by 1, 2, or 3 groups independently selected from —OH, —$OCH_3$, —$NH_2$, and —$N(CH_3)_2$. In some embodiments, $R^7$ is $C_3$-$C_5$ alkoxy; wherein the alkoxy is substituted by 1, 2, or 3 groups independently selected from —OH, —$OCH_3$, —$NH_2$, and —$N(CH_3)_2$. In some embodiments, $R^7$ is $C_3$-$C_5$ alkoxy; wherein the alkoxy is unsubstituted or substituted by 1 or 2 groups independently selected from —OH, —$OCH_3$, —$NH_2$, and —$N(CH_3)_2$. In some embodiments, $R^7$ is $C_3$-$C_5$ alkoxy; wherein the alkoxy is substituted by 1 or 2 groups independently selected from —OH, —$OCH_3$, —$NH_2$, and —$N(CH_3)_2$.

In some embodiments of a compound of Formula (I), (Ia), (Ib), (II), (IIa), (IIb), (IIIa), (IIIb), (IIIc), or (IIId), $R^7$ is $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl). In some embodiments, $R^7$ is $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the cycloalkyl or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH)$NH_2$, and 5-membered monocyclic heteroaryl which is unsubstituted or substituted by 1 —$CONH_2$ group. In some embodiments, $R^7$ is $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the cycloalkyl or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group. In some embodiments, $R^7$ is $C_3$-$C_4$ cycloalkyl, 4- to 6-membered heterocycloalkyl, —O—($C_3$-$C_4$ cycloalkyl), or —O-(4- to 6-membered heterocycloalkyl); wherein the cycloalkyl or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_2$ alkyl, or —C(═O)—$C_1$-$C_2$ alkyl, wherein the alkyl is unsubstituted or substituted by 1, 2, or 3 groups independently selected from —F, —CN, —OH, and monocyclic 5-membered heteroaryl which is unsubstituted or substituted by 1 —$CONH_2$ group. In some embodiments, $R^7$ is $C_3$-$C_4$ cycloalkyl, 4- to 6-membered heterocycloalkyl, —O—($C_3$-$C_4$ cycloalkyl), or —O-(4- to 6-membered heterocycloalkyl); wherein the cycloalkyl or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen or $C_1$-$C_2$ alkyl which is unsubstituted or substituted by 1, 2, or 3 groups independently selected from —F, —CN, —OH, and monocyclic 5-membered heteroaryl which is unsubstituted or substituted by 1 —$CONH_2$ group.

In some embodiments of a compound of Formula (I), (Ia), (Ib), (II), (IIa), (IIb), (IIIa), (IIIb), (IIIc), or (IIId), $R^7$ is —O—($C_3$-$C_6$ cycloalkyl) or —O-(3- to 6-membered heterocycloalkyl); wherein the cycloalkyl or heterocycloalkyl is unsubstituted or substituted by 1, 2, or 3 groups independently selected from —$OR^8$, —$N(R^8)_2$, $C_1$-$C_4$ alkyl, and $C_1$-$C_4$ hydroxyalkyl. In some embodiments, $R^7$ is —O—($C_3$-$C_6$ cycloalkyl) or —O-(3- to 6-membered heterocycloalkyl); wherein the cycloalkyl or heterocycloalkyl is unsubstituted or substituted by 1, 2, or 3 groups independently selected from —OH, —$OCH_3$, —$NH_2$, —$N(CH_3)_2$, —$CH_3$, and —$CH_2CH_2OH$. In some embodiments, $R^7$ is —O—($C_3$-$C_6$ cycloalkyl) or —O-(3- to 6-membered heterocycloalkyl); wherein the cycloalkyl or heterocycloalkyl is unsubstituted or substituted by 1 or 2 groups independently selected from —OH, —$OCH_3$, —$NH_2$, —$N(CH_3)_2$, —$CH_3$, and —$CH_2CH_2OH$.

In some embodiments of a compound of Formula (I), (Ia), (Ib), (II), (IIa), (IIb), (IIIa), (IIIb), (IIIc), or (IIId), $R^7$ is —O—($C_3$-$C_6$ cycloalkyl). In some embodiments, $R^7$ is —O—($C_3$-$C_6$ cycloalkyl); wherein the cycloalkyl is unsubstituted or substituted by 1, 2, or 3 groups independently selected from —$OR^8$, —$N(R^8)_2$, $C_1$-$C_4$ alkyl, and $C_1$-$C_4$ hydroxyalkyl. In some embodiments, $R^7$ is —O—($C_3$-$C_6$ cycloalkyl); wherein the cycloalkyl is unsubstituted or substituted by 1, 2, or 3 groups independently selected from —$OR^8$ and —$N(R^8)_2$. In some embodiments, $R^7$ is —O—($C_3$-$C_6$ cycloalkyl); wherein the cycloalkyl is unsubstituted or substituted by 1, 2, or 3 groups independently selected from —OH, —$OCH_3$, —$NH_2$, and —$N(CH_3)_2$. In some embodiments, $R^7$ is —O—($C_3$-$C_6$ cycloalkyl); wherein the cycloalkyl is unsubstituted or substituted by 1 or 2 groups independently selected from —OH, —$OCH_3$, —$NH_2$, and —$N(CH_3)_2$. In some embodiments, $R^7$ is —O—($C_3$-$C_6$ cycloalkyl); wherein the cycloalkyl is unsubstituted or substituted by 1 or 2 groups independently selected from —OH and —$NH_2$.

In some embodiments of a compound of Formula (I), (Ia), (Ib), (II), (IIa), (IIb), (IIIa), (IIIb), (IIIc), or (IIId), $R^7$ is —O—($C_3$-$C_4$ cycloalkyl); wherein the cycloalkyl is unsubstituted or substituted by 1, 2, or 3 groups independently selected from —$OR^8$, —$N(R^8)_2$, $C_1$-$C_4$ alkyl, and $C_1$-$C_4$ hydroxyalkyl. In some embodiments, $R^7$ is —O—($C_3$-$C_4$ cycloalkyl); wherein the cycloalkyl is unsubstituted or substituted by 1, 2, or 3 groups independently selected from —$OR^8$ and —$N(R^8)_2$.

In some embodiments, $R^7$ is —O—($C_3$-$C_4$ cycloalkyl); wherein the cycloalkyl is unsubstituted or substituted by 1, 2, or 3 groups independently selected from —OH, —$OCH_3$, —$NH_2$, and —$N(CH_3)_2$.

In some embodiments, $R^7$ is —O—($C_3$-$C_4$ cycloalkyl); wherein the cycloalkyl is substituted by 1 or 2 groups independently selected from —OH, —$OCH_3$, —$NH_2$, and —$N(CH_3)_2$. In some embodiments, $R^7$ is —O—($C_3$-$C_4$ cycloalkyl); wherein the cycloalkyl is substituted by 1 or 2 groups independently selected from —OH and —$NH_2$.

In some embodiments of a compound of Formula (I), (Ia), (Ib), (II), (IIa), (IIb), (IIIa), (IIIb), (IIIc), or (IIId), $R^7$ is —O-(cyclopropyl); wherein the cyclopropyl is unsubstituted or substituted by 1 or 2 groups independently selected from —OH and —$NH_2$. In some embodiments, $R^7$ is —O-(cyclopropyl); wherein the cyclopropyl is substituted by 1 group selected from —OH and —$NH_2$. In some embodiments, $R^7$ is —O-(cyclopropyl); wherein the cyclopropyl is substituted by 1 —OH group. In some embodiments, $R^7$ is —O-(cyclopropyl); wherein the cyclopropyl is substituted by 1 —$NH_2$ group.

In some embodiments of a compound of Formula (I), (Ia), (Ib), (II), (IIa), (IIb), (IIIa), (IIIb), (IIIc), or (IIId), $R^7$ is —O-(4- to 6-membered heterocycloalkyl). In some embodiments, $R^7$ is —O-(4- to 6-membered heterocycloalkyl); wherein the heterocycloalkyl is unsubstituted or substituted by 1, 2, or 3 groups independently selected from —$OR^8$, —$N(R^8)_2$, $C_1$-$C_4$ alkyl, and $C_1$-$C_4$ hydroxyalkyl. In some embodiments, $R^7$ is —O-(4- to 6-membered heterocycloalkyl); wherein the heterocycloalkyl is unsubstituted or substituted by 1, 2, or 3 groups independently selected from —OH, —$OCH_3$, —$NH_2$, —$N(CH_3)_2$, and —$CH_3$. In some embodiments, $R^7$ is —O-(4- to 6-membered heterocycloalkyl); wherein the heterocycloalkyl is substituted by 1 or 2 groups independently selected from —OH, —$OCH_3$, —$NH_2$, —$N(CH_3)_2$, —$CH_2CN$, —$CH_3$, and —$CH_2CH_2OCH_3$.

In some embodiments, $R^7$ is —O-(4- to 6-membered heterocycloalkyl); wherein the heterocycloalkyl is substituted by 1 or 2 groups independently selected from —OH, —$OCH_3$, —$NH_2$, —$N(CH_3)_2$, and —$CH_3$. In some embodiments, $R^7$ is —O-(4- to 6-membered heterocycloalkyl);

wherein the heterocycloalkyl is substituted by 1 or 2 groups independently selected from —OH, —$OCH_3$, —$NH_2$, —$N(CH_3)_2$, and —$CH_3$.

In some embodiments of a compound of Formula (I), (Ia), (Ib), (II), (IIa), (IIb), (IIIa), (IIIb), (IIIc), or (IIId), $R^7$ is —O-(tetrahydrofuranyl); wherein the tetrahydrofuranyl is unsubstituted or substituted by 1 or 2 groups independently selected from —OH, —$OCH_3$, —$NH_2$, —$N(CH_3)_2$, and —$CH_2CH_2OH$. In some embodiments, $R^7$ is —O-(tetrahydrofuranyl); wherein the tetrahydrofuranyl is substituted by 1 group selected from —OH and —$NH_2$.

In some embodiments of a compound of Formula (I), (Ia), (Ib), (II), (IIa), (IIb), (IIIa), (IIIb), (IIIc), or (IIId), $R^7$ is $C_3$-$C_4$ cycloalkyl. In some embodiments, $R^7$ is $C_3$-$C_4$ cycloalkyl; wherein the cycloalkyl is substituted by 1 or 2 groups independently selected from —$N(R^8)_2$, —$OR^8$, and —$NHSO_2R^8$; and each $R^8$ is independently hydrogen, $C_1$-$C_4$ alkyl, —C(═O)—$C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group. In some embodiments, $R^7$ is $C_3$-$C_4$ cycloalkyl; wherein the cycloalkyl is substituted by 1 or 2 groups independently selected from —$N(R^8)_2$, —$OR^8$, and —$NHSO_2R^8$; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group. In some embodiments, $R^7$ is $C_3$-$C_4$ cycloalkyl; wherein the cycloalkyl is substituted by 1 group selected from —OH, —OMe, and —$N(R^8)_2$, and —$NHSO_2R^8$; and each $R^8$ is independently hydrogen, $C_1$-$C_2$ alkyl, or —C(═O)—$C_1$-$C_2$ alkyl, wherein the alkyl is unsubstituted or substituted by 1 or 2 groups independently selected from —CN, —OH, and oxadiazolyl. In some embodiments, $R^7$ is $C_3$-$C_4$ cycloalkyl; wherein the cycloalkyl is substituted by 1 group selected from —OH, —OMe, and —$N(R^8)_2$, and —$NHSO_2R^8$; and each $R^8$ is independently hydrogen or $C_1$-$C_2$ alkyl which is unsubstituted or substituted by 1 or 2 groups independently selected from —CN, —OH, and oxadiazolyl. In some embodiments, $R^7$ is cyclobutyl; wherein the cyclobutyl is substituted by 1 —$N(R')_2$ group; and each $R^8$ is independently hydrogen, $C_1$-$C_2$ alkyl, or —C(═O)—$C_1$-$C_4$ alkyl, wherein the alkyl is unsubstituted or substituted by 1 or 2 groups independently selected from —CN, —OH, and oxadiazolyl. In some embodiments, $R^7$ is cyclobutyl; wherein the cyclobutyl is substituted by 1 —$N(R^8)_2$ group; and each $R^8$ is independently hydrogen or $C_1$-$C_2$ alkyl which is unsubstituted or substituted by 1 or 2 groups independently selected from —CN, —OH, and oxadiazolyl.

In some embodiments of a compound of Formula (I), (Ia), (Ib), (II), (IIa), (IIb), (IIIa), (IIIb), (IIIc), or (IIId), $R^7$ is

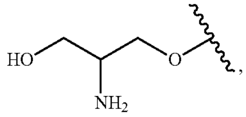, 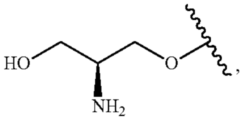,

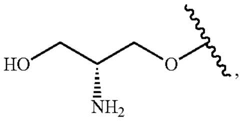, 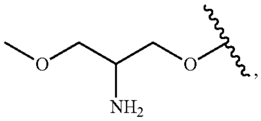,

-continued

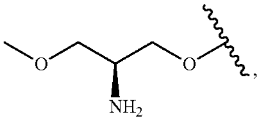, 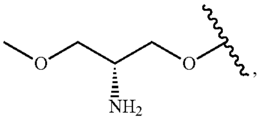,

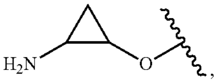, 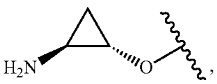,

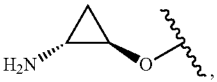, 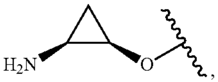,

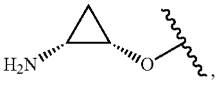, 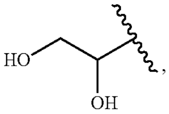,

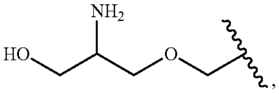, 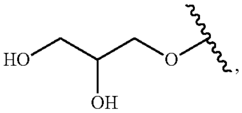,

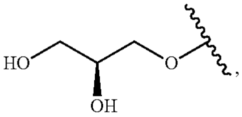, 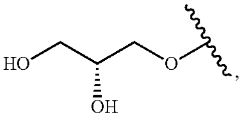,

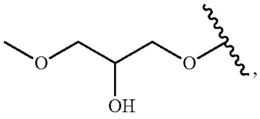, 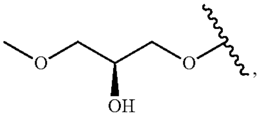,

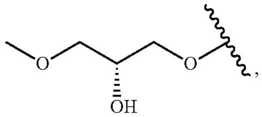, 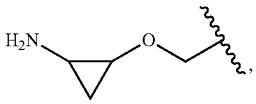,

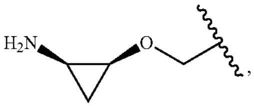, 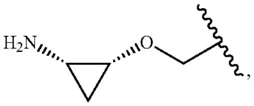,

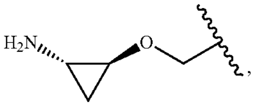, 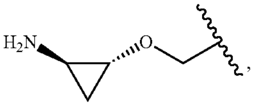,

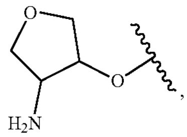, 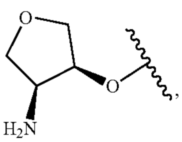,

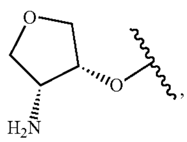, 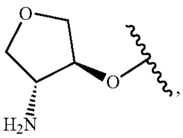,

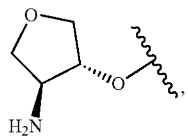, 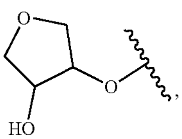,

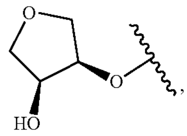, 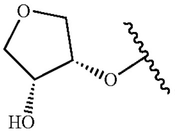,

-continued
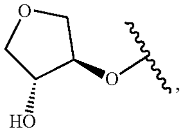,
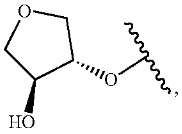,
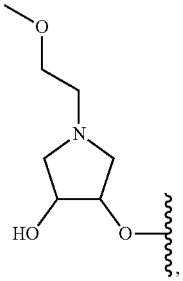,
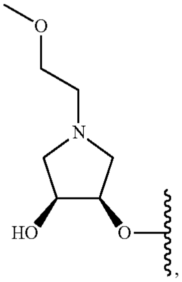,
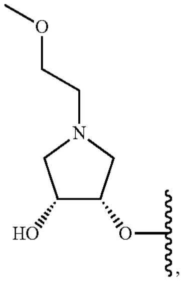,
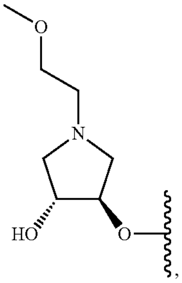,
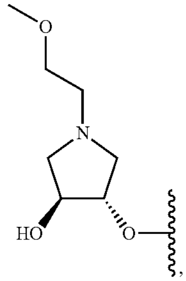,
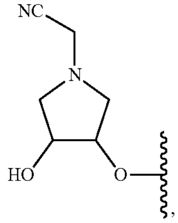,
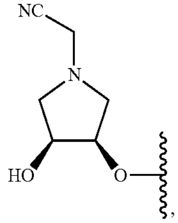,
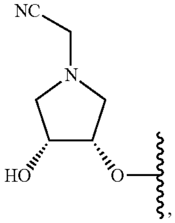,
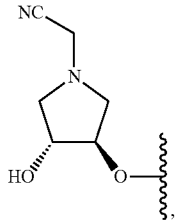,
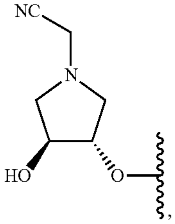,
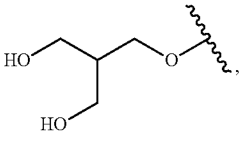,
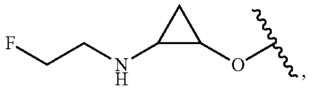,
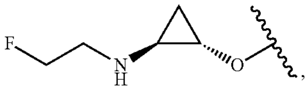,
-continued
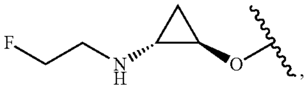,
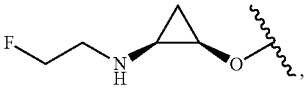,
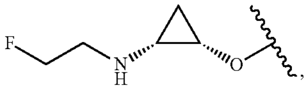,
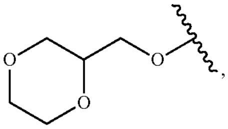,
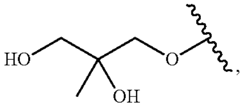,
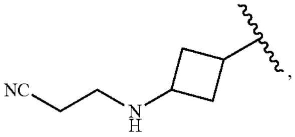,
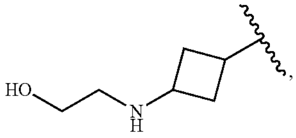,
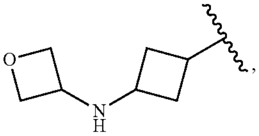,
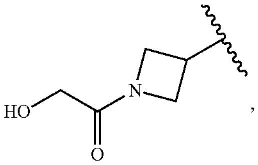,
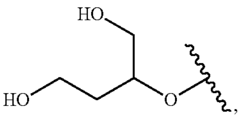,
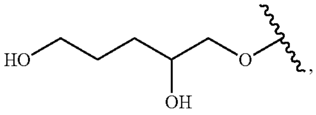,
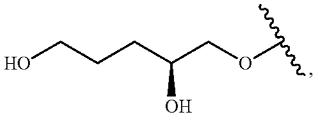,
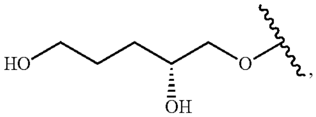,
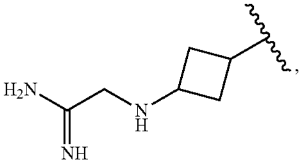,
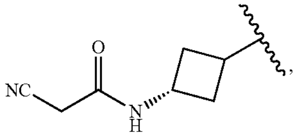,
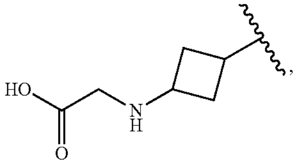, -continued
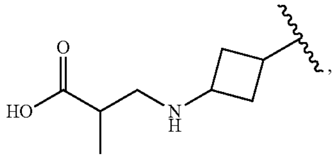,
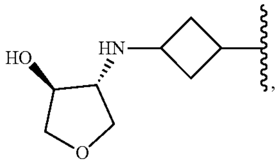,
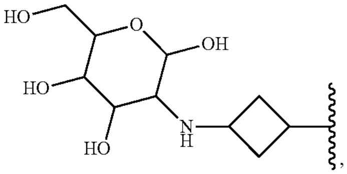,
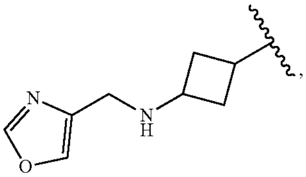,
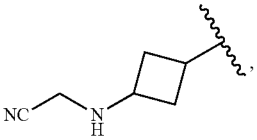,
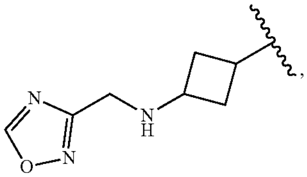,
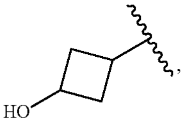,
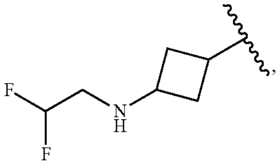,
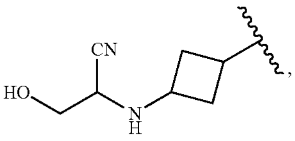,
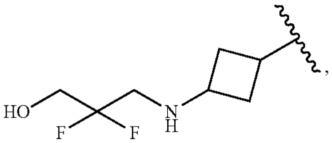,
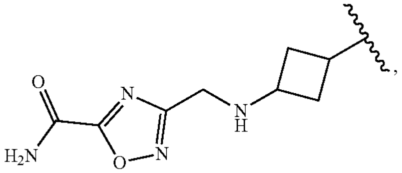, or
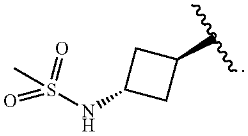.
In some embodiments of a compound of Formula (I), (Ia), (Ib), (II), (IIa), (IIb), (IIIa), (IIIb), (IIIc), or (IIId), $R^7$ is
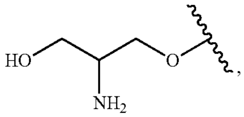, 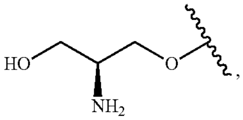,
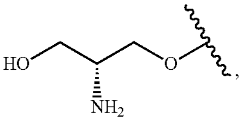, 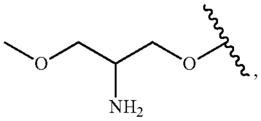,
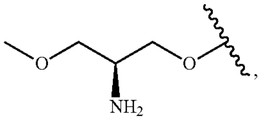, 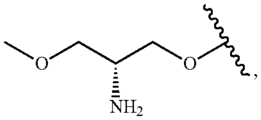,
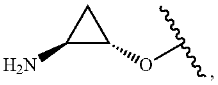, 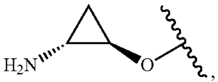,
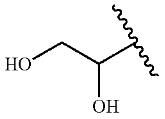, 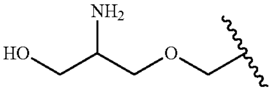,
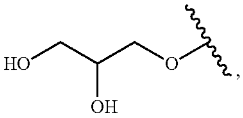, 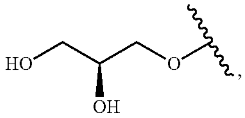,
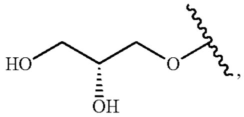, 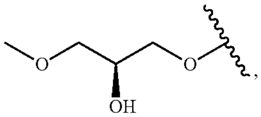,
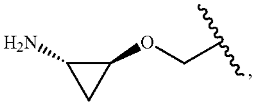, 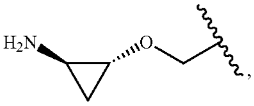,
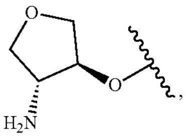, 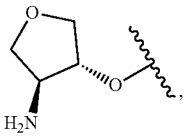,
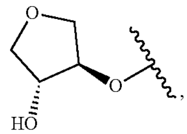, 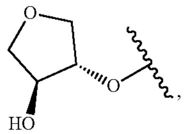,
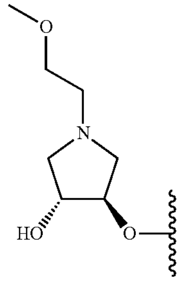, 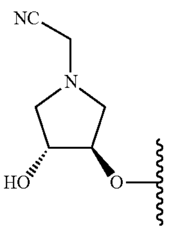,
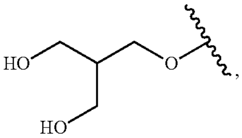, 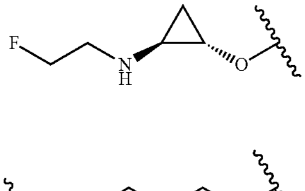,
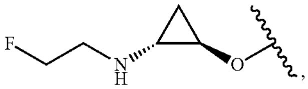, 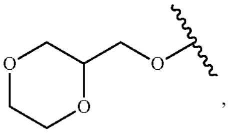, -continued
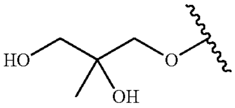,
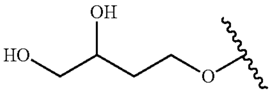,
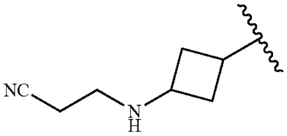,
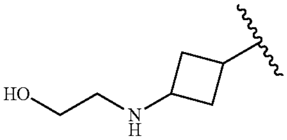,
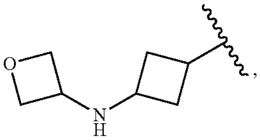,
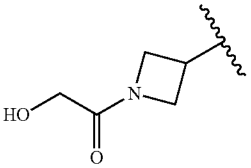,
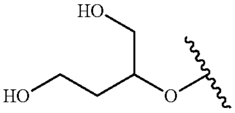,
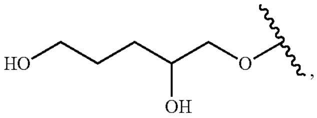,
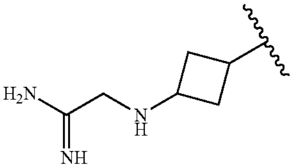,
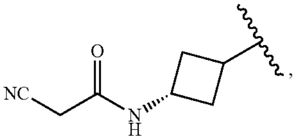,
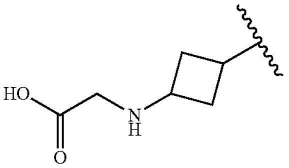,
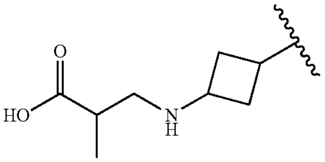,
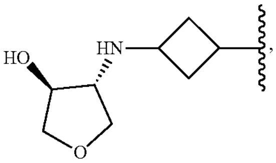,
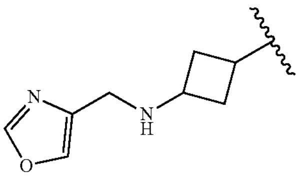,
-continued
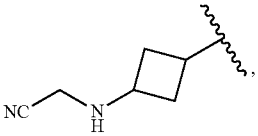,
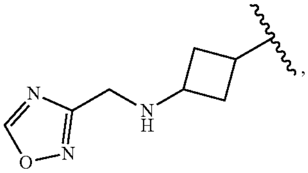,
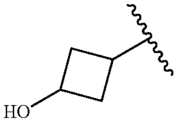,
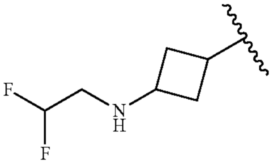,
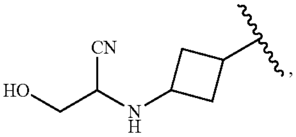,
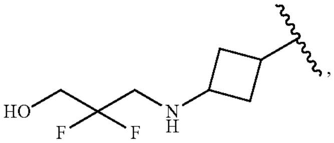,
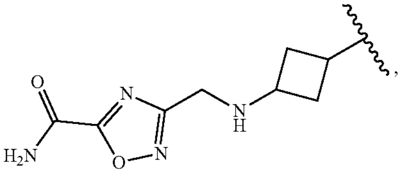, or
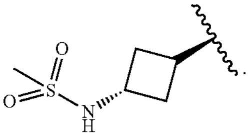.
In some embodiments of a compound of Formula (I), (Ia), (Ib), (II), (Ia), (IIb), (IIIa), (IIIb), (IIIc), or (IIId), $R^7$ is
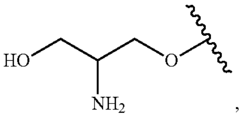,
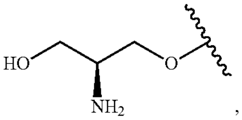,
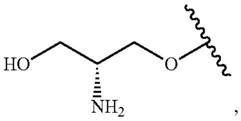,
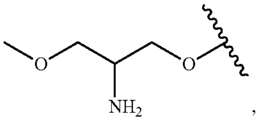,
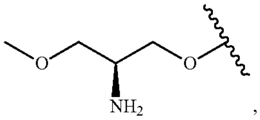,
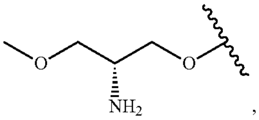,
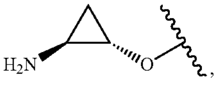,
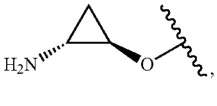, -continued
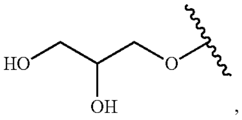 , 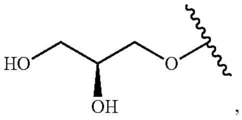 ,
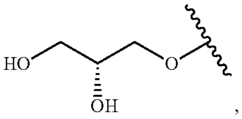 , 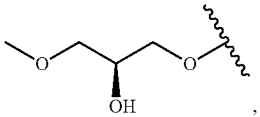 ,
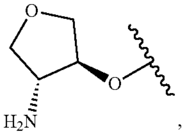 , 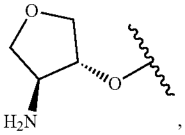 , 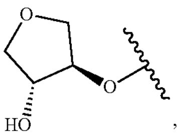 ,
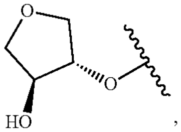 , 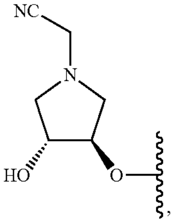 ,
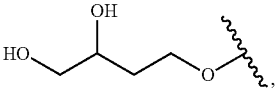 ,
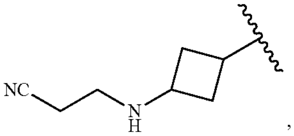 ,
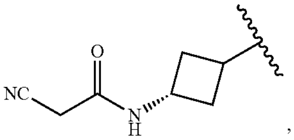 ,
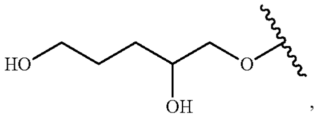 ,
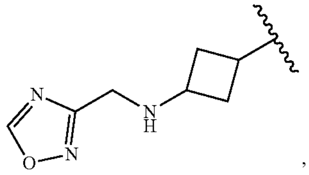 , 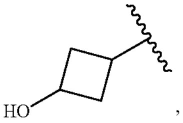 ,
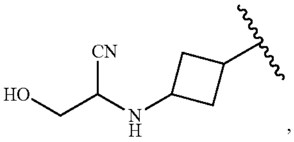 , or 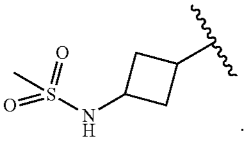 .
In some embodiments of a compound of Formula (I), (Ia), (Ib), (II), (IIa) (IIb), (IIIa), (IIIb), (IIIc), or (IIId), $R^7$ is
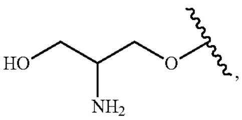 , 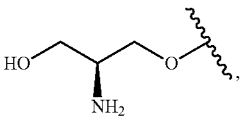 ,
-continued
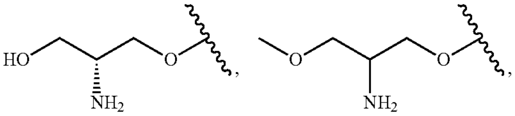
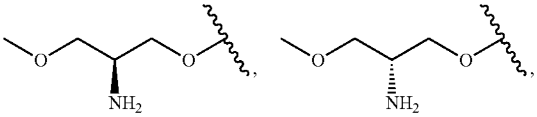
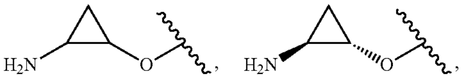
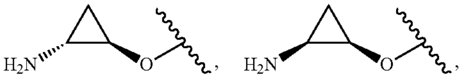
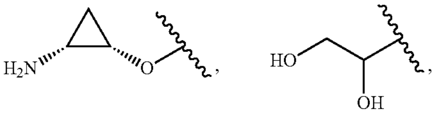
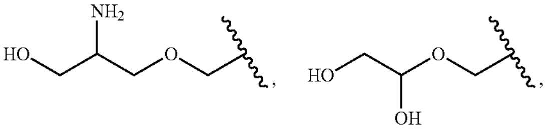
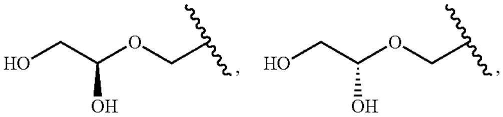
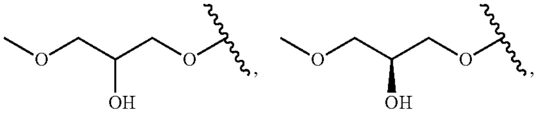
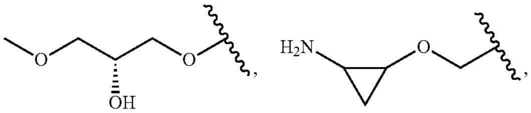
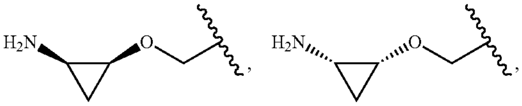
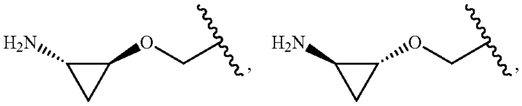
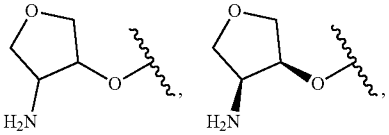
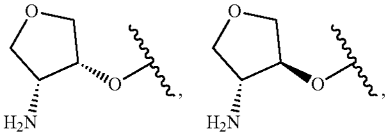
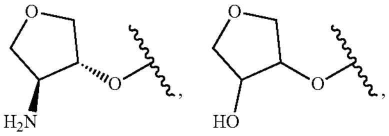
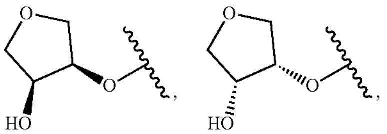

-continued
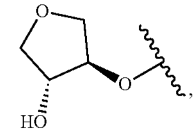, 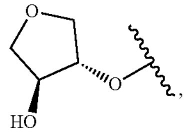,
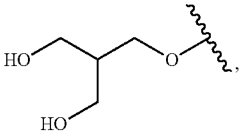, 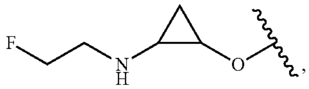,
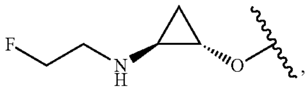,
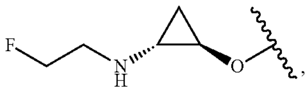,
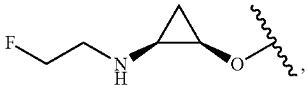,
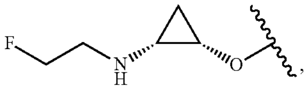, 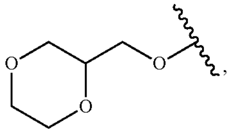,
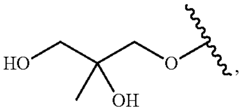, 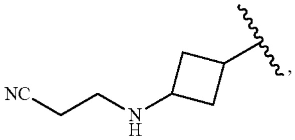,
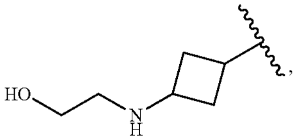, 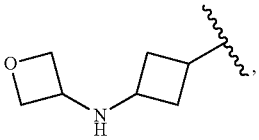,
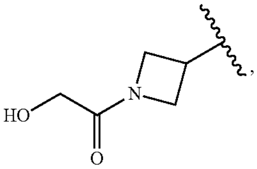, 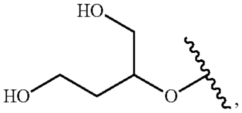,
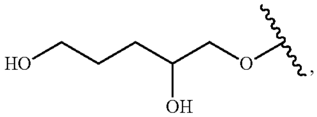,
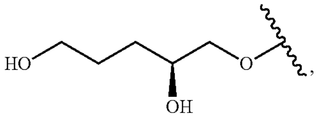,
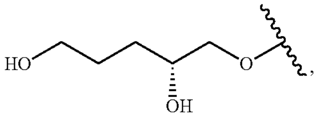,
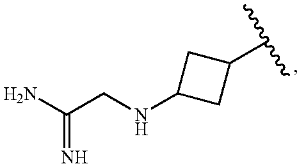,
-continued
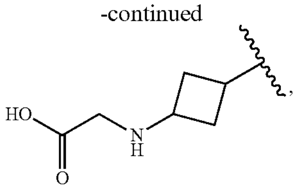,
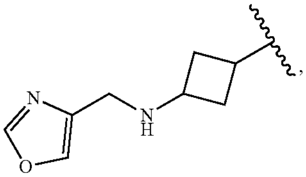, 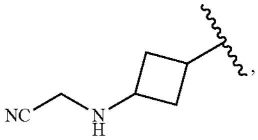,
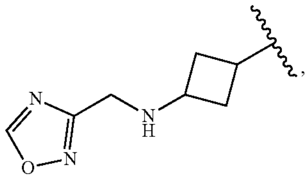, 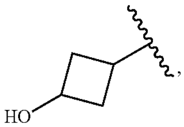,
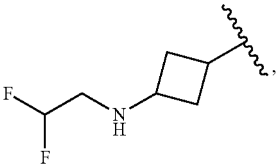, 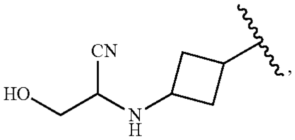,
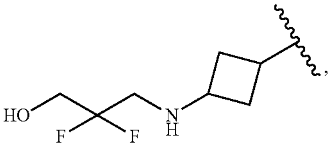,
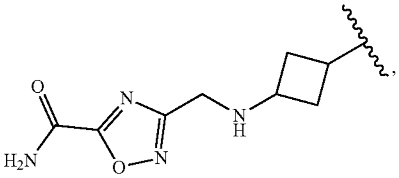, or
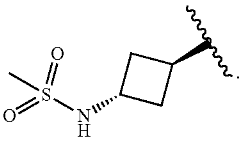.
In some embodiments of a compound of Formula (I), (Ia), (Ib), (II) (IIa), (IIb), (IIIa), (IIIb), (IIIc), or (IIId), $R^7$ is
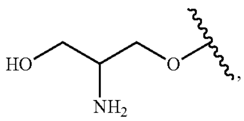, 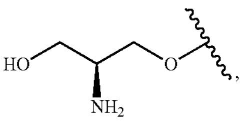,
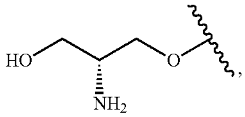, 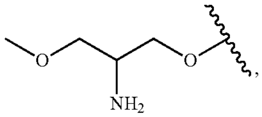,
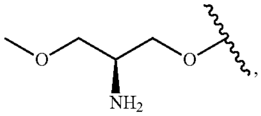, 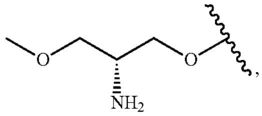,
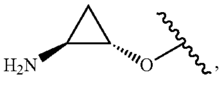, 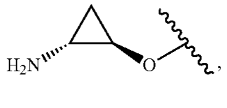, -continued
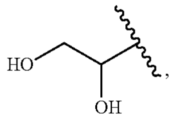,
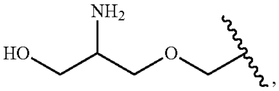,
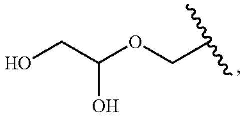,
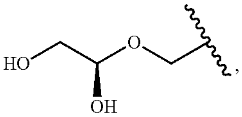,
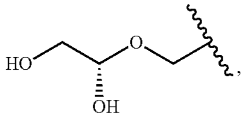,
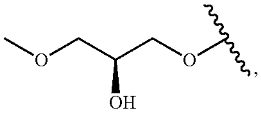,
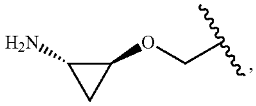,
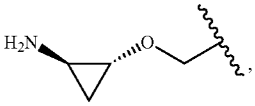,
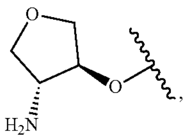,
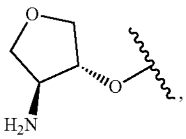,
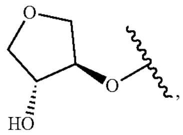,
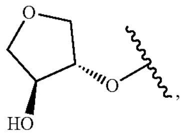,
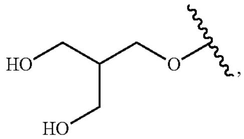,
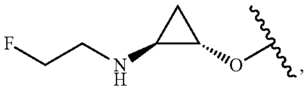,
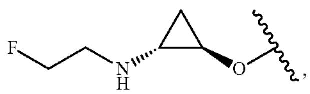,
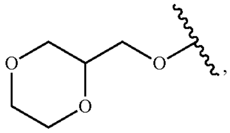,
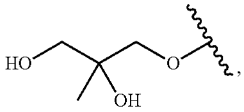,
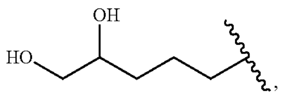,
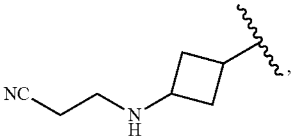,
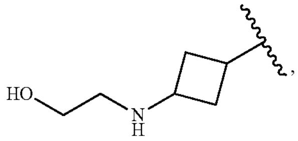,
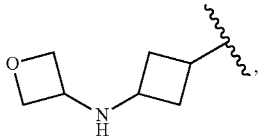,
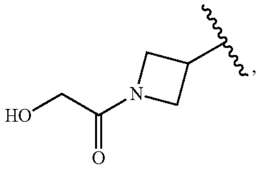,
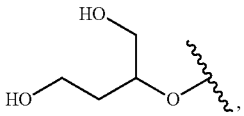,
-continued
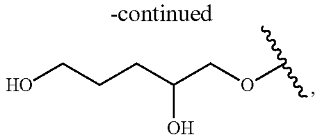,
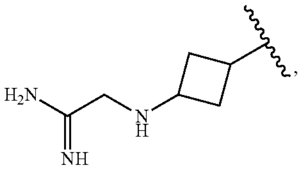,
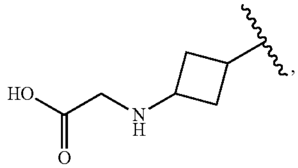,
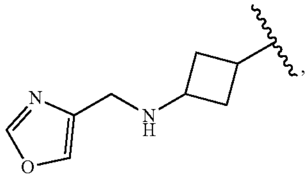,
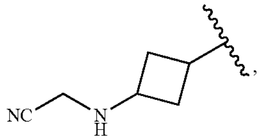,
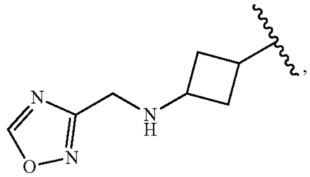,
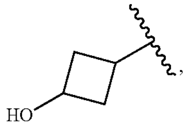,
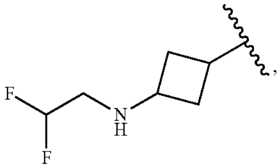,
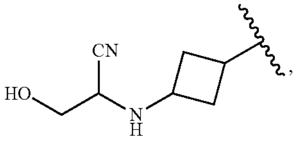,
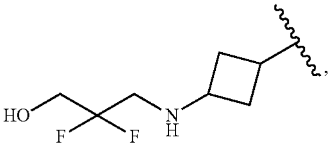,
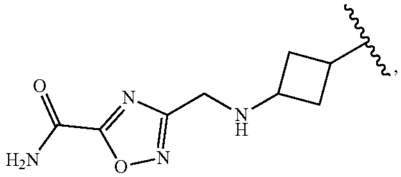, or
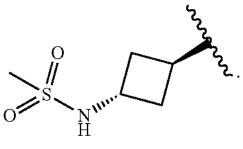.
In some embodiments of a compound of Formula (I), (Ia), (Ib), (II), (IIa), (IIb), (IIIa), (IIIb), (IIIc), or (IIId), $R^7$ is
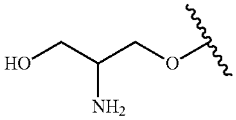,
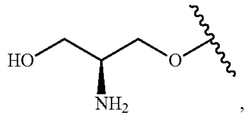, -continued

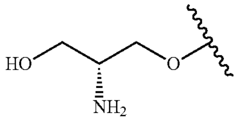,
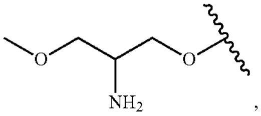,
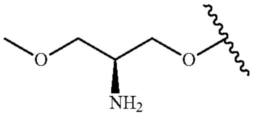,
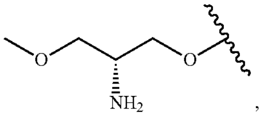,
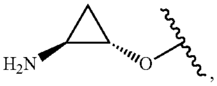,
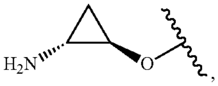,
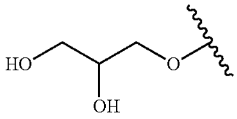,
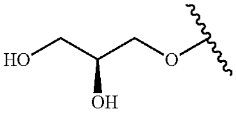,
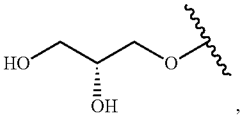,
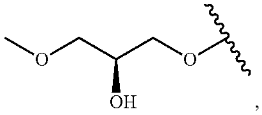,
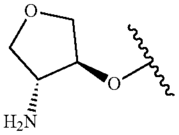,
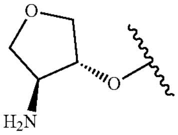,
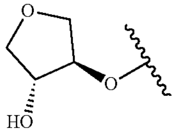,
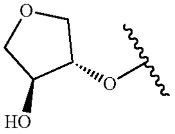,
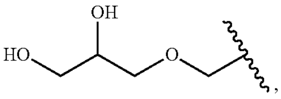,
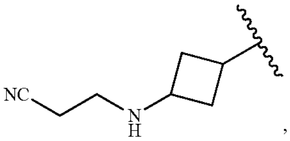,
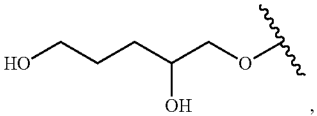,
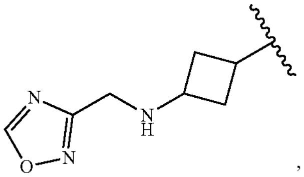,
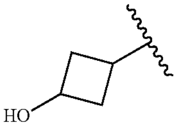,
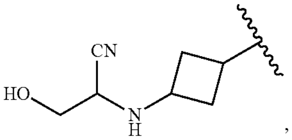, or
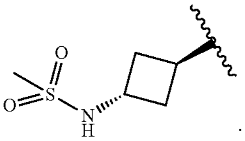.

In some embodiments of a compound of Formula (I), $R^1$ is —$CH_3$;

$R^{2a}$ and $R^{2b}$ are each hydrogen;

$R^3$ is hydrogen, —($C_1$-$C_4$ alkylene)-OH, or —($C_1$-$C_4$ alkylene)-$NH_2$;

$R^4$ is hydrogen;

each $R^5$ and $R^6$ is hydrogen;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ methoxyalkyl, and $C_1$-$C_4$ hydroxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH)$NH_2$, and monocyclic heteroaryl which is unsubstituted or substituted by 1 —$CONH_2$ group.

In some embodiments of a compound of Formula (I), $R^1$ is —$CH_3$;

$R^{2a}$ and $R^{2b}$ are each hydrogen;

$R^3$ is hydrogen, —($C_1$-$C_4$ alkylene)-OH, or —($C_1$-$C_4$ alkylene)-$NH_2$;

$R^4$ is hydrogen;

each $R^5$ and $R^6$ is hydrogen;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and monocyclic heteroaryl which is unsubstituted or substituted by 1 —$CONH_2$ group.

In some embodiments of a compound of Formula (I), $R^1$ is —$CH_3$;

$R^{2a}$ and $R^{2b}$ are each hydrogen;

$R^3$ is hydrogen or —($C_1$-$C_4$ alkylene)-OH;

$R^4$ is hydrogen;

each $R^5$ and $R^6$ is hydrogen;

$R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ hydroxyalkyl, and $C_1$-$C_4$ methoxyalkyl; and each $R^8$ is independently hydrogen, $C_1$-$C_4$ alkyl, —C(=O)—$C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(=NH)$NH_2$, and 5-membered monocyclic heteroaryl which is unsubstituted or substituted by 1 —$CONH_2$ group.

In some embodiments of a compound of Formula (I), $R^1$ is —$CH_3$;

$R^{2a}$ and $R^{2b}$ are each hydrogen;

$R^3$ is hydrogen or —($C_1$-$C_4$ alkylene)-OH;

$R^4$ is hydrogen;

each $R^5$ and $R^6$ is hydrogen;

$R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(=O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(=NH)$NH_2$, and 5-membered monocyclic heteroaryl which is unsubstituted or substituted by 1 —$CONH_2$ group.

In some embodiments of a compound of Formula (I), $R^1$ is —$CH_3$;

$R^{2a}$ and $R^{2b}$ are each hydrogen;

$R^3$ is hydrogen or —$CH_2OH$;

$R^4$ is hydrogen;

each $R^5$ and $R^6$ is hydrogen;

$R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, —$NHSO_2R^8$, and —$CH_2CN$; and each $R^8$ is independently hydrogen, $C_1$-$C_2$ alkyl, or —C(=O)—$C_1$-$C_2$ alkyl, wherein the alkyl is unsubstituted or substituted by 1 or 2 groups independently selected from —CN, —OH, and oxadiazolyl.

In some embodiments of a compound of Formula (I), $R^1$ is —$CH_3$;

$R^{2a}$ and $R^{2b}$ are each hydrogen;

$R^3$ is hydrogen or —$CH_2OH$;

$R^4$ is hydrogen;

each $R^5$ and $R^6$ is hydrogen;

$R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, and —$NHSO_2R^8$; and each $R^8$ is independently hydrogen or $C_1$-$C_2$ alkyl which is unsubstituted or substituted by 1 or 2 groups independently selected from —CN, —OH, and oxadiazolyl.

In some embodiments, the compound of Formula (I) is a compound of Formula (IV):

Formula (IV)

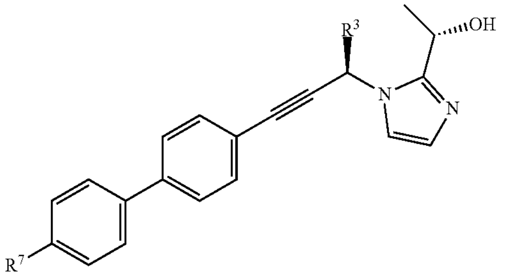

or a pharmaceutically acceptable salt, or solvate thereof.

In some embodiments, $R^3$ is hydrogen, —($C_1$-$C_4$ alkylene)-OH, or —($C_1$-$C_4$ alkylene)-$NH_2$;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(=O)—$C_1$-$C_4$ hydroxyalkyl, $C_1$-$C_4$ methoxyalkyl, and $C_1$-$C_4$ hydroxyalkyl; and each $R^8$ is independently hydrogen, $C_1$-$C_4$ alkyl, —C(=O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(=NH)$NH_2$, and monocyclic heteroaryl which is unsubstituted or substituted by 1 —$CONH_2$ group.

In some embodiments, $R^3$ is hydrogen, —($C_1$-$C_4$ alkylene)-OH, or —($C_1$-$C_4$ alkylene)-$NH_2$;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(=O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(=NH)$NH_2$, and monocyclic heteroaryl which is unsubstituted or substituted by 1 —$CONH_2$ group.

In some embodiments of a compound of Formula (IV), $R^3$ is hydrogen or —($C_1$-$C_4$ alkylene)-OH;

$R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ hydroxyalkyl, and $C_1$-$C_4$ methoxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group.

In some embodiments of a compound of Formula (IV), $R^3$ is hydrogen or —($C_1$-$C_4$ alkylene)-OH;

$R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, $C_1$-$C_4$ alkyl, —C(═O)—$C_1$-$C_4$ hydroxyalkyl, and $C_1$-$C_4$ hydroxyalkyl; and each $R^8$ is independently hydrogen, $C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH)$NH_2$, and 5-membered monocyclic heteroaryl which is unsubstituted or substituted by 1 —$CONH_2$ group.

In some embodiments of a compound of Formula (IV), $R^3$ is hydrogen or —$CH_2OH$;

$R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, —$NHSO_2R^8$, and —$CH_2CN$; and each $R^8$ is independently hydrogen, $C_1$-$C_2$ alkyl, or —C(═O)—$C_1$-$C_4$ alkyl, wherein the alkyl is unsubstituted or substituted by 1 or 2 groups selected from —CN, —OH, and oxadiazolyl.

In some embodiments of a compound of Formula (IV), $R^3$ is hydrogen or —$CH_2OH$;

$R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, and —$NHSO_2R^8$; and each $R^8$ is independently hydrogen or $C_1$-$C_2$ alkyl which is unsubstituted or substituted by 1 or 2 groups selected from —CN, —OH, and oxadiazolyl.

In some embodiments of a compound of Formula (IV), $R^7$ is

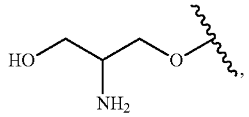
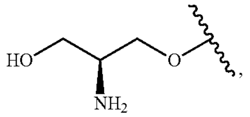
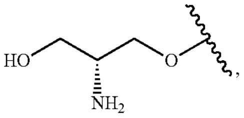
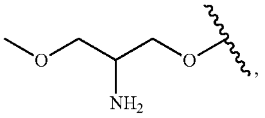

-continued

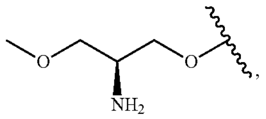
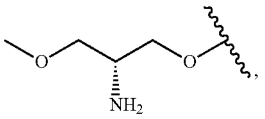
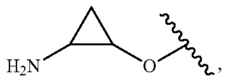
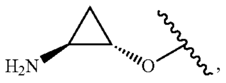
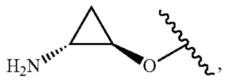
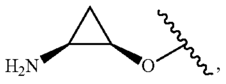
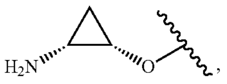
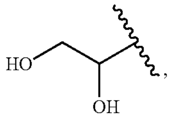
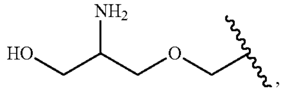
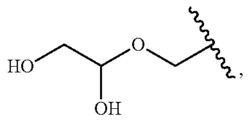
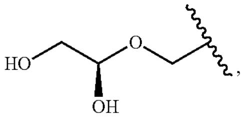
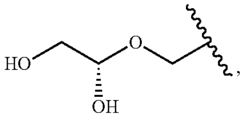
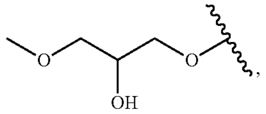
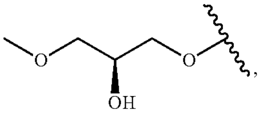
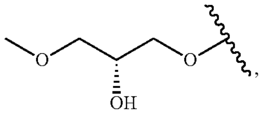
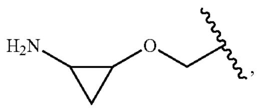
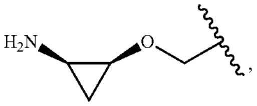
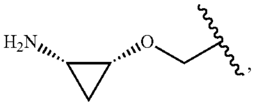
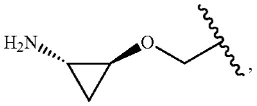
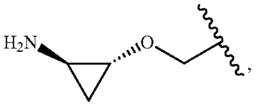
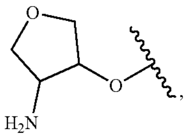
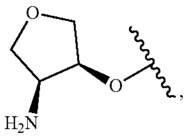
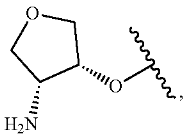
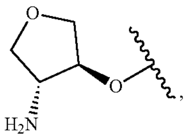
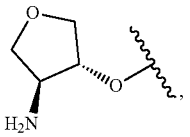
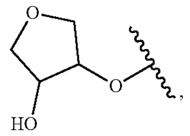
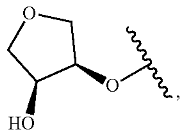
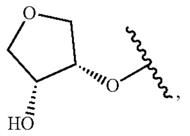

-continued
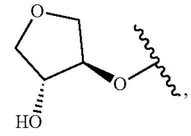,
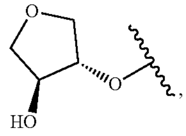,
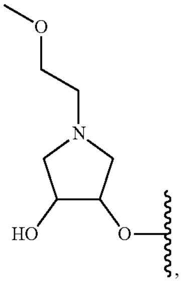,
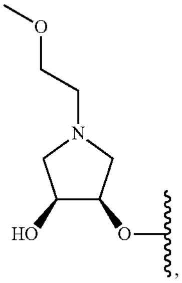,
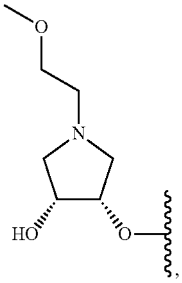,
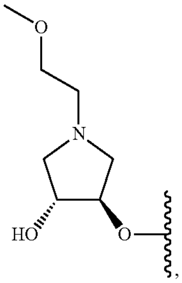,
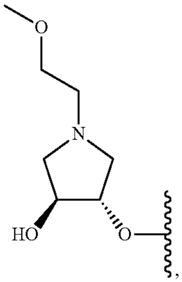,
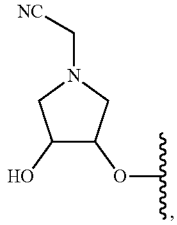,
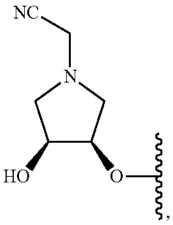,
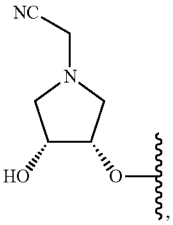,
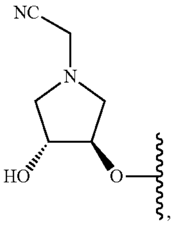,
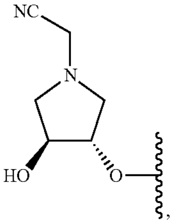,
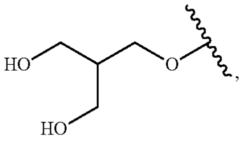,
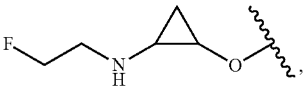,
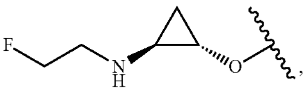,
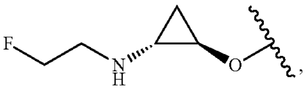,
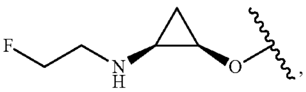,
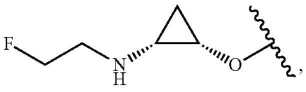,
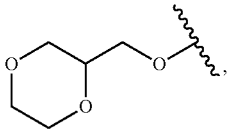,
-continued
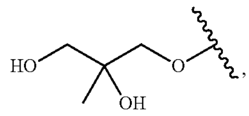,
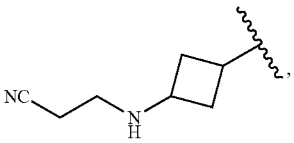,
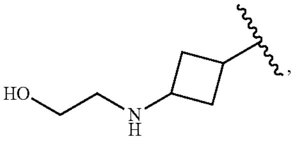,
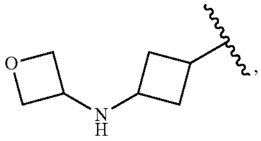,
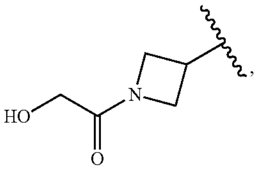,
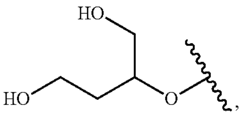,
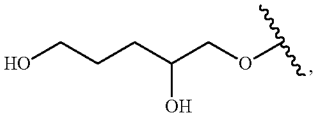,
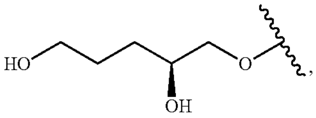,
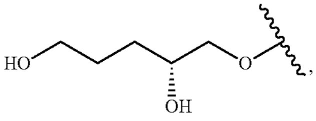,
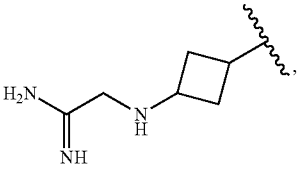,
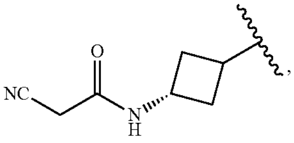,
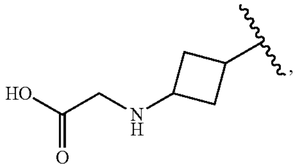,
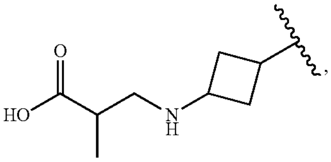,
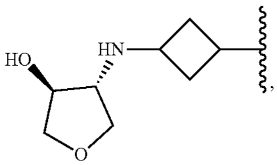, -continued
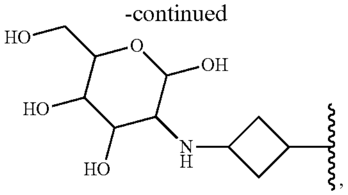,
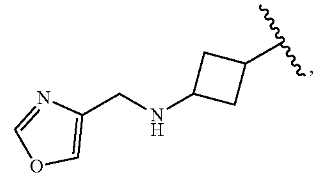, 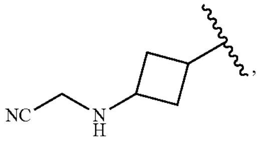,
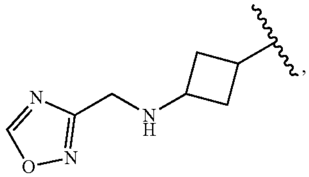, 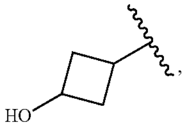,
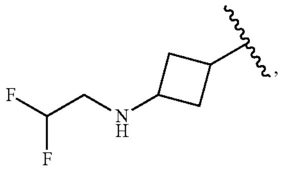, 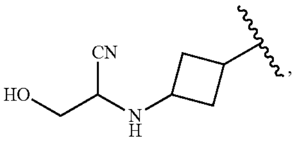,
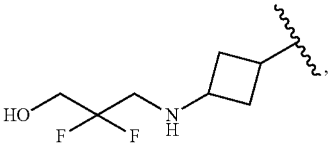,
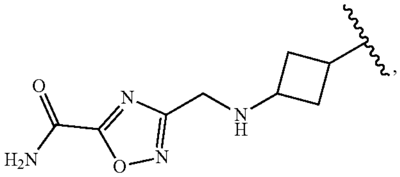, or
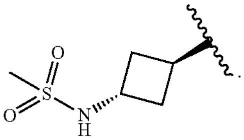.
In some embodiments of a compound of Formula (IV), $R^7$ is
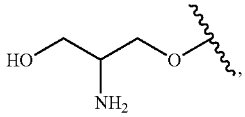, 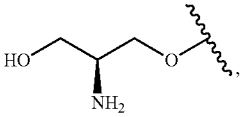,
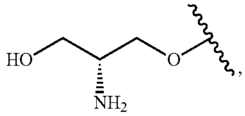, 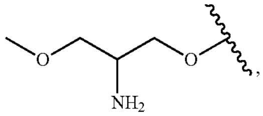,
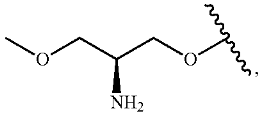, 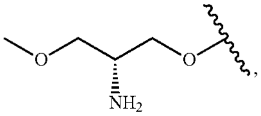,
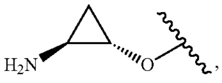, 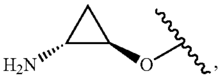,
-continued
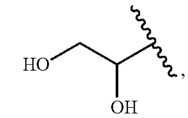, 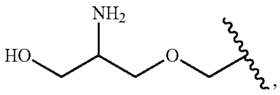,
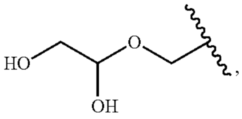, 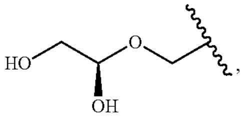,
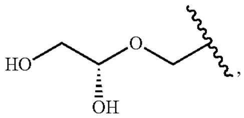, 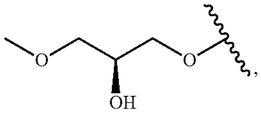,
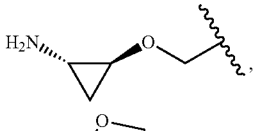, 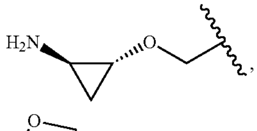,
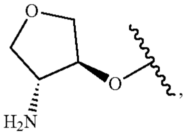, 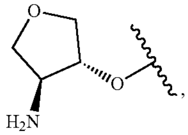,
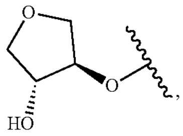, 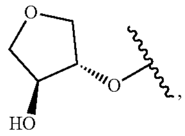,
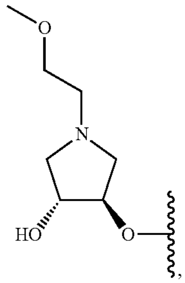, 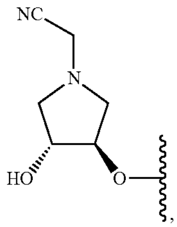,
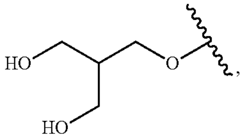, 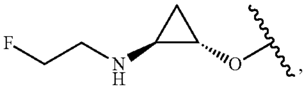,
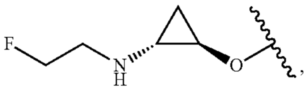,
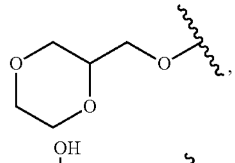, 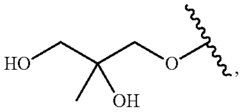,
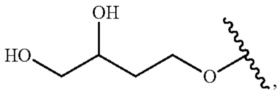, 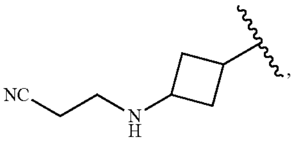,
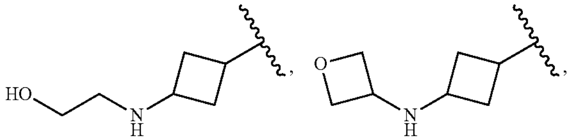, -continued
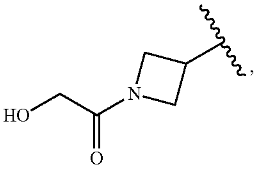, 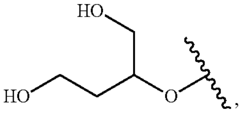,
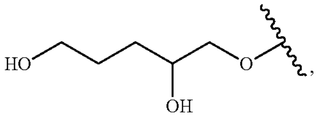,
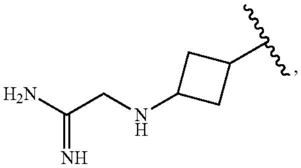,
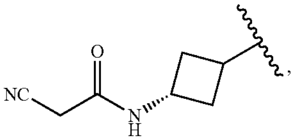,
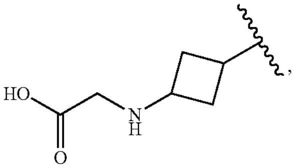,
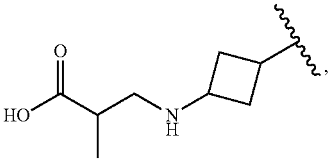,
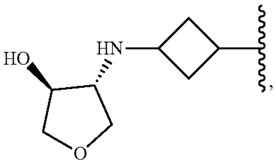,
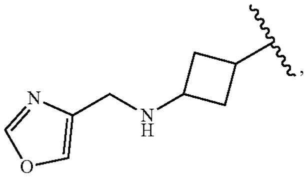, 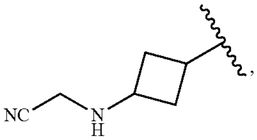,
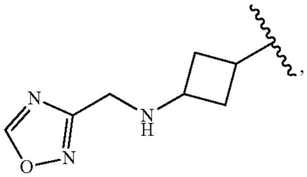, 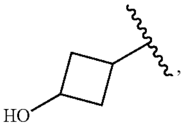,
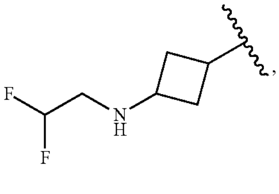, 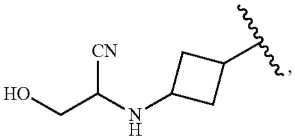,
-continued
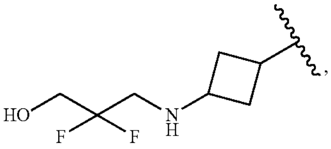,
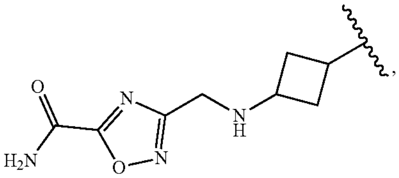, or
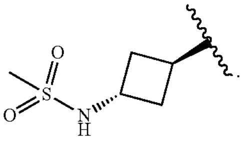.
In some embodiments of a compound of Formula (IV), $R^7$ is
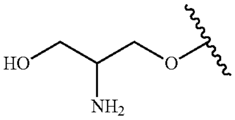, 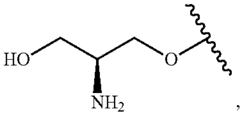,
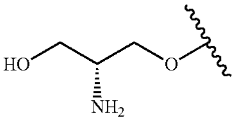, 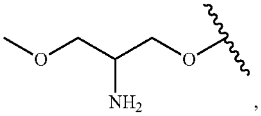,
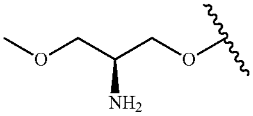, 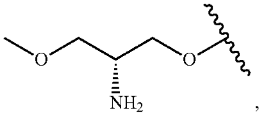,
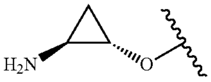, 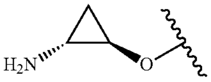,
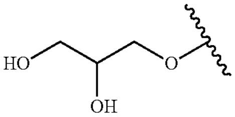, 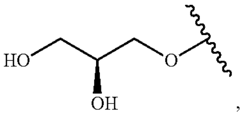,
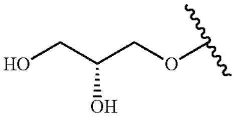, 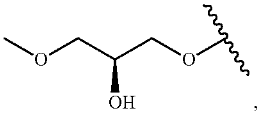,
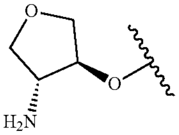, 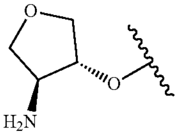,
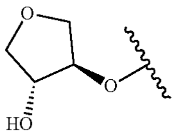, 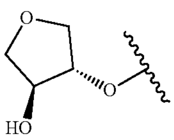, -continued
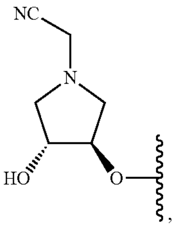,
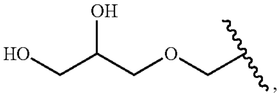,
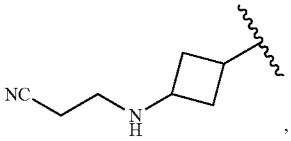,
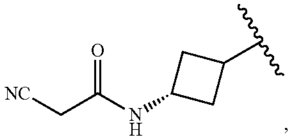,
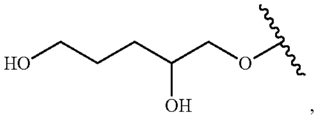,
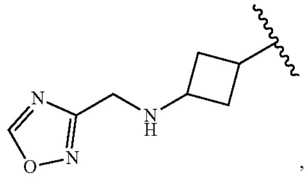,
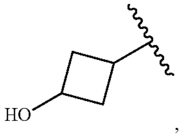,
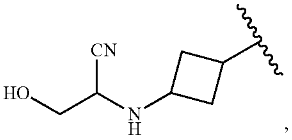, or
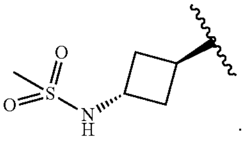.
some embodiments of a compound of Formula (IV), $R^7$ is
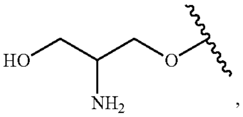,
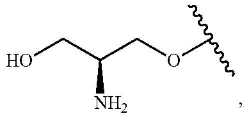,
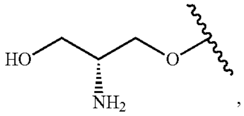,
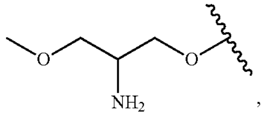,
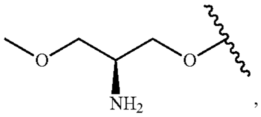,
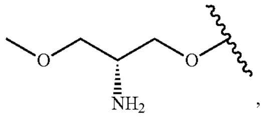,
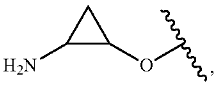,
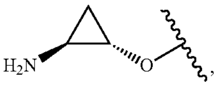,
-continued
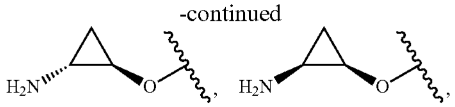,
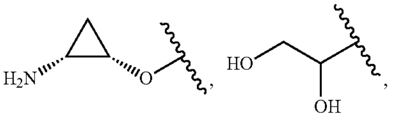,
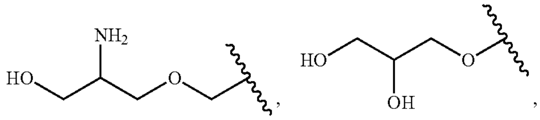,
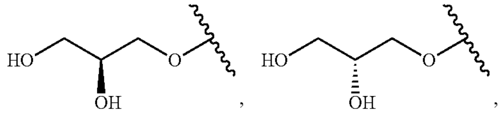,
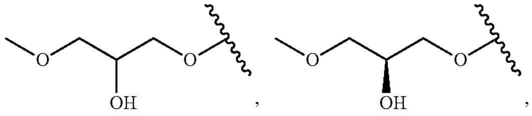,
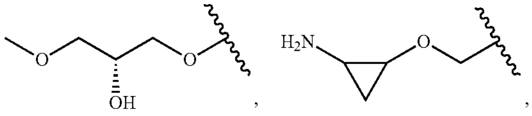,
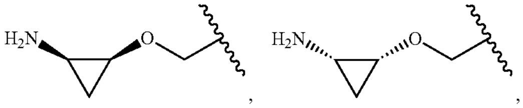,
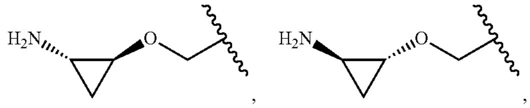,
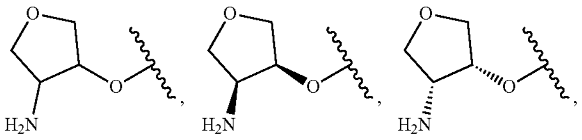,
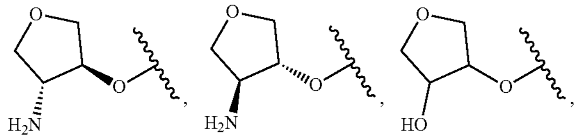,
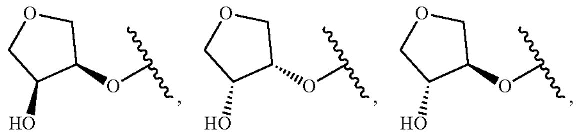,
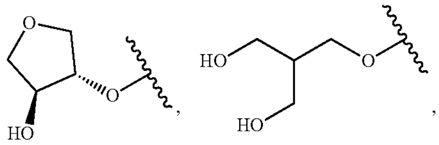,
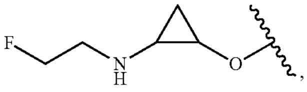,
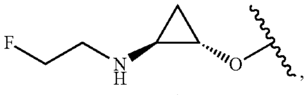,
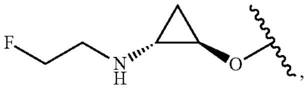, -continued
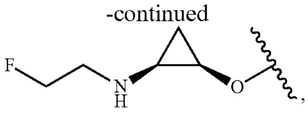,
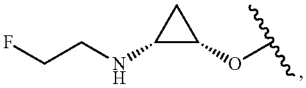, 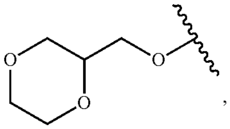,
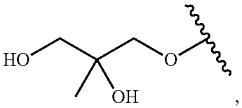, 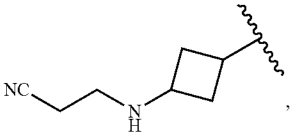,
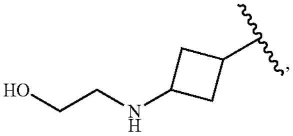, 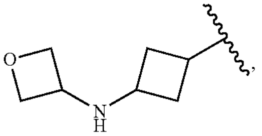,
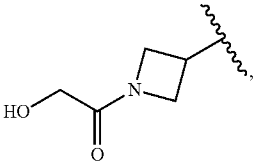, 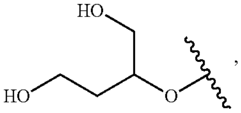,
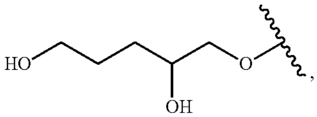,
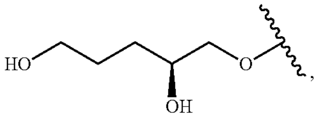,
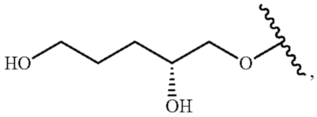,
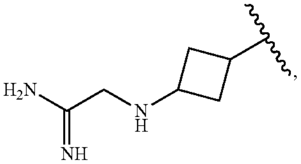,
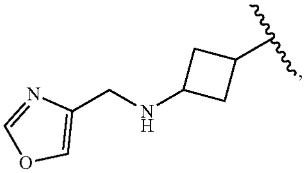, 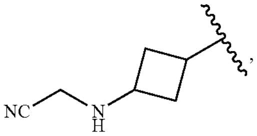,
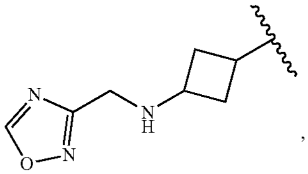, 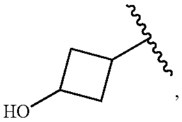,
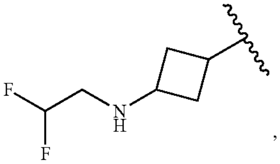,
-continued
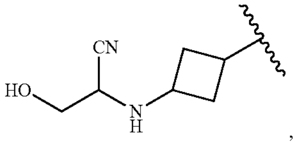,
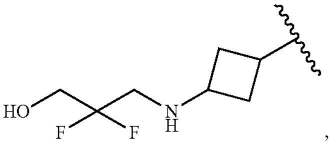,
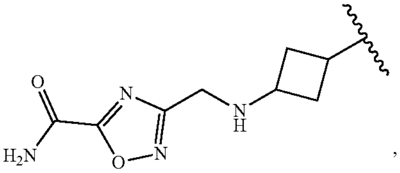, or
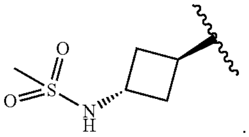.
In some embodiments of a compound of Formula (IV), $R^8$ is
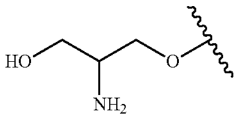, 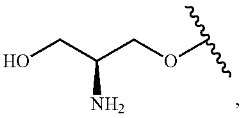,
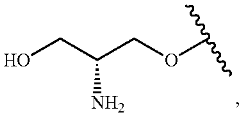, 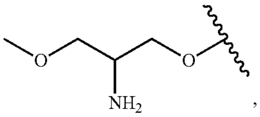,
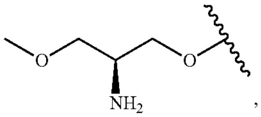, 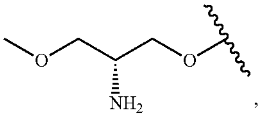,
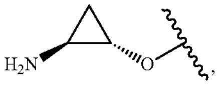, 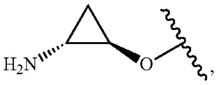,
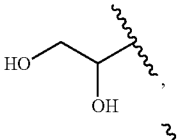, 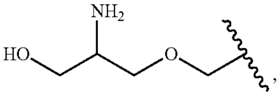,
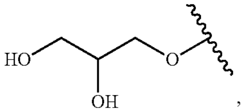, 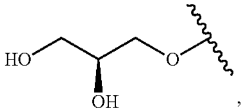,
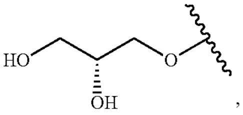, 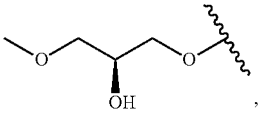,
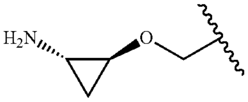, 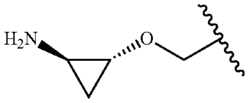, -continued
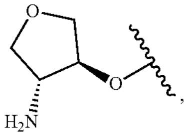, 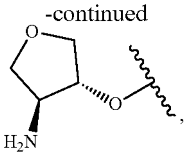, 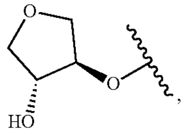,
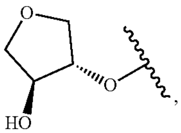, 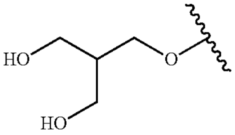,
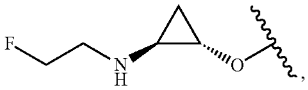,
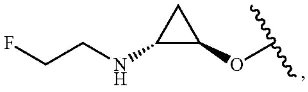, 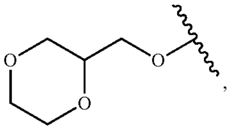,
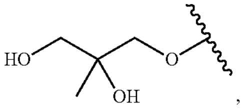, 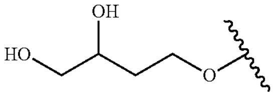,
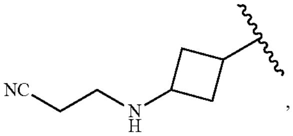,
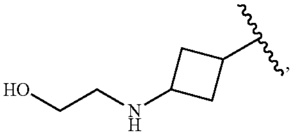, 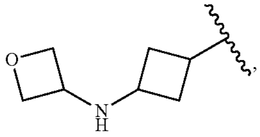,
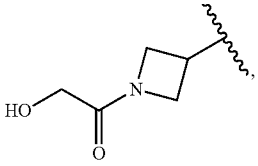, 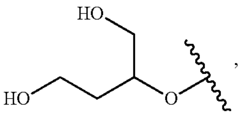,
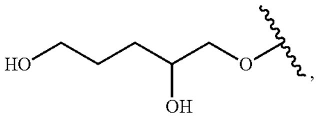,
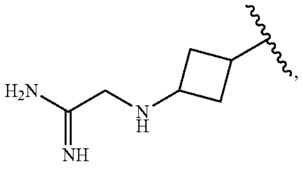,
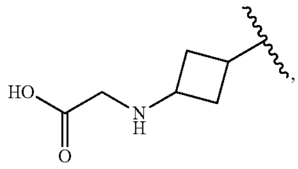,
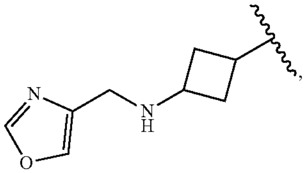, 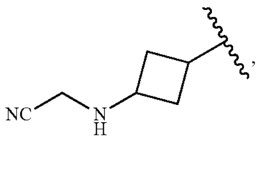,
-continued
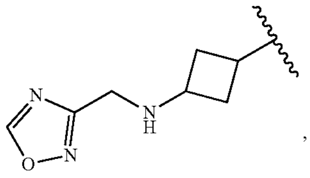, 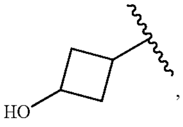,
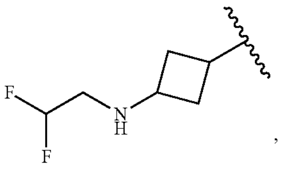,
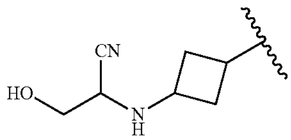,
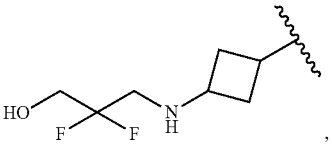,
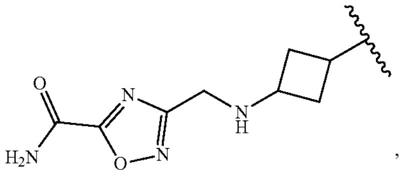, or
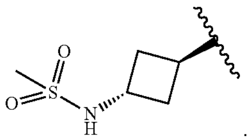.
In some embodiments of a compound of Formula (IV), $R^7$ is
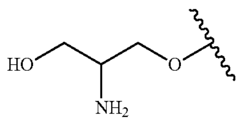, 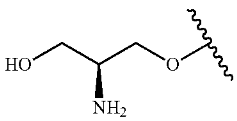,
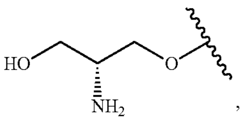, 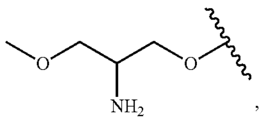,
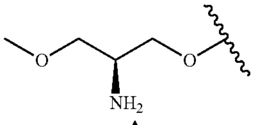, 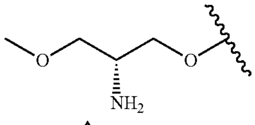,
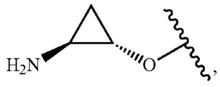, 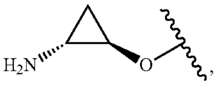,
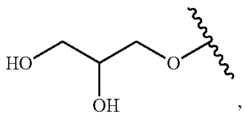, 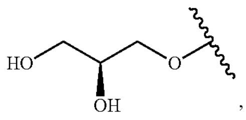, -continued
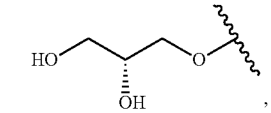, 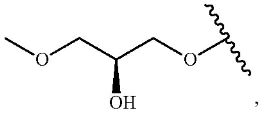,
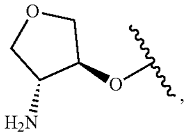, 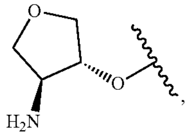, 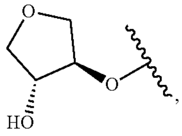,
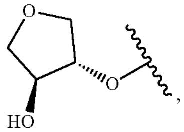, 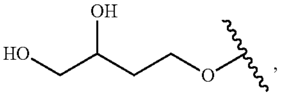,
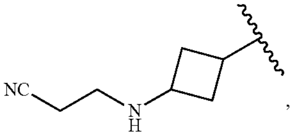,
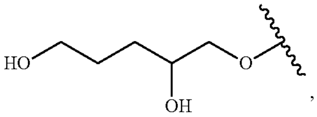,
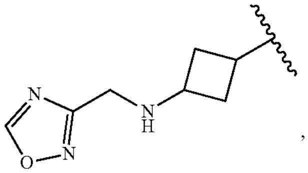, 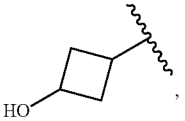,
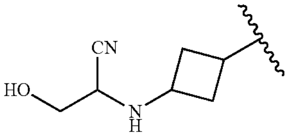, or
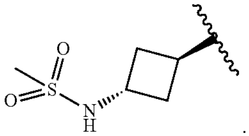.
In some embodiments, compounds described herein have the following structure:
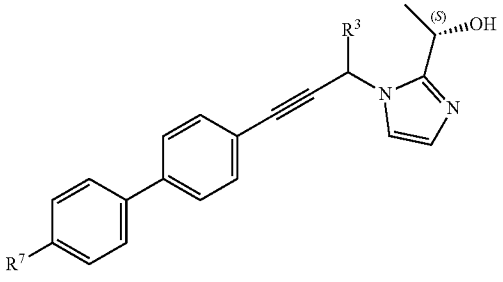
wherein $R^3$ and $R^7$ are as described in Table 1.
In some embodiments, $R^3$ is hydrogen $CH_2OH$ or $CH_2NH_2$.
In some embodiments, $R^7$ is
(rac)- 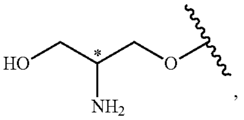, 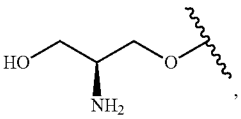,
(rac)- 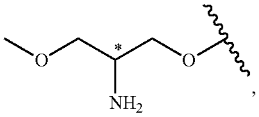,
(rac)- 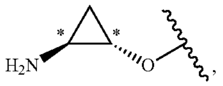, (rac)- 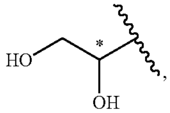,
(rac)- 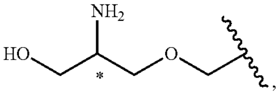,
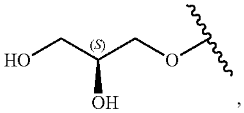, (rac)- 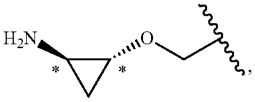,
(rac)- 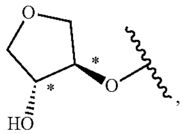, (rac)- 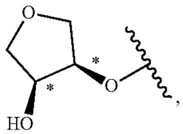,
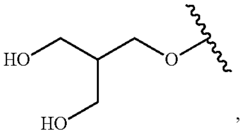,
(rac)- 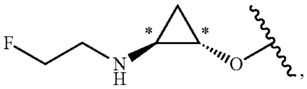,
(rac)- 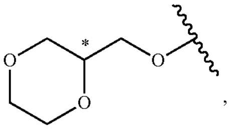, 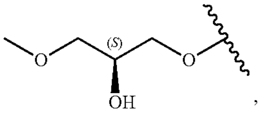,
(rac)- 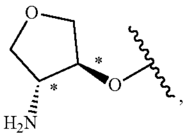, (rac)- 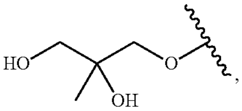,
(rac)- 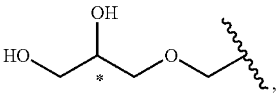,
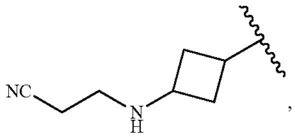,
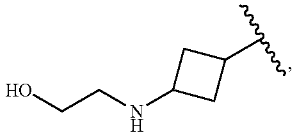, 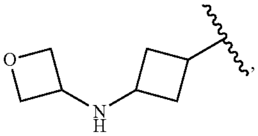, -continued
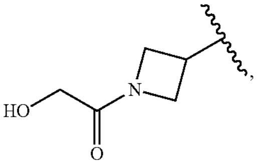, (rac)- 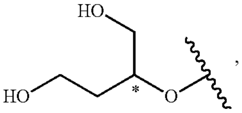,
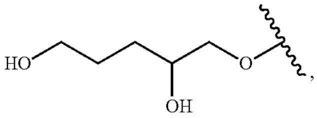,
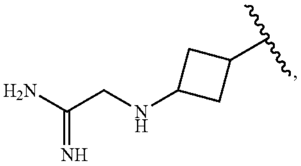,
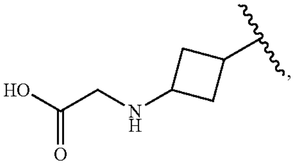,
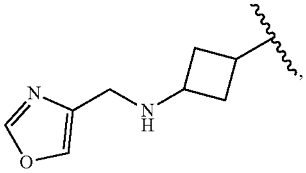, 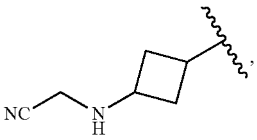,
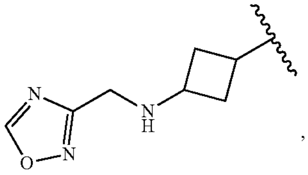, 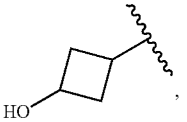,
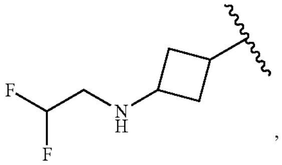, 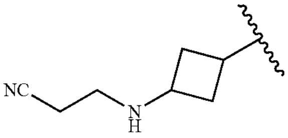,
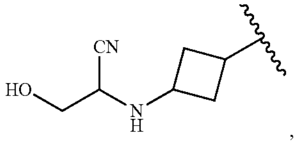,
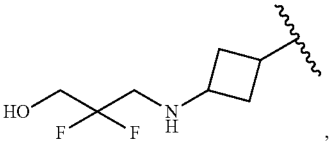,
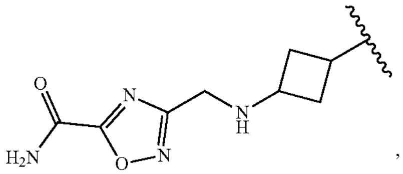,
-continued
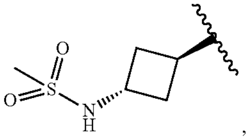,
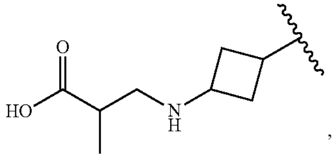,
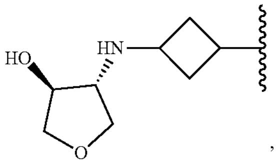,
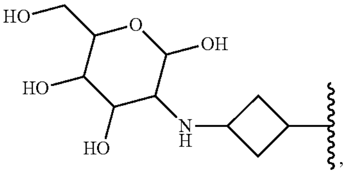,
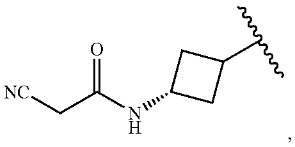, 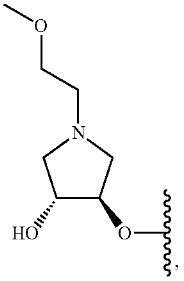, or
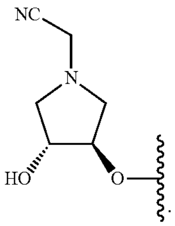.
In some embodiments, $R^7$ is
(rac)- 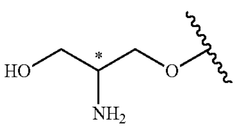, 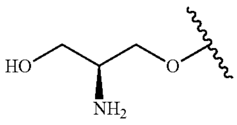,
(rac)- 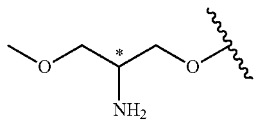,
(rac)- 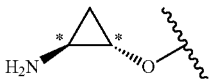, (rac)- 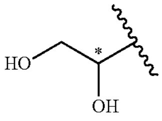,
(rac)- 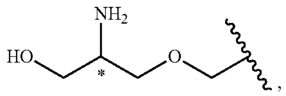, -continued
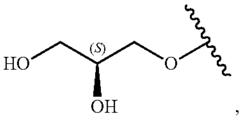
, (rac)-
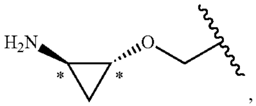
,
(rac)-
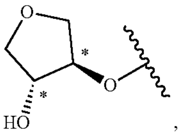
,
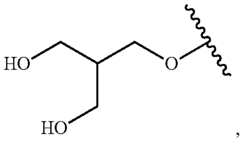
,
(rac)-
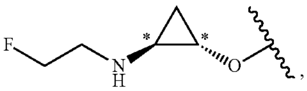
,
(rac)-
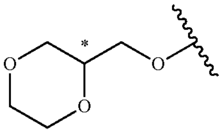
,
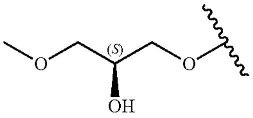
,
(rac)-
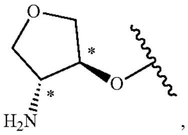
, (rac)-
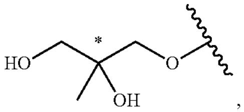
,
(rac)-
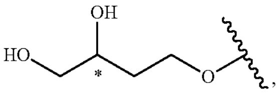
,
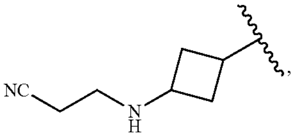
,
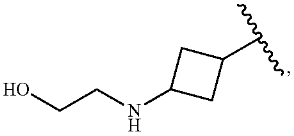
,
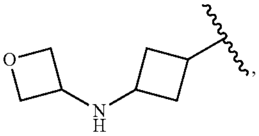
,
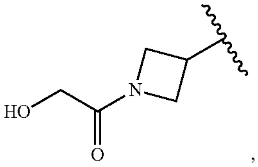
, (rac)-
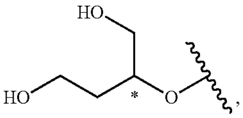
,
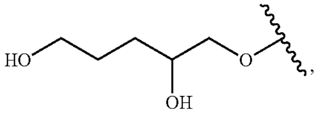
,
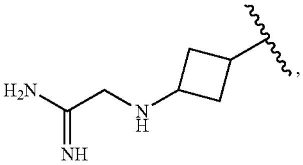
,
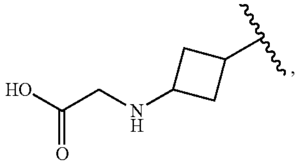
,
-continued
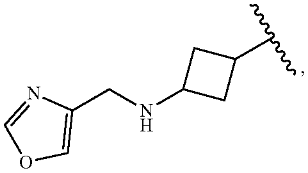
,
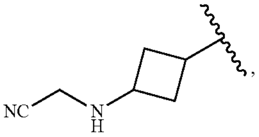
,
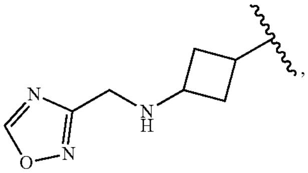
,
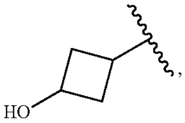
,
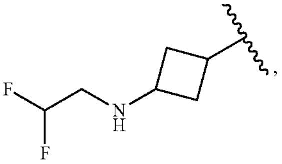
,
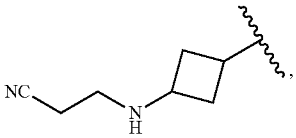
,
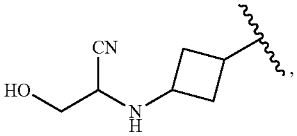
,
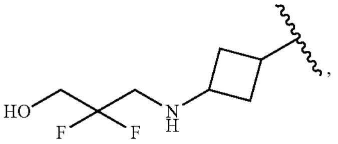
,
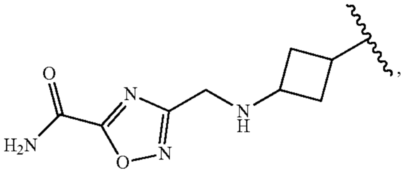
, or
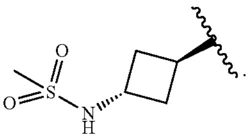
.
Any combination of the groups described above for the various variables is contemplated herein. Throughout the specification, groups and substituents thereof are chosen by one skilled in the field to provide stable moieties and compounds.

Exemplary compounds described herein include the compounds described in the following Tables:
TABLE 1
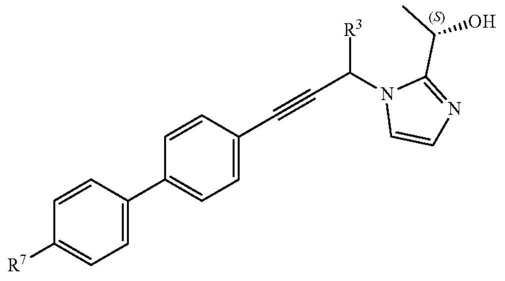
| Compound No. | $R^7$ | 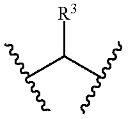 |
|---|---|---|
| 1 | 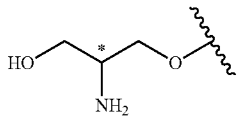 * racemic | 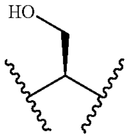 |
| 2 | 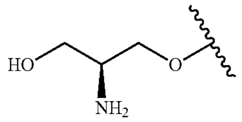 | 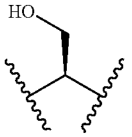 |
| 3 | 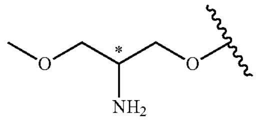 * racemic | 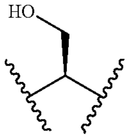 |
| 4 | 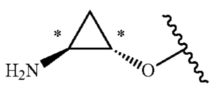 [SMILES: *O[C@H]1C[C@@H]1N] *racemic-trans | 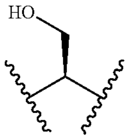 |
| 5 | 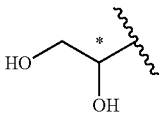 * racemic | 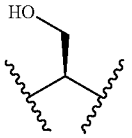 |
| 6 | 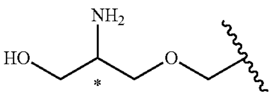 [SMILES: *COCC(N)CO] * racemic | 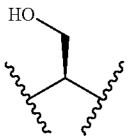 |
TABLE 1-continued
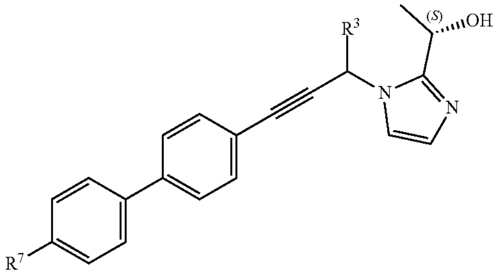
| Compound No. | $R^7$ | 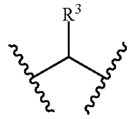 |
|---|---|---|
| 7 | 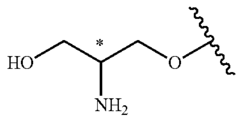 * racemic | 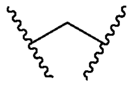 [SMILES: *C*] |
| 8 | 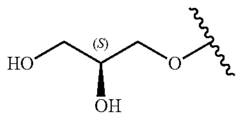 | 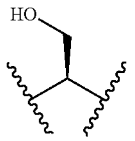 |
| 9 | 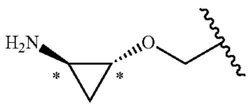 [SMILES: *CO[C@@H]1C[C@H]1N] *racemic-trans | 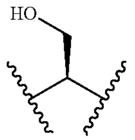 |
| 10 | 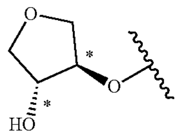 [SMILES: *O[C@@H]1COC[C@H]1O] *racemic-trans | 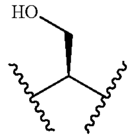 |
| 11 | 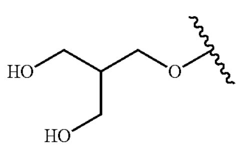 [SMILES: *OCC(CO)CO] | 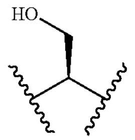 |
| 12 | 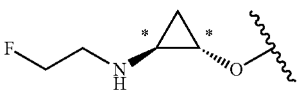 [SMILES: *O[C@H]1C[C@@H]1NCCF] *racemic-trans | 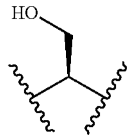 |

TABLE 1-continued
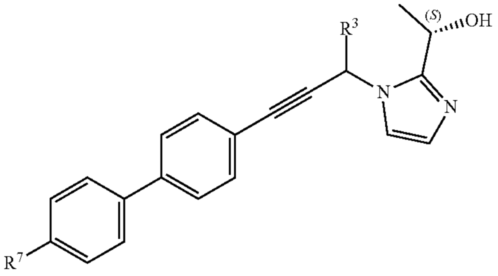
| Compound No. | $R^7$ | 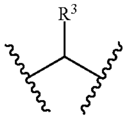 |
|---|---|---|
| 13 | 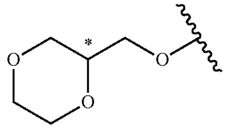 [SMILES: *OCC1COCCO1]<br>* racemic | 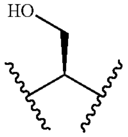 |
| 14 | 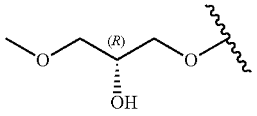 | 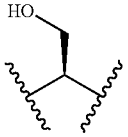 |
| 15 | 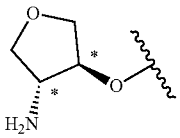 [SMILES: *O[C@@H]1COC[C@H]1N]<br>*racemic-trans | 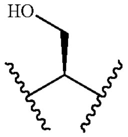 |
| 16 | 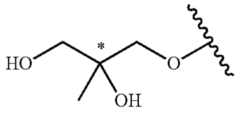 [SMILES: *OCC(C)(O)CO]<br>* racemic | 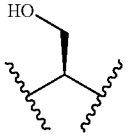 |
| 17 | 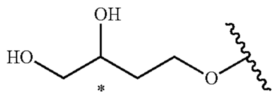 [SMILES: *OCCC(O)CO]<br>* racemic | 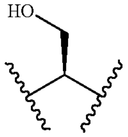 |
| 18 | 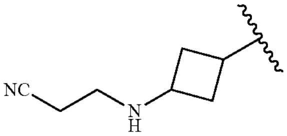 [SMILES: *C1CC(NCCC#N)C1] | 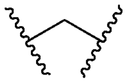 |
| 19 | 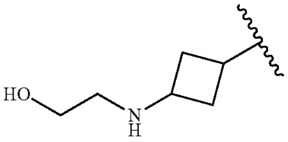 | 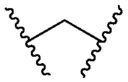 [SMILES: *C*] |
TABLE 1-continued
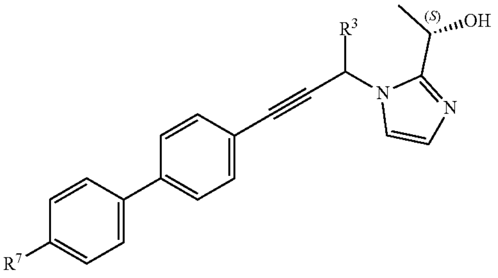
| Compound No. | $R^7$ | 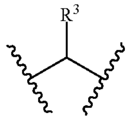 |
|---|---|---|
| 20 | 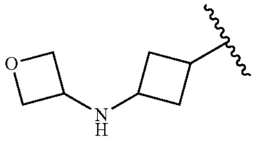 [SMILES: *C1CC(NC2COC2)C1] | 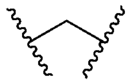 |
| 21 | 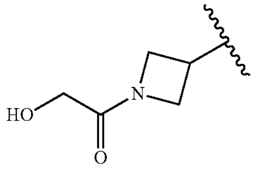 [SMILES: *C1CN(C(=O)CO)C1] | 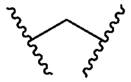 |
| 22 | 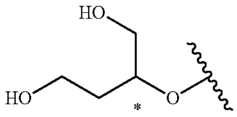<br>* racemic | 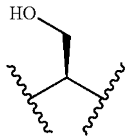 |
| 23 | 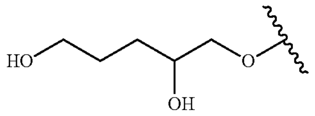 [SMILES: *OCC(O)CCCO] | 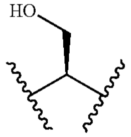 |
| 24 | 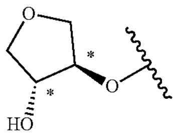 [SMILES: *O[C@@H]1COC[C@H]1O]<br>*racemic-trans | 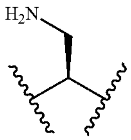 |
| 25 | 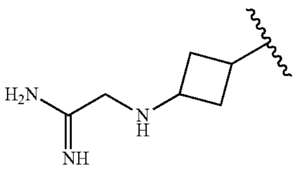 [SMILES: *C1CC(NCC(=N)N)C1] | 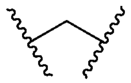 [SMILES: *C*] |

TABLE 1-continued
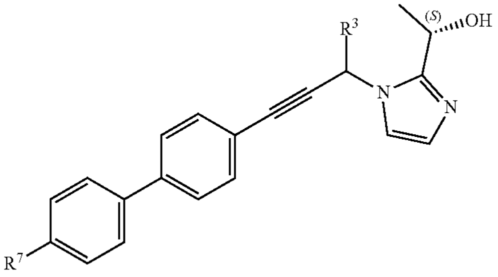
| Compound No. | $R^7$ | 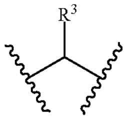 |
|---|---|---|
| 26 | 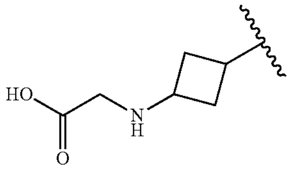 [SMILES: *C1CC(NCC(=O)O)C1] | 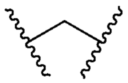 [SMILES: *C*] |
| 27 | 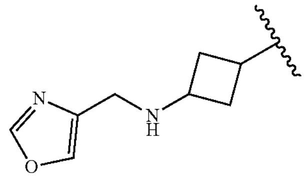 [SMILES: *C1CC(NCc2cocn2)C1] | 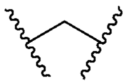 |
| 28 | 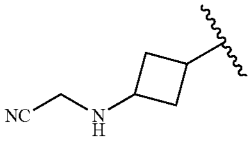 [SMILES: *C1CC(NCC#N)C1] | 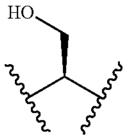 |
| 29 | 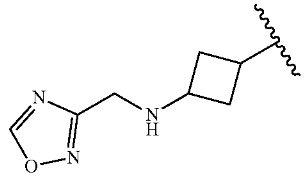 [SMILES: *C1CC(NCc2ncon2)C1] | 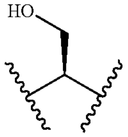 |
| 30 | 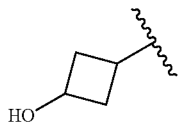 | 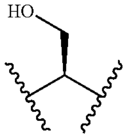 |
| 31 | 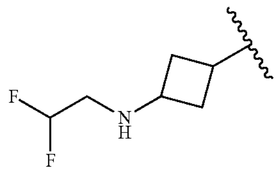 [SMILES: *C1CC(NCC(F)F)C1] | 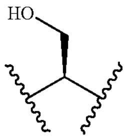 |
TABLE 1-continued
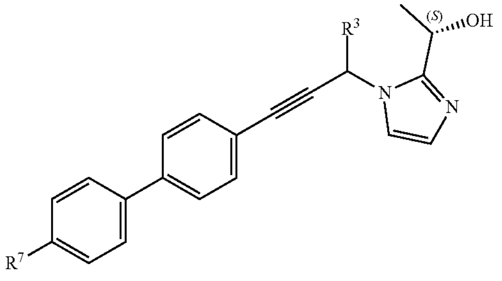
| Compound No. | $R^7$ | 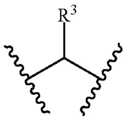 |
|---|---|---|
| 32 | 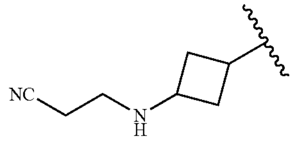 [SMILES: *C1CC(NCCC#N)C1] | 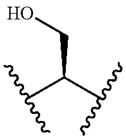 |
| 33 | 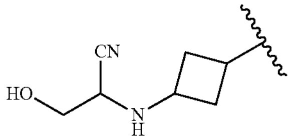 [SMILES: *C1CC(NC(C#N)CO)C1] | 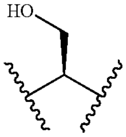 |
| 34 | 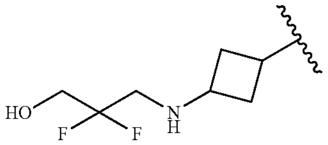 [SMILES: *C1CC(NCC(F)(F)CO)C1] | 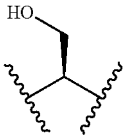 |
| 35 | 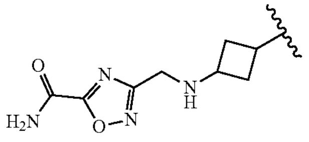 [SMILES: *C1CC(NCc2noc(C(N)=O)n2)C1] | 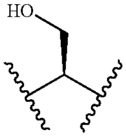 |
| 36 | 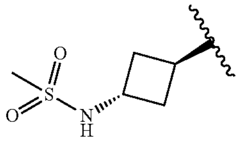 [SMILES: *[C@H]1C[C@H](NS(C)(=O)=O)C1] | 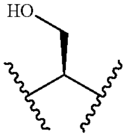 |
| 37 | 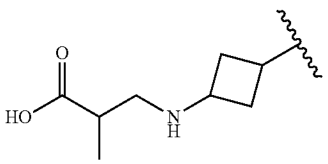 [SMILES: *C1CC(NCC(C)C(=O)O)C1] | 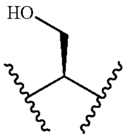 |

TABLE 1-continued
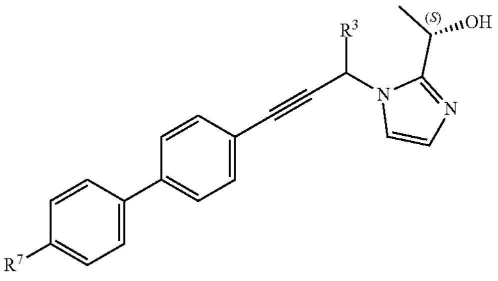
| Compound No. | $R^7$ | 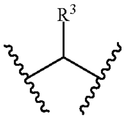 |
|---|---|---|
| 38 | 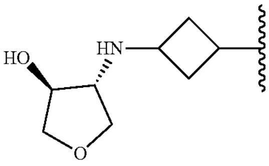 [SMILES: *C1CC(N[C@@H]2COC[C@H]2O)C1] | 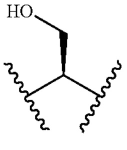 |
| 39 | 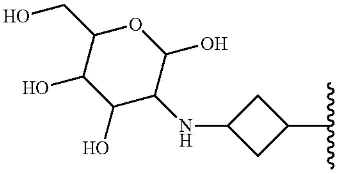 [SMILES: *C1CC(NC2C(O)OC(CO)C(O)C2O)C1] | 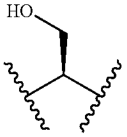 |
| 40 | 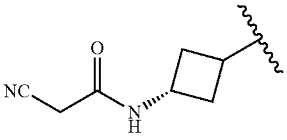 | 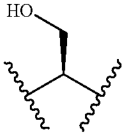 |
| 41 | 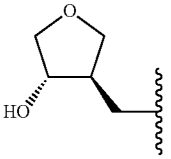 [SMILES: *C[C@@H]1COC[C@H]1O] | 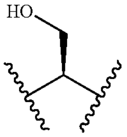 |
| 42 | 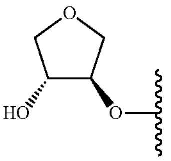 [SMILES: *O[C@@H]1COC[C@H]1O] | 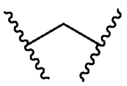 [SMILES: *C*] |
TABLE 1-continued
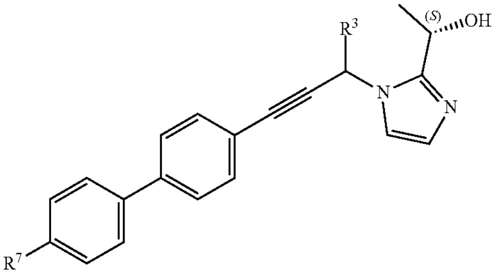
| Compound No. | $R^7$ | 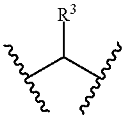 |
|---|---|---|
| 43 | 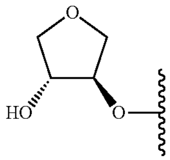 [SMILES: *O[C@@H]1COC[C@H]1O] | 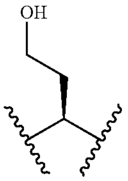 |
| 44 | 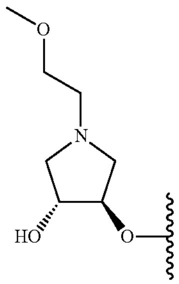 [SMILES: *O[C@@H]1CN(CCOC)C[C@H]1O] | 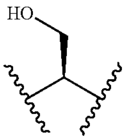 |
| 45 | 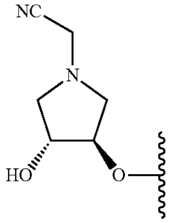 [SMILES: *O[C@@H]1CN(CC#N)C[C@H]1O] | 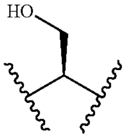 |
| 46 | 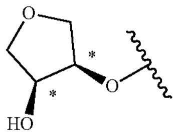 [SMILES: *O[C@@H]1COC[C@@H]1O] | 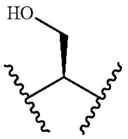 |
*racemic-cis
In some embodiments, the compound is a compound of Table 1, or a pharmaceutically acceptable salt, or solvate thereof. In some embodiments, the compound is a diastereomer of a compound of Table 1, or a pharmaceutically acceptable salt, or solvate thereof.

Structures and names of the compounds of Table 1 are found in Table 1a:

TABLE 1a

| Cpd | Structure | Name |
|---|---|---|
| 1 | 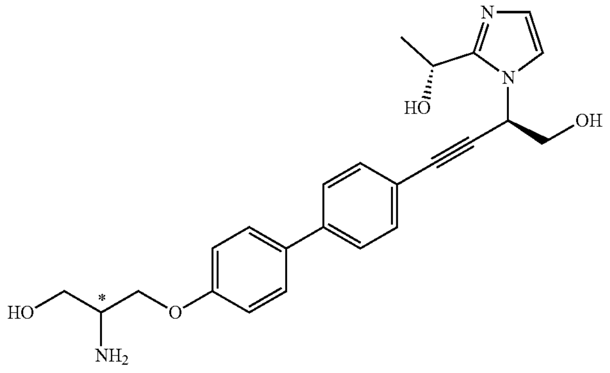 [SMILES: C[C@@H](O)c1nccn1[C@H](C#Cc1ccc(-c2ccc(OCC(N)CO)cc2)cc1)CO] * racemic | (2R)-4-(4'-(2-amino-3-hydroxypropoxy)-[1,1'-biphenyl]-4-yl)-2-(2-((R)-1-hydroxyethyl)-1H-imidazol-1-yl)but-3-yn-1-ol |
| 2 | 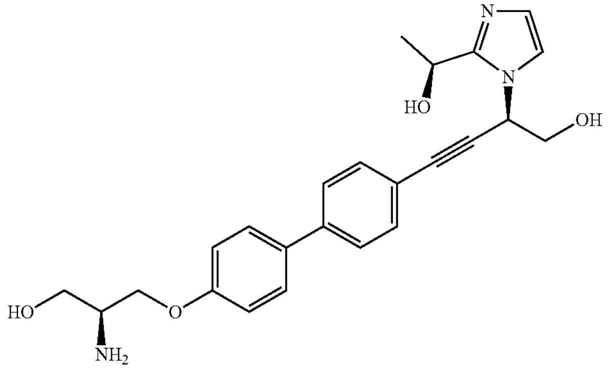 [SMILES: C[C@H](O)c1nccn1[C@H](C#Cc1ccc(-c2ccc(OC[C@@H](N)CO)cc2)cc1)CO] | (R)-4-(4'-((S)-2-amino-3-hydroxypropoxy)-[1,1'-biphenyl]-4-yl)-2-(2-((S)-1-hydroxyethyl)-1H-imidazol-1-yl)but-3-yn-1-ol |
| 3 | 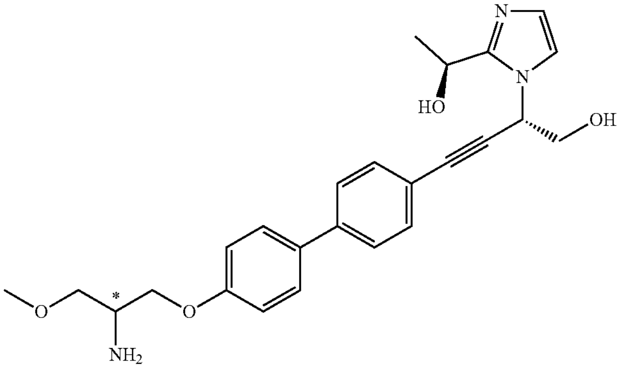 [SMILES: COCC(N)COc1ccc(-c2ccc(C#C[C@@H](CO)n3ccnc3[C@H](C)O)cc2)cc1] * racemic | (2S)-4-(4'-(2-amino-3-methoxypropoxy)-[1,1'-biphenyl]-4-yl)-2-(2-((S)-1-hydroxyethyl)-1H-imidazol-1-yl)but-3-yn-1-ol |
| 4 | 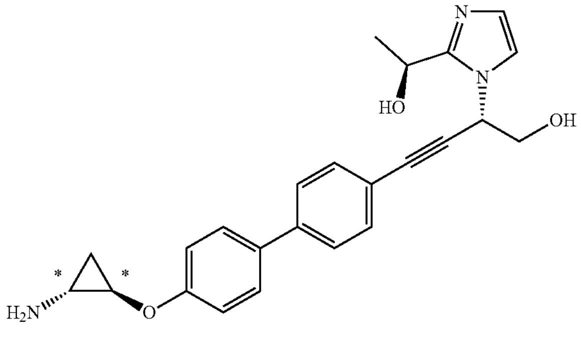 [SMILES: C[C@H](O)c1nccn1[C@@H](C#Cc1ccc(-c2ccc(O[C@@H]3C[C@H]3N)cc2)cc1)CO] | (S)-4-(4'-((trans)-2-aminocyclopropoxy)-[1,1'-biphenyl]-4-yl)-2-(2-((S)-1-hydroxyethyl)-1H-imidazol-1-yl)but-3-yn-1-ol |

TABLE 1a-continued

| Cpd | Structure | Name |
|---|---|---|
| | *racemic-trans | |
| 5 | 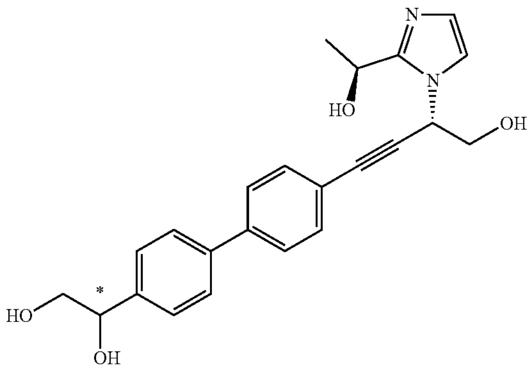 [SMILES: C[C@H](O)c1nccn1[C@@H](C#Cc1ccc(-c2ccc(C(O)CO)cc2)cc1)CO] | 1-(4'-((S)-4-hydroxy-3-(2-((S)-1-hydroxyethyl)-1H-imidazol-1-yl)but-1-yn-1-yl)-[1,1'-biphenyl]-4-yl)ethane-1,2-diol |
| | * racemic | |
| 6 | 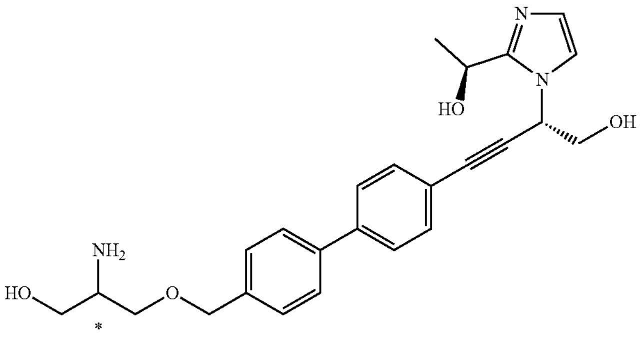 [SMILES: C[C@H](O)c1nccn1[C@@H](C#Cc1ccc(-c2ccc(COCC(N)CO)cc2)cc1)CO] | (2S)-4-(4'-((2-amino-3-hydroxypropoxy)methyl)-[1,1'-biphenyl]-4-yl)-2-(2-((S)-1-hydroxyethyl)-1H-imidazol-1-yl)but-3-yn-1-ol |
| | * racemic | |
| 7 | 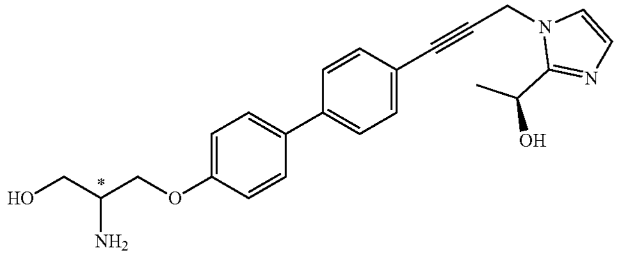 [SMILES: C[C@H](O)c1nccn1CC#Cc1ccc(-c2ccc(OCC(N)CO)cc2)cc1] | 2-amino-3-((4'-(3-(2-((S)-1-hydroxyethyl)-1H-imidazol-1-yl)prop-1-yn-1-yl)-[1,1'-biphenyl]-4-yl)oxy)propan-1-ol |
| | * racemic | |
| 8 | 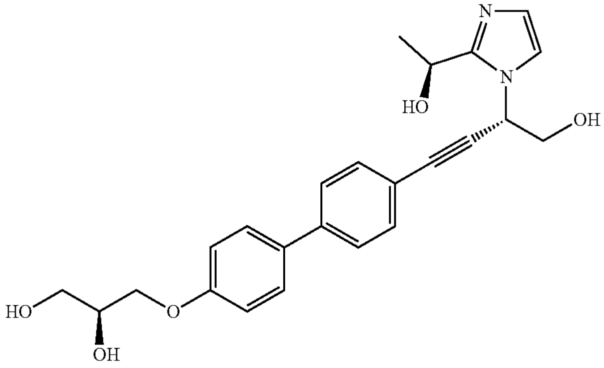 [SMILES: C[C@H](O)c1nccn1[C@@H](C#Cc1ccc(-c2ccc(OC[C@@H](O)CO)cc2)cc1)CO] | (S)-3-((4'-((S)-4-hydroxy-3-(2-((S)-1-hydroxyethyl)-1H-imidazol-1-yl)but-1-yn-1-yl)-[1,1'-biphenyl]-4-yl)oxy)propane-1,2-diol |

TABLE 1a-continued

| Cpd | Structure | Name |
| --- | --- | --- |
| 9 | 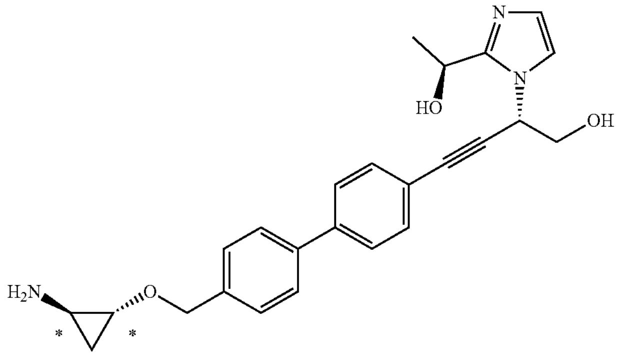 [SMILES: C[C@H](O)c1nccn1[C@@H](C#Cc1ccc(-c2ccc(CO[C@@H]3C[C@H]3N)cc2)cc1)CO]<br>*racemic-trans | (S)-4-(4'-(((trans)-2-aminocyclopropoxy)methyl)-[1,1'-biphenyl]-4-yl)-2-(2-((S)-1-hydroxyethyl)-1H-imidazol-1-yl)but-3-yn-1-ol |
| 10 | 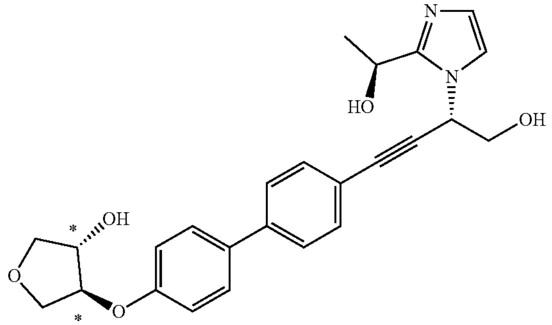 [SMILES: C[C@H](O)c1nccn1[C@@H](C#Cc1ccc(-c2ccc(O[C@H]3COC[C@@H]3O)cc2)cc1)CO]<br>*racemic-trans | (trans)-4-((4'-((S)-4-hydroxy-3-(2-((S)-1-hydroxyethyl)-1H-imidazol-1-yl)but-1-yn-1-yl)-[1,1'-biphenyl]-4-yl)oxy)tetrahydrofuran-3-ol |
| 11 | 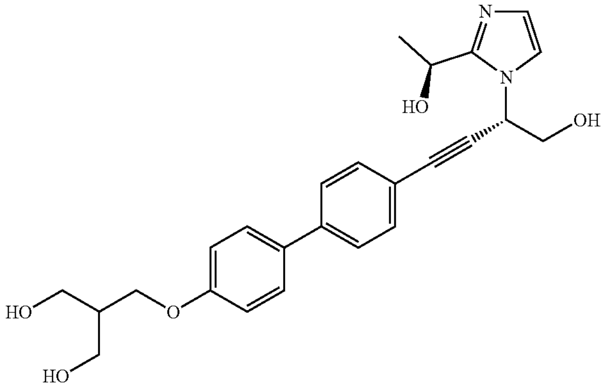 [SMILES: C[C@H](O)c1nccn1[C@@H](C#Cc1ccc(-c2ccc(OCC(CO)CO)cc2)cc1)CO] | 2-(((4'-((S)-4-hydroxy-3-(2-((S)-1-hydroxyethyl)-1H-imidazol-1-yl)but-1-yn-1-yl)-[1,1'-biphenyl]-4-yl)oxy)methyl)propane-1,3-diol |
| 12 | 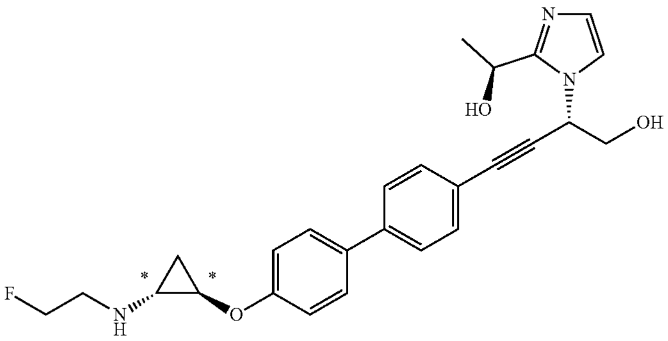 [SMILES: C[C@H](O)c1nccn1[C@@H](C#Cc1ccc(-c2ccc(O[C@@H]3C[C@H]3NCCF)cc2)cc1)CO]<br>*racemic-trans | (S)-4-(4'-((trans)-2-((2-fluoroethyl)amino)cyclopropoxy)-[1,1'-biphenyl]-4-yl)-2-(2-((S)-1-hydroxyethyl)-1H-imidazol-1-yl)but-3-yn-1-ol |

TABLE 1a-continued

| Cpd | Structure | Name |
| --- | --- | --- |
| 13 | 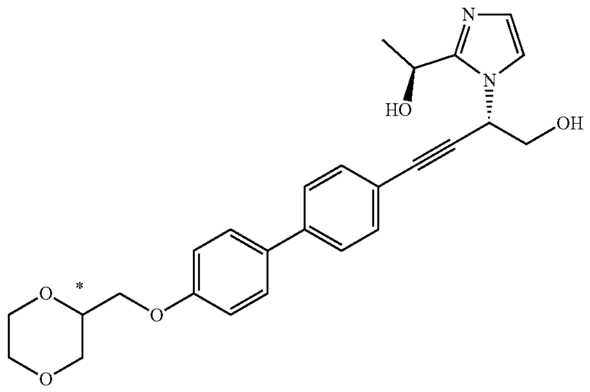 [SMILES: C[C@H](O)c1nccn1[C@@H](C#Cc1ccc(-c2ccc(OCC3COCCO3)cc2)cc1)CO] * racemic | (2S)-4-(4'-((1,4-dioxan-2-yl)methoxy)-[1,1'-biphenyl]-4-yl)-2-(2-((S)-1-hydroxyethyl)-1H-imidazol-1-yl)but-3-yn-1-ol |
| 14 | 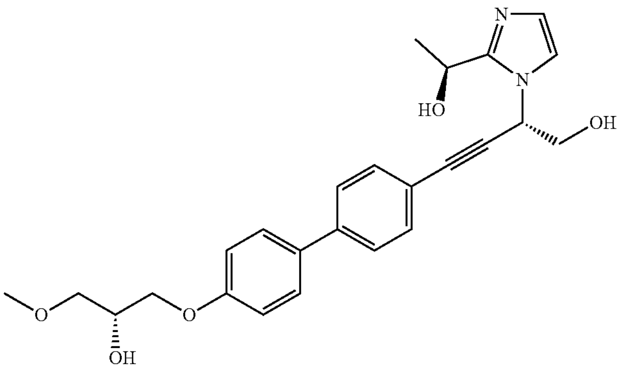 [SMILES: COC[C@@H](O)COc1ccc(-c2ccc(C#C[C@@H](CO)n3ccnc3[C@H](C)O)cc2)cc1] | (S)-4-(4'-((R)-2-hydroxy-3-methoxypropoxy)-[1,1'-biphenyl]-4-yl)-2-(2-((S)-1-hydroxyethyl)-1H-imidazol-1-yl)but-3-yn-1-ol |
| 15 | 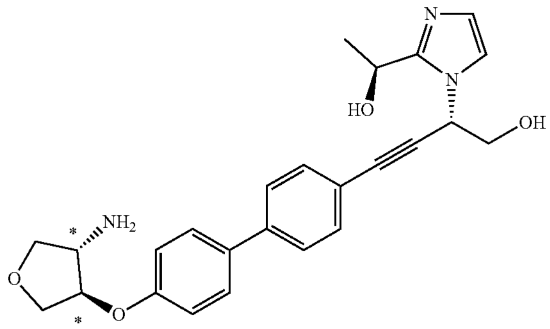 [SMILES: C[C@H](O)c1nccn1[C@@H](C#Cc1ccc(-c2ccc(O[C@H]3COC[C@@H]3N)cc2)cc1)CO] *racemic-trans | (S)-4-(4'-(((trans)-4-aminotetrahydrofuran-3-yl)oxy)-[1,1'-biphenyl]-4-yl)-2-(2-((S)-1-hydroxyethyl)-1H-imidazol-1-yl)but-3-yn-1-ol |
| 16 | 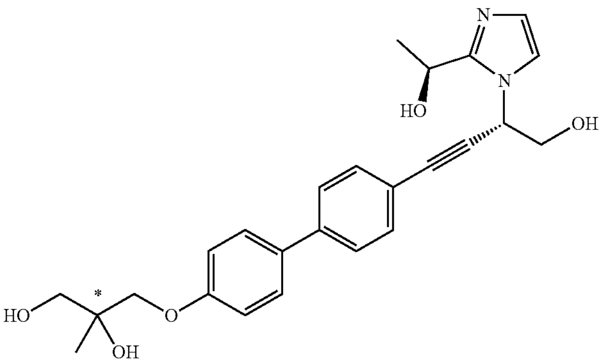 [SMILES: C[C@H](O)c1nccn1[C@@H](C#Cc1ccc(-c2ccc(OCC(C)(O)CO)cc2)cc1)CO] * racemic | 3-((4'-((S)-4-hydroxy-3-(2-((S)-1-hydroxyethyl)-1H-imidazol-1-yl)but-1-yn-1-yl)-[1,1'-biphenyl]-4-yl)oxy)-2-methylpropane-1,2-diol |

TABLE 1a-continued

| Cpd | Structure | Name |
|---|---|---|
| 17 | 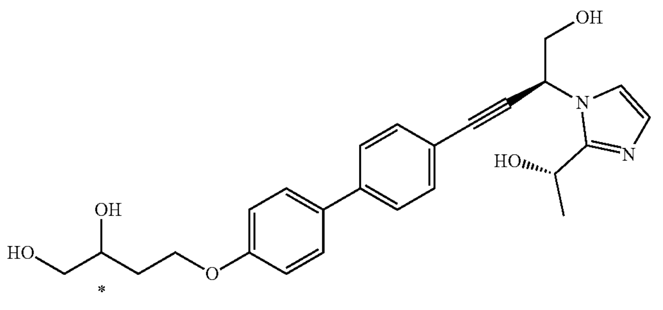 [SMILES: C[C@H](O)c1nccn1[C@@H](C#Cc1ccc(-c2ccc(OCCC(O)CO)cc2)cc1)CO] * racemic | 4-((4'-((S)-4-hydroxy-3-(2-((S)-1-hydroxyethyl)-1H-imidazol-1-yl)but-1-yn-1-yl)-[1,1'-biphenyl]-4-yl)oxy)butane-1,2-diol |
| 18 | 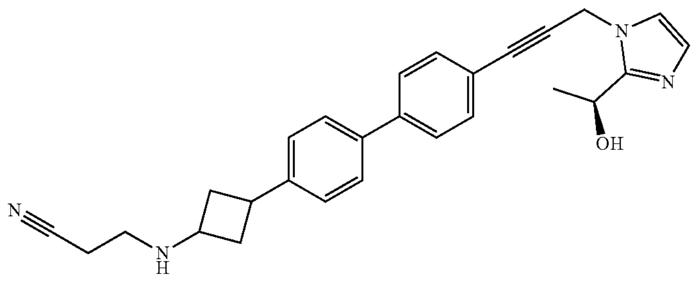 [SMILES: C[C@H](O)c1nccn1CC#Cc1ccc(-c2ccc(C3CC(NCCC#N)C3)cc2)cc1] | (S)-3-((3-(4'-(3-(2-(1-hydroxyethyl)-1H-imidazol-1-yl)prop-1-yn-1-yl)-[1,1'-biphenyl]-4-yl)cyclobutyl)amino)propanenitrile |
| 19 | 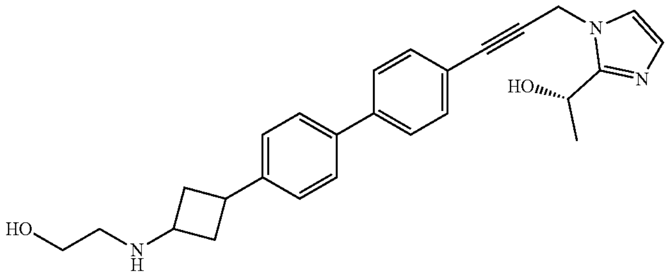 [SMILES: C[C@H](O)c1nccn1CC#Cc1ccc(-c2ccc(C3CC(NCCO)C3)cc2)cc1] | (S)-2-((3-(4'-(3-(2-(1-hydroxyethyl)-1H-imidazol-1-yl)prop-1-yn-1-yl)-[1,1'-biphenyl]-4-yl)cyclobutyl)amino)ethan-1-ol |
| 20 | 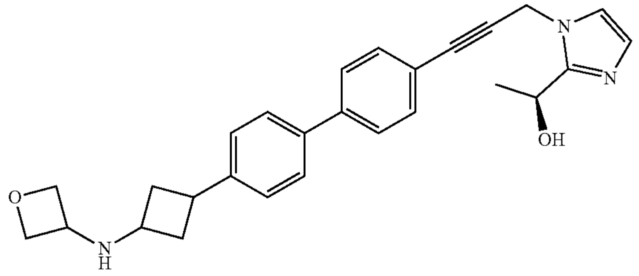 [SMILES: C[C@H](O)c1nccn1CC#Cc1ccc(-c2ccc(C3CC(NC4COC4)C3)cc2)cc1] | (S)-1-(1-(3-(4'-(3-(oxetan-3-ylamino)cyclobutyl)-[1,1'-biphenyl]-4-yl)prop-2-yn-1-yl)-1H-imidazol-2-yl)ethan-1-ol |
| 21 | 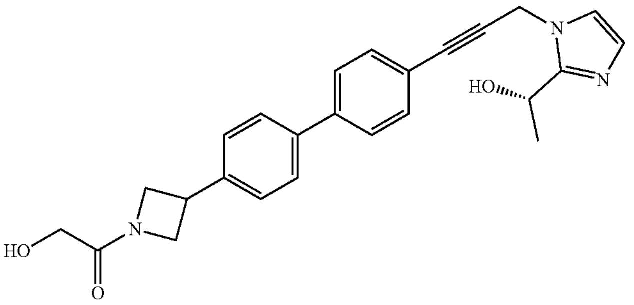 [SMILES: C[C@H](O)c1nccn1CC#Cc1ccc(-c2ccc(C3CN(C(=O)CO)C3)cc2)cc1] | (S)-2-hydroxy-1-(3-(4'-(3-(2-(1-hydroxyethyl)-1H-imidazol-1-yl)prop-1-yn-1-yl)-[1,1'-biphenyl]-4-yl)azetidin-1-yl)ethan-1-one |

TABLE 1a-continued

| Cpd | Structure | Name |
|---|---|---|
| 22 | 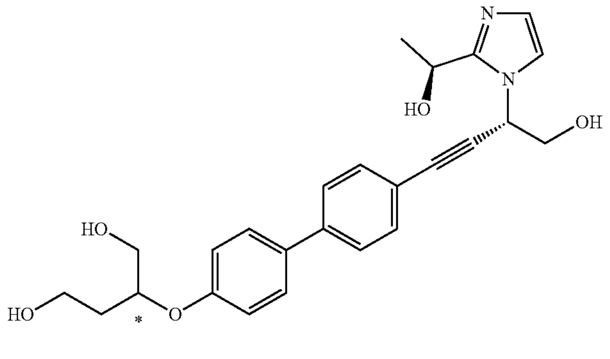 [SMILES: C[C@H](O)c1nccn1[C@@H](C#Cc1ccc(-c2ccc(OC(CO)CCO)cc2)cc1)CO] * racemic | 2-((4'-((S)-4-hydroxy-3-(2-((S)-1-hydroxyethyl)-1H-imidazol-1-yl)but-1-yn-1-yl)-[1,1'-biphenyl]-4-yl)oxy)butane-1,4-diol |
| 23 | 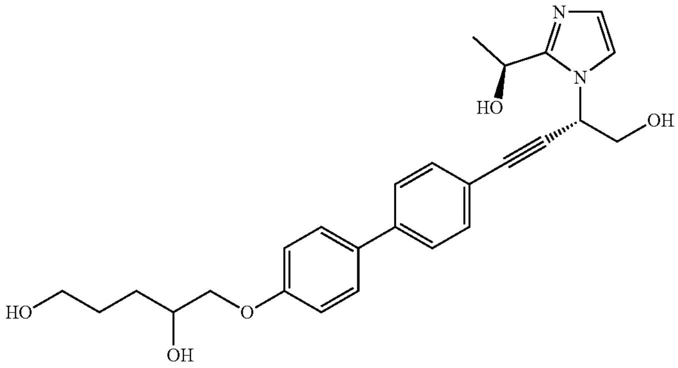 [SMILES: C[C@H](O)c1nccn1[C@@H](C#Cc1ccc(-c2ccc(OCC(O)CCCO)cc2)cc1)CO] | 5-((4'-((S)-4-hydroxy-3-(2-((S)-1-hydroxyethyl)-1H-imidazol-1-yl)but-1-yn-1-yl)-[1,1'-biphenyl]-4-yl)oxy)pentane-1,4-diol |
| 24 | 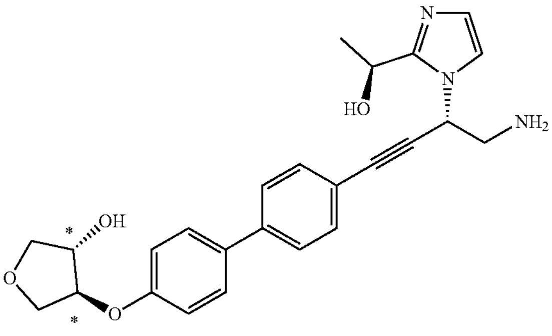 [SMILES: C[C@H](O)c1nccn1[C@@H](C#Cc1ccc(-c2ccc(O[C@H]3COC[C@@H]3O)cc2)cc1)CN] *racemic-trans | (trans)-4-((4'-((S)-4-amino-3-(2-((S)-1-hydroxyethyl)-1H-imidazol-1-yl)but-1-yn-1-yl)-[1,1'-biphenyl]-4-yl)oxy)tetrahydrofuran-3-ol |
| 25 | 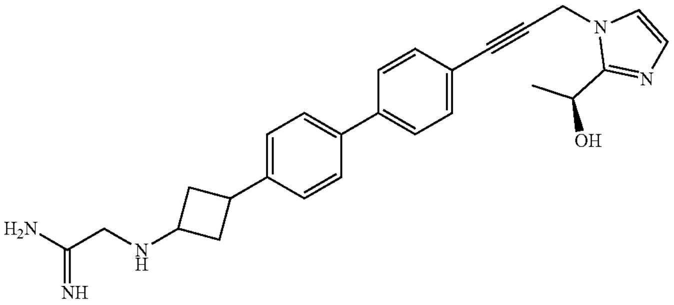 [SMILES: C[C@H](O)c1nccn1CC#Cc1ccc(-c2ccc(C3CC(NCC(=N)N)C3)cc2)cc1] | (S)-2-((3-(4'-(3-(2-(1-hydroxyethyl)-1H-imidazol-1-yl)prop-1-yn-1-yl)-[1,1'-biphenyl]-4-yl)cyclobutyl)amino)acetimidamide |

TABLE 1a-continued

| Cpd | Structure | Name |
|---|---|---|
| 26 | 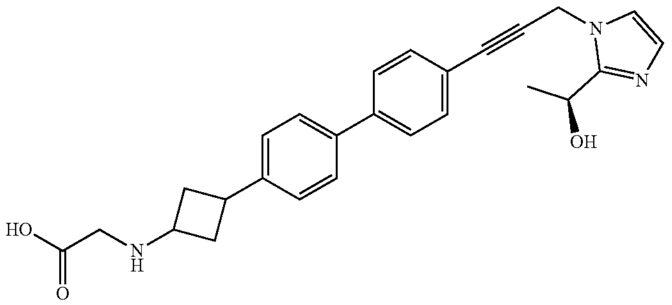 [SMILES: C[C@H](O)c1nccn1CC#Cc1ccc(-c2ccc(C3CC(NCC(=O)O)C3)cc2)cc1] | (S)-(3-(4'-(3-(2-(1-hydroxyethyl)-1H-imidazol-1-yl)prop-1-yn-1-yl)-[1,1'-biphenyl]-4-yl)cyclobutyl)glycine |
| 27 | 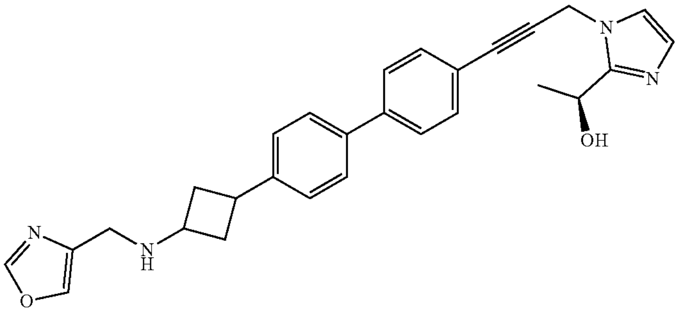 [SMILES: C[C@H](O)c1nccn1CC#Cc1ccc(-c2ccc(C3CC(NCc4cocn4)C3)cc2)cc1] | (S)-1-(1-(3-(4'-(3-((oxazol-4-ylmethyl)amino)cyclobutyl)-[1,1'-biphenyl]-4-yl)prop-2-yn-1-yl)-1H-imidazol-2-yl)ethan-1-ol |
| 28 | 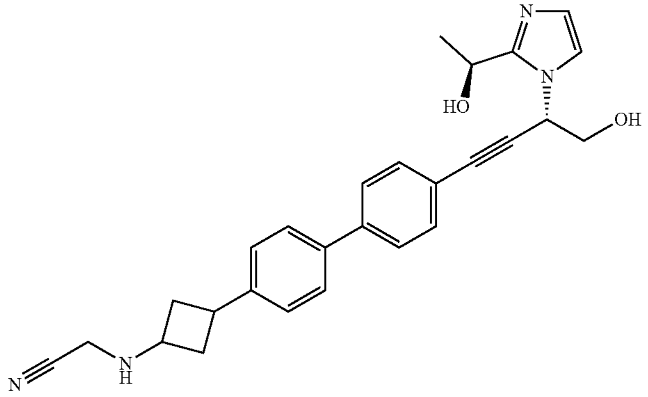 [SMILES: C[C@H](O)c1nccn1[C@@H](C#Cc1ccc(-c2ccc(C3CC(NCC#N)C3)cc2)cc1)CO] | 2-((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)acetonitrile |
| 29 | 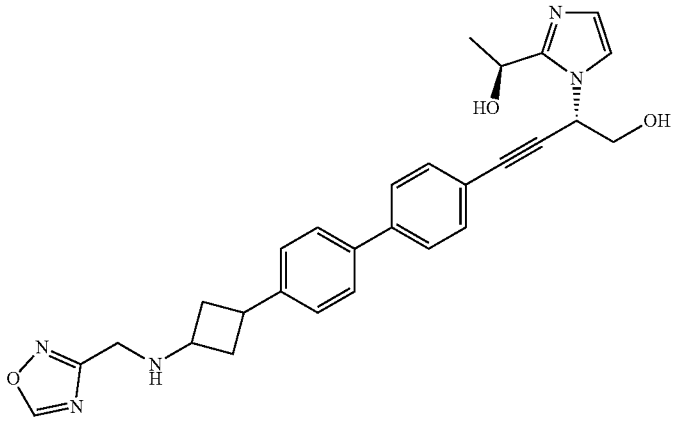 [SMILES: C[C@H](O)c1nccn1[C@@H](C#Cc1ccc(-c2ccc(C3CC(NCc4ncon4)C3)cc2)cc1)CO] | (S)-4-(4'-(3-(((1,2,4-oxadiazol-3-yl)methyl)amino)cyclobutyl)-[1,1'-biphenyl]-4-yl)-2-(2-((S)-1-hydroxyethyl)-1H-imidazol-1-yl)but-3-yn-1-ol |

TABLE 1a-continued

| Cpd | Structure | Name |
|---|---|---|
| 30 | 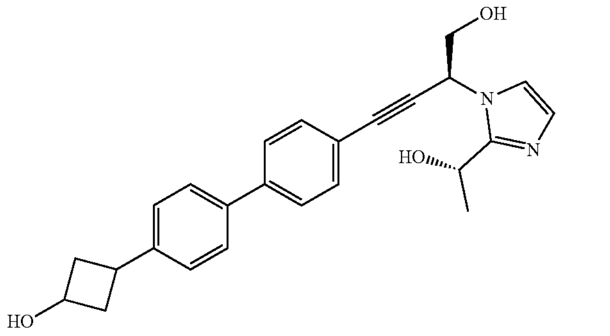 [SMILES: C[C@H](O)c1nccn1[C@@H](C#Cc1ccc(-c2ccc(C3CC(O)C3)cc2)cc1)CO] | 3-(4'-((S)-4-hydroxy-3-(2-((S)-1-hydroxyethyl)-1H-imidazol-1-yl)but-1-yn-1-yl)-[1,1'-biphenyl]-4-yl)cyclobutan-1-ol |
| 31 | 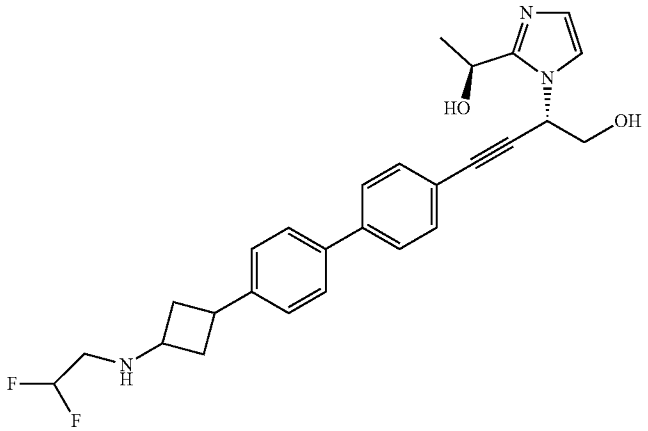 [SMILES: C[C@H](O)c1nccn1[C@@H](C#Cc1ccc(-c2ccc(C3CC(NCC(F)F)C3)cc2)cc1)CO] | (S)-4-(4'-(3-((2,2-difluoroethyl)amino)cyclobutyl)-[1,1'-biphenyl]-4-yl)-2-(2-((S)-1-hydroxyethyl)-1H-imidazol-1-yl)but-3-yn-1-ol |
| 32 | 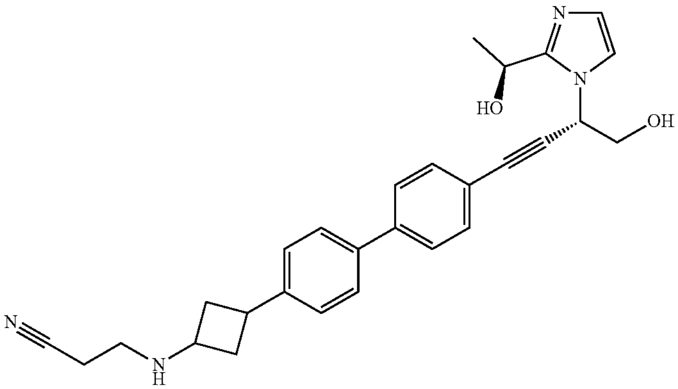 [SMILES: C[C@H](O)c1nccn1[C@@H](C#Cc1ccc(-c2ccc(C3CC(NCCC#N)C3)cc2)cc1)CO] | 3-((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)propanenitrile |
| 33 | 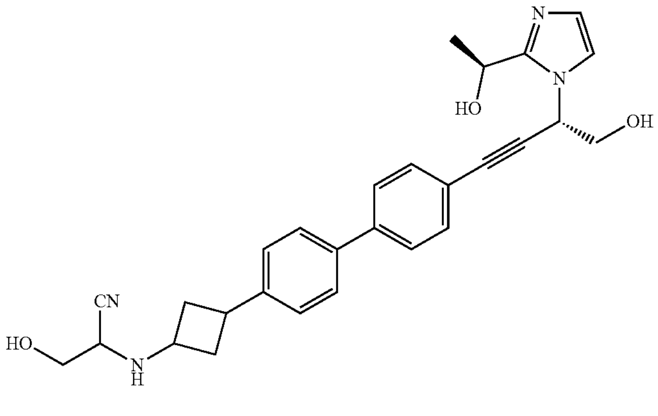 [SMILES: C[C@H](O)c1nccn1[C@@H](C#Cc1ccc(-c2ccc(C3CC(NC(C#N)CO)C3)cc2)cc1)CO] | 3-hydroxy-2-((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)propanenitrile |

TABLE 1a-continued
| Cpd | Structure | Name |
|---|---|---|
| 34 | 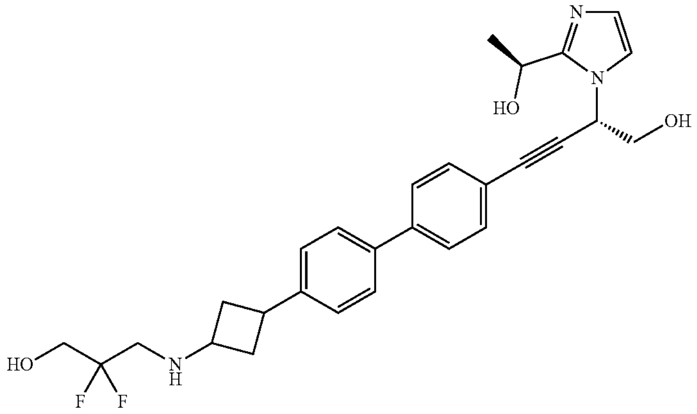 [SMILES: C[C@H](O)c1nccn1[C@@H](C#Cc1ccc(-c2ccc(C3CC(NCC(F)(F)CO)C3)cc2)cc1)CO] | (S)-4-(4'-(3-((2,2-difluoro-3-hydroxypropyl)amino)cyclobutyl)-[1,1'-biphenyl]-4-yl)-2-(2-((S)-1-hydroxyethyl)-1H-imidazol-1-yl)but-3-yn-1-ol |
| 35 | 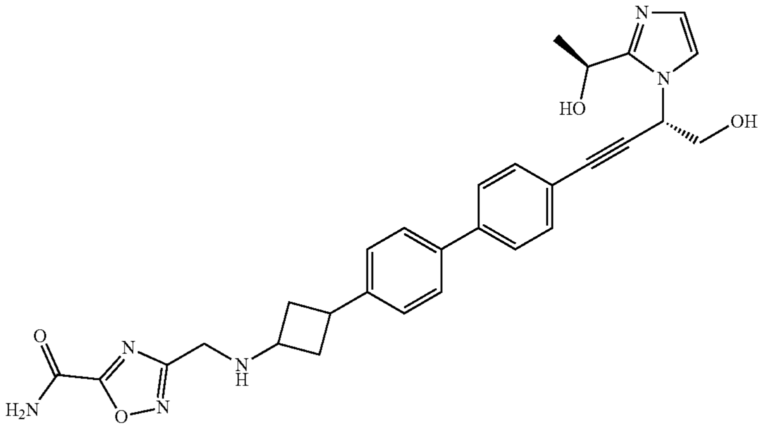 [SMILES: C[C@H](O)c1nccn1[C@@H](C#Cc1ccc(-c2ccc(C3CC(NCc4noc(C(N)=O)n4)C3)cc2)cc1)CO] | 3-(((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)methyl)-1,2,4-oxadiazole-5-carboxamide |
| 36 | 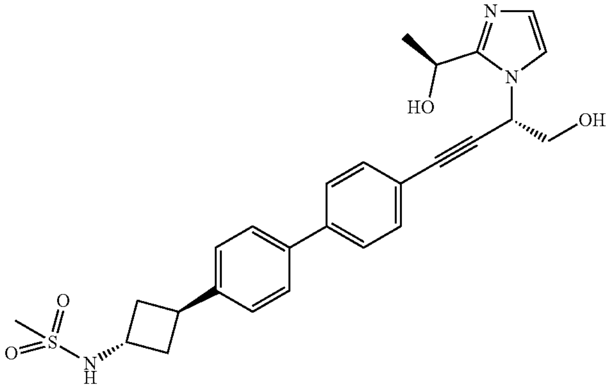 [SMILES: C[C@H](O)c1nccn1[C@@H](C#Cc1ccc(-c2ccc([C@H]3C[C@H](NS(C)(=O)=O)C3)cc2)cc1)CO] | N-((1S,3r)-3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)methanesulfonamide |

TABLE 1a-continued

| Cpd | Structure | Name |
| --- | --- | --- |
| 37 | 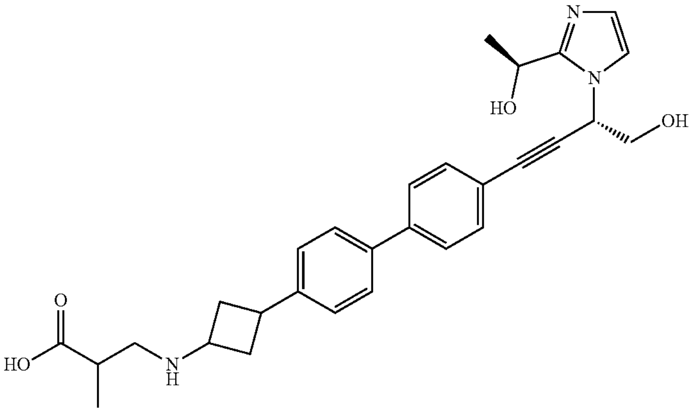 [SMILES: CC(CNC1CC(c2ccc(-c3ccc(C#C[C@@H](CO)n4ccnc4[C@H](C)O)cc3)cc2)C1)C(=O)O] | 3-((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)-2-methylpropanoic acid |
| 38 | 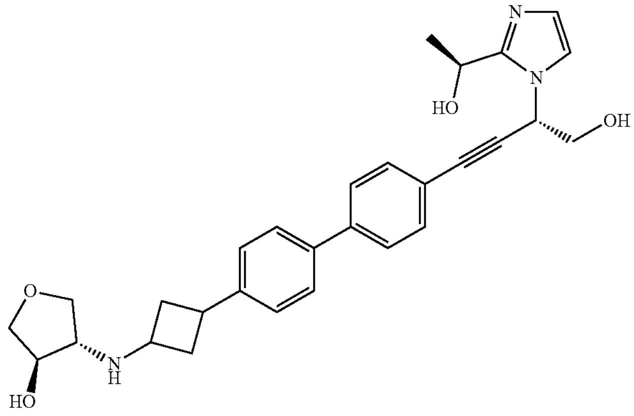 [SMILES: C[C@H](O)c1nccn1[C@@H](C#Cc1ccc(-c2ccc(C3CC(N[C@H]4COC[C@@H]4O)C3)cc2)cc1)CO] | (3R,4S)-4-((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)tetrahydrofuran-3-ol |
| 39 | 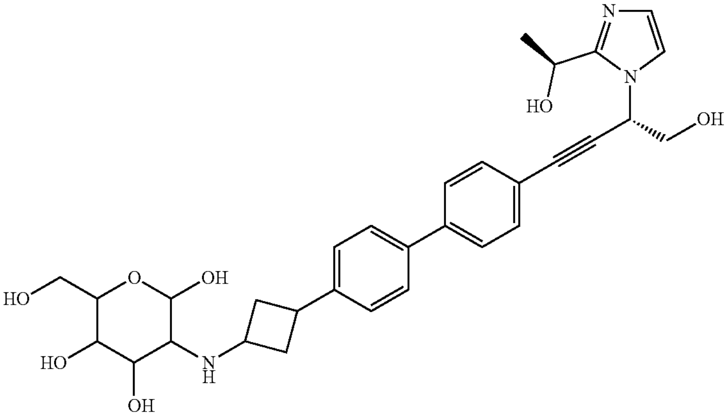 [SMILES: C[C@H](O)c1nccn1[C@@H](C#Cc1ccc(-c2ccc(C3CC(NC4C(O)OC(CO)C(O)C4O)C3)cc2)cc1)CO] | 3-((3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)amino)-6-(hydroxymethyl)tetrahydro-2H-pyran-2,4,5-triol |

TABLE 1a-continued

| Cpd | Structure | Name |
| --- | --- | --- |
| 40 | 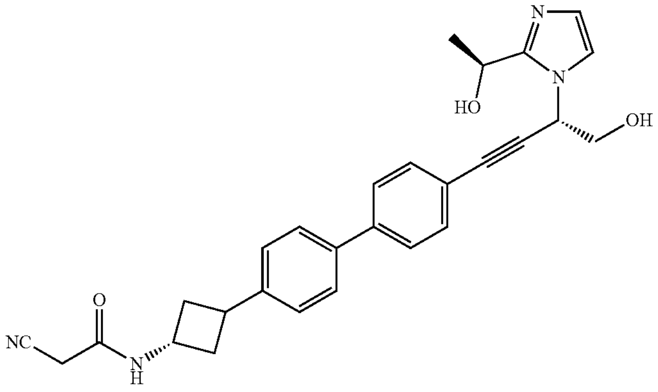 | 2-cyano-N-(3-(4'-((S)-4-hydroxy-3-(2-((S)-1-hydroxyethyl)-1H-imidazol-1-yl)but-1-yn-1-yl)-[1,1'-biphenyl]-4-yl)cyclobutyl)acetamide |
| 41 | 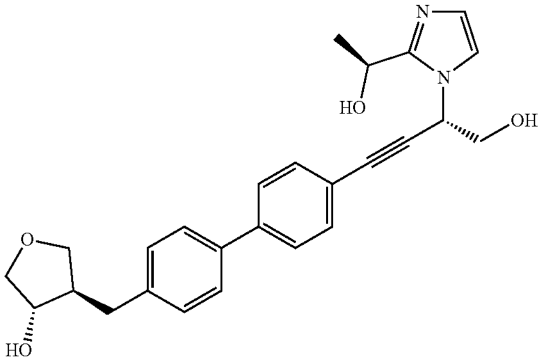 [SMILES: C[C@H](O)c1nccn1[C@@H](C#Cc1ccc(-c2ccc(C[C@@H]3COC[C@H]3O)cc2)cc1)CO] | (3S,4R)-4-((4'-((S)-4-hydroxy-3-(2-((S)-1-hydroxyethyl)-1H-imidazol-1-yl)but-1-yn-1-yl)-[1,1'-biphenyl]-4-yl)methyl)tetrahydrofuran-3-ol |
| 42 | 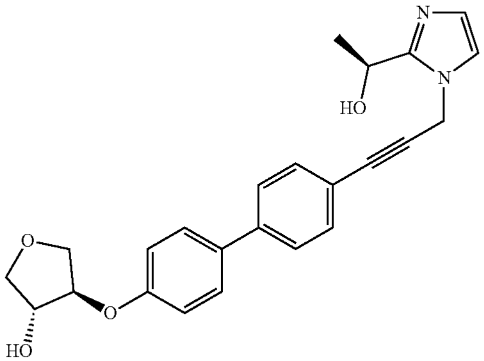 [SMILES: C[C@H](O)c1nccn1CC#Cc1ccc(-c2ccc(O[C@@H]3COC[C@H]3O)cc2)cc1] | (3R,4R)-4-((4'-(3-(2-((S)-1-hydroxyethyl)-1H-imidazol-1-yl)prop-1-yn-1-yl)-[1,1'-biphenyl]-4-yl)oxy)tetrahydrofuran-3-ol |
| 43 | 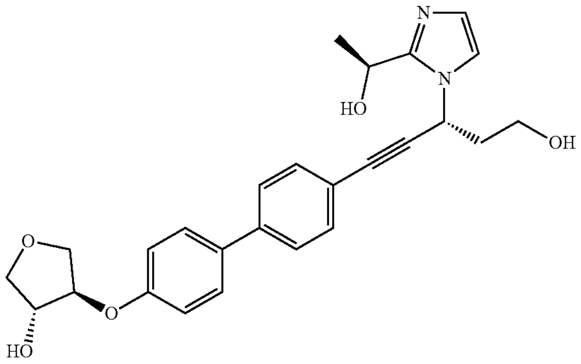 [SMILES: C[C@H](O)c1nccn1[C@@H](C#Cc1ccc(-c2ccc(O[C@@H]3COC[C@H]3O)cc2)cc1)CCO] | (3R,4R)-4-((4'-((R)-5-hydroxy-3-(2-((S)-1-hydroxyethyl)-1H-imidazol-1-yl)pent-1-yn-1-yl)-[1,1'-biphenyl]-4-yl)oxy)tetrahydrofuran-3-ol |

TABLE 1a-continued

| Cpd | Structure | Name |
|---|---|---|
| 44 | 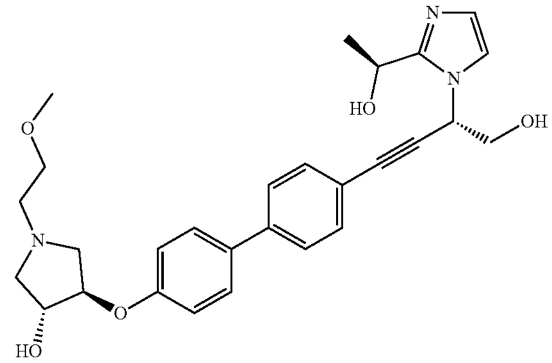 [SMILES: COCCN1C[C@@H](O)[C@H](Oc2ccc(-c3ccc(C#C[C@@H](CO)n4ccnc4[C@H](C)O)cc3)cc2)C1] | (3R,4R)-4-((4'-((S)-4-hydroxy-3-(2-((S)-1-hydroxyethyl)-1H-imidazol-1-yl)but-1-yn-1-yl)-[1,1'-biphenyl]-4-yl)oxy)-1-(2-methoxyethyl)pyrrolidin-3-ol |
| 45 | 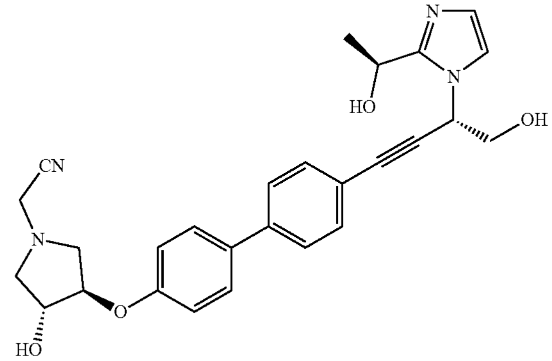 [SMILES: C[C@H](O)c1nccn1[C@@H](C#Cc1ccc(-c2ccc(O[C@@H]3CN(CC#N)C[C@H]3O)cc2)cc1)CO] | 2-((3R,4R)-3-hydroxy-4-((4'-((S)-4-hydroxy-3-(2-((S)-1-hydroxyethyl)-1H-imidazol-1-yl)but-1-yn-1-yl)-[1,1'-biphenyl]-4-yl)oxy)pyrrolidin-1-yl)acetonitrile |
| 46 | 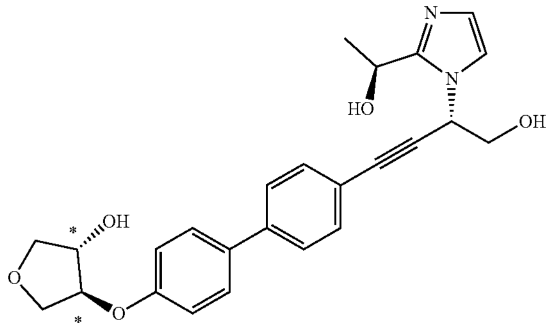 [SMILES: C[C@H](O)c1nccn1[C@@H](C#Cc1ccc(-c2ccc(O[C@H]3COC[C@@H]3O)cc2)cc1)CO] *racemic-cis | (cis)-4-((4'-((S)-4-hydroxy-3-(2-((S)-1-hydroxyethyl)-1H-imidazol-1-yl)but-1-yn-1-yl)-[1,1'-biphenyl]-4-yl)oxy)tetrahydrofuran-3-ol |

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic at the concentration or amount used, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

In some instances, heterocyclic rings may exist in tautomeric forms. In such situations, it is understood that the structures of said compounds are illustrated or named in one tautomeric form but could be illustrated or named in the alternative tautomeric form. The alternative tautomeric forms are expressly included in this disclosure, such as, for example, the structures illustrated below. For example, benzimidazoles or imidazoles could exist in the following tautomeric forms:

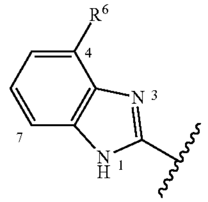
=
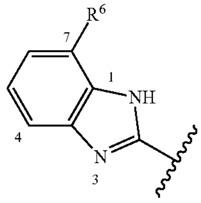
;

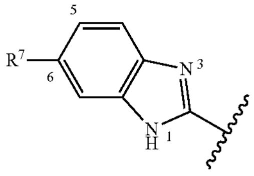
=
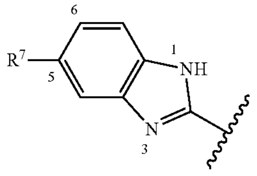

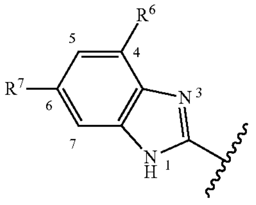
=
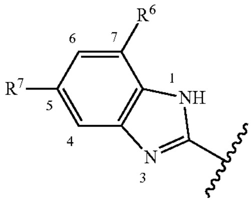
;

-continued

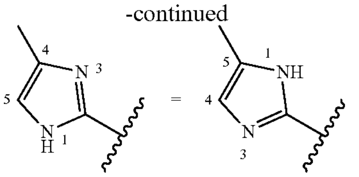

Preparation of Compounds

Compounds of Formula (I) described herein are synthesized using standard synthetic techniques or using methods known in the art in combination with methods described herein.

Unless otherwise indicated, conventional methods of mass spectroscopy, NMR, HPLC are employed.

Compounds are prepared using standard organic chemistry techniques such as those described in, for example, March's Advanced Organic Chemistry, 6*th* Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

An organometallic coupling reaction such as Suzuki-Miyaura reaction between Intermediate A and the appropriate aryl boronic acid or its ester or an organotrifluoroborate ($BF_3K$) B provided Intermediate C. Removal of the protecting group using appropriate deprotection methods yielded final Compound D.

In some other embodiments, compounds described herein are prepared as described in Scheme B.

Scheme B

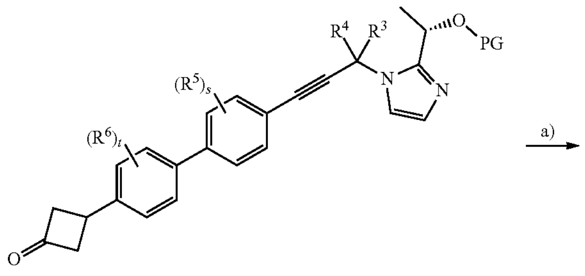

E

PG = protecting group

Scheme A

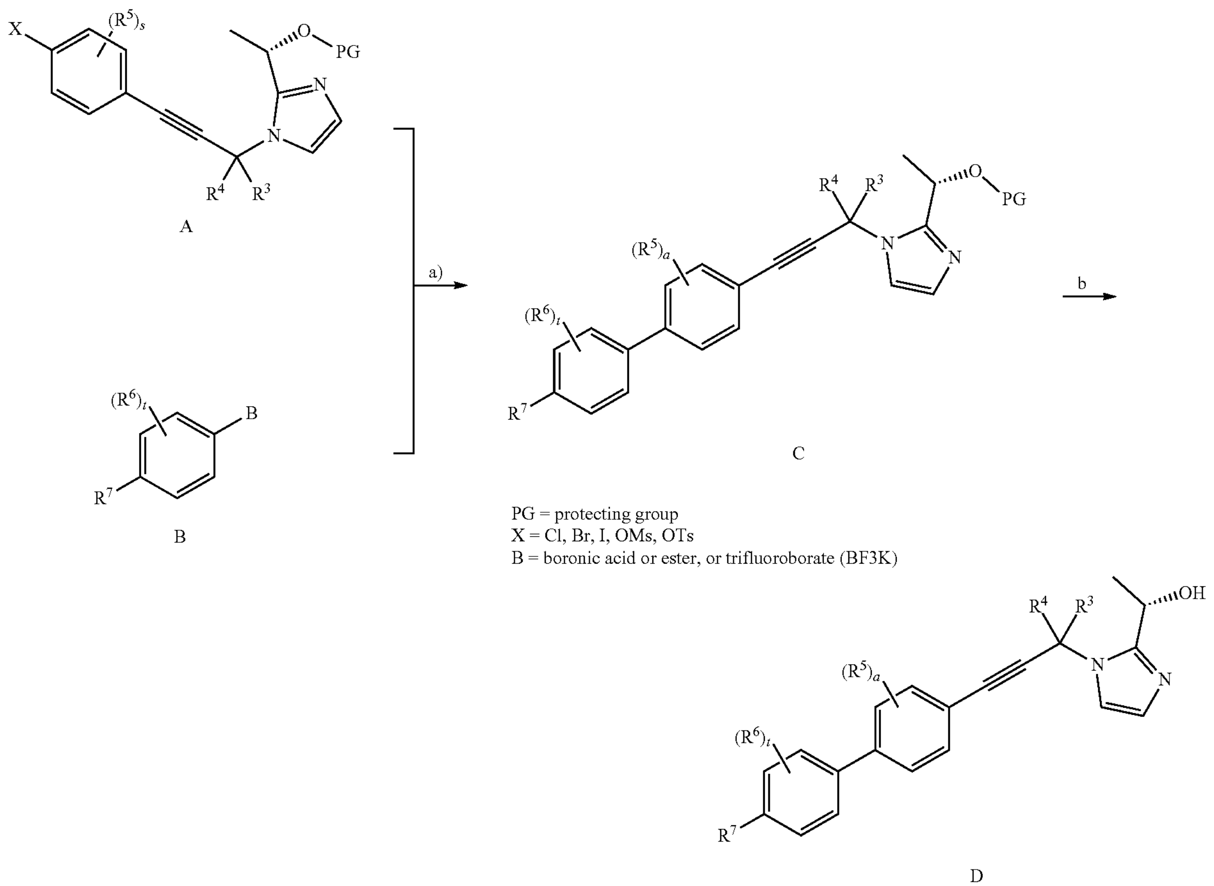

A B C D

PG = protecting group
X = Cl, Br, I, OMs, OTs
B = boronic acid or ester, or trifluoroborate (BF3K)

a) Pd catalyst, base; b) deprotection

-continued

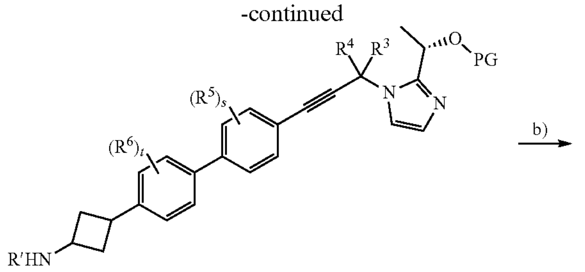

F

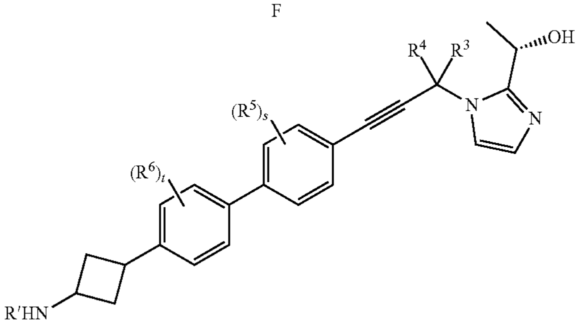

G a) amine (R'$NH_2$), AcOH, borohydride reagent; b) deprotection

Ketone containing Intermediate E is reacted with an appropriate amine (R'''—$NH_2$) under appropriate reductive amination conditions (such as treatment with a borohydride reagent: for example, $NaBH_4$, $NaCNBH_3$, or $NaB(OAc)_3H$) to provide Intermediate F. Removal of the protecting group using appropriate deprotection methods yielded final Compound G.

In some embodiments, compounds are prepared as described in the Examples.

Certain Terminology

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl. In some embodiments, an alkyl is methyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. Typical alkylene groups include, but are not limited to, $—CH_2—$, $—CH_2CH_2—$, $—CH_2CH_2CH_2—$, $—CH_2CH_2CH_2CH_2—$, and the like. In some embodiments, an alkylene is $—CH_2—$.

An "alkoxy" group refers to a —O(alkyl) group, where alkyl is as defined herein.

The term "alkylamine" refers to the $—N(alkyl)_xH_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, $—CH_2OH$, $—CH_2CH_2OH$, $—CH_2CH_2CH_2OH$, $—CH_2CH_2CH_2CH_2OH$, and the like. In some embodiments, a hydroxyalkyl is $—CH_2OH$ or $—CH_2CH_2OH$. In some embodiments, a hydroxyalkyl is $—CH_2OH$. In some embodiments, a hydroxyalkyl is $—CH_2CH_2OH$.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, $—CH_2NH_2$, $—CH_2CH_2NH_2$, $—CH_2CH_2CH_2NH_2$, $—CH_2CH_2CH_2CH_2NH_2$, and the like. In some embodiments, an amino alkyl is $—CH_2NH_2$ or $—CH_2CH_2NH_2$. In some embodiments, a hydroxyalkyl is $—CH_2NH_2$. In some embodiments, a hydroxyalkyl is $—CH_2CH_2NH_2$.

The term "alkenyl" refers to a type of alkyl group in which at least one carbon-carbon double bond is present. In one embodiment, an alkenyl group has the formula —C(R)$=CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —$C(CH_3)$=$CH_2$, —CH=$CHCH_3$, —$C(CH_3)$=$CHCH_3$, and —$CH_2CH$=$CH_2$.

The term "alkynyl" refers to a type of alkyl group in which at least one carbon-carbon triple bond is present. In one embodiment, an alkynyl group has the formula —C≡C—R, wherein R refers to the remaining portions of the alkynyl group. In some embodiments, R is H or an alkyl.

In some embodiments, an alkynyl is selected from ethynyl, propynyl, butynyl, pentynyl, hexynyl, and the like. Non-limiting examples of an alkynyl group include —C≡CH, —C≡$CCH_3$—C≡$CCH_2CH_3$, —$CH_2C$≡CH.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, a heteroalkyl is a $C_1$-$C_6$heteroalkyl where one or two atoms are independently selected from O, NH, and S.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahydronaphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1]pentyl. In some embodiments, a cycloalkyl is a $C_3$-$C_6$cycloalkyl. In some embodiments, a cycloalkyl is a $C_3$-$C_4$cycloalkyl. In some embodiments, a cycloalkyl is a cyclopropyl. In some embodiments, a cycloalkyl is a cyclobutyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is —$CF_3$.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, $—NH_2$, —NH(alkyl), $—N(alkyl)_2$, —OH, $—CO_2H$, $—CO_2$alkyl, $—C({=}O)NH_2$, —C(=O)NH(alkyl), $—C({=}O)N(alkyl)_2$, $—S({=}O)_2NH_2$, $—S({=}O)_2NH(alkyl)$, $—S({=}O)_2N(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, $—NH_2$, $—NH(CH_3)$, $—N(CH_3)_2$, —OH, $—CO_2H$, $—CO_2(C_1$-$C_4$alkyl), $—C({=}O)NH_2$, $—C({=}O)NH(C_1$-$C_4$alkyl), $—C({=}O)N(C_1$-$C_4$alkyl$)_2$, $—S({=}O)_2NH_2$, $—S({=}O)_2NH(C_1$-$C_4$alkyl), $—S({=}O)_2N(C_1$-$C_4$alkyl$)_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, $—SC_1$-$C_4$alkyl, $—S({=}O)C_1$-$C_4$alkyl, and $—S({=}O)_2C_1$-$C_4$alkyl. In some embodiments, optional substituents are independently selected from halogen, —CN, $—NH_2$, —OH, $—NH(CH_3)$, $—N(CH_3)_2$, $—CH_3$, $—CH_2CH_3$, $—CHF_2$, $—CF_3$, $—OCH_3$, $—OCHF_2$, and $—OCF_3$. In some embodiments, substituted groups are substituted with one or two of the preceding groups. In some embodiments, an optional substituent on an aliphatic carbon atom (acyclic or cyclic) includes oxo (=O).

In some embodiments, each substituted alkyl, substituted fluoroalkyl, substituted heteroalkyl, substituted carbocycle, and substituted heterocycle is substituted with one or more $R^5$ groups independently selected from the group consisting of halogen, $C_1$-$C_6$alkyl, monocyclic carbocycle, monocyclic heterocycle, —CN, $—OR^{21}$, $—CO_2R^{21}$, $—C({=}O)N(R^{21})_2$, $—N(R^{21})_2$, $—NR^{21}C({=}O)R^{22}$, $—SR^{21}$, $—S({=}O)R^{22}$, $—SO_2R^{22}$, and $—SO_2N(R^{21})_2$; each $R^{21}$ is independently selected from hydrogen, $C_1$-$C_6$alkyl, $C_1$-$C_6$fluoroalkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{21}$ groups are taken together with the N atom to which they are attached to form a N-containing heterocycle; each $R^{22}$ is independently selected from $C_1$-$C_6$alkyl, $C_1$-$C_6$fluoroalkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is an inhibitor.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development or progression of the disease or condition, relieving the disease or condition, causing regression of the disease or condition, relieving a secondary condition caused by the disease or condition, or stopping the symptoms of the disease or condition either prophylactically and/or therapeutically.

Pharmaceutical Compositions

In certain embodiments, the heterocyclic LpxC inhibitory compound as described herein is administered as a pure chemical. In other embodiments, the heterocyclic LpxC inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Provided herein is a pharmaceutical composition comprising at least one heterocyclic LpxC inhibitory compound as described herein, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

Some embodiments provide a pharmaceutical composition comprising a compound of Formula (I), or a pharmaceutically acceptable salt thereof, and a pharmaceutically acceptable excipient.

In certain embodiments, the heterocyclic LpxC inhibitory compound as described by Formula (I) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

The dose of the composition comprising at least one heterocyclic LpxC inhibitory compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

Other embodiments and uses will be apparent to one skilled in the art in light of the present disclosures. The following examples are provided merely as illustrative of various embodiments and shall not be construed to limit the invention in any way.

EXAMPLES

As used above, and throughout the description of the invention, the following abbreviations, unless otherwise indicated, shall be understood to have the following meanings:

Abbreviations

ACN or MeCN: acetonitrile;
aq: aqueous;
Boc or BOC: tert-butoxycarbonyl;
DCM: dichloromethane;
DIAD: diisopropyl azodicarboxylate;
DMAP: 4-dimethylaminopyridine;
DMF: dimethylformamide;
DMP: Dess-Martin periodinane
DPPA: diphenylphosphoryl azide;
Eq. or equiv: equivalents;
EtOAc: ethyl acetate;
g: grams
h or hr(s): hour(s);
HPLC: high-performance liquid chromatography;
LC-MS, LC MS, or LCMS: liquid chromatography-mass spectrometry;
LDA: lithium diisopropylamide;
M: molar;
MeOH: methanol;
mg: milligrams;
min: minute;
mL: milliliter;
mmol: millimole;
MsCl: methanesulfonyl (mesyl) chloride;
MTBE: methyl tert-butyl ether;
N: normal;
NBS: N-bromosuccinimide;
NMR: nuclear magnetic resonance;
Pet ether: petroleum ether;
PPTS: pyridinium p-toluenesulfonate;
p-TSA: para-toluenesuflonic acid
rt: room temperature;
SFC: supercritical fluid chromatography;
TEA: triethylamine (or $Et_3N$);
TFA: trifluoroacetic acid;
THF: tetrahydrofuran;
THP: tetrahydropyran;
TLC: thin layer chromatography;
TsCl: para-toluenesulfonyl (tosyl) chloride.

The following examples are provided for illustrative purposes only and not to limit the scope of the claims provided herein.

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1: Preparation of 2-((1S)-1-((tetrahydro-2H-pyran-2-yl)oxy)ethyl)-1H-imidazole (Int-5)

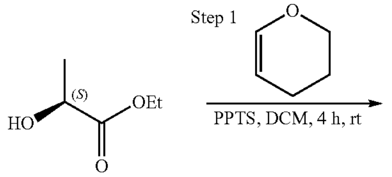

Int-1

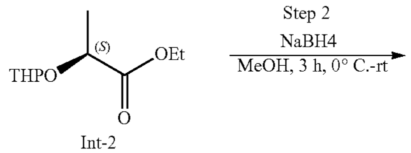

Int-2

-continued

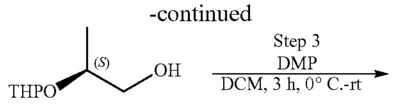

Int-3

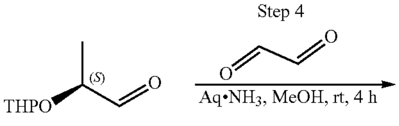

Int-4

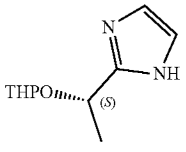

Int-5

Step 1: Pyridinium p-toluenesulfonate (0.408 g, 1.62 mmol) was added to a solution of ethyl (s)-(−)-lactate (Int-1, 50 g, 0.4232 mol) and 3,4-dihydro-2H-pyran (46.2 g, 0.549 mol) in DCM (566 mL, 11 v/w). The reaction mixture was stirred 4 h at room temperature. After completion of the reaction, as monitored by TLC, the reaction mixture was diluted with DCM and washed with saturated $NaHCO_3$ solution. The layers were separated, the organic layer dried over sodium sulphate, filtered and concentrated under reduced pressure to get pure Int-2 as a colorless liquid as a mixture of diastereomers. The $^1$H NMR data was in accordance with that reported in *J. Org. Chem.* 2009, 74, 8154. Yield: 80 g, 93%.

Step 2: To a 0° C. cooled solution of Int-2 (50 g, 0.2472 mol) in MeOH (750 mL, 15 v/w), was added $NaBH_4$ (37.40 g, 0.988 mol, 4 equiv.) in portions over 1 h. The reaction mixture was allowed to warm to room temperature over 3 h. After completion of the reaction, as monitored by TLC, the reaction mixture was quenched with sat. $NH_4Cl$ solution and extracted with DCM (500 mL×3). The layers were separated, and the combined organic layer was dried over sodium sulphate, filtered and concentrated under reduced pressure. The crude product was purified by silica column chromatography (60-120 mesh, eluted with 30-50% EtOAc and pet ether) to get pure Int-3 as a colourless liquid. Yield: 25 g, 63%.

Step 3: To a 0° C. cooled solution of Int-3 (40 g, 0.2496 mol) in DCM (800 mL, 20 v/w) was added Dess-Martin periodinane (158.8 g, 0.3744 mol) in portions over 30 min. The reaction mixture was allowed to warm to room temperature over 3 h. After completion of the reaction, as monitored by TLC, the reaction mixture was filtered on Celite bed and the bed was further washed with DCM (1000 mL). The filtrate was washed with saturated $NaHCO_3$ solution followed by brine. The organic layer was dried over sodium sulphate, filtered and concentrated under reduced pressure at 30° C. Some white solid was observed in the crude product. To remove this impurity, the crude product was dissolved in diethyl ether and washed with 10% NaOH solution (500 mL×2). The organic layer was dried over sodium sulphate, filtered and concentrated under reduced pressure to get a crude mass. Since the formation of the white solid was observed yet again, the crude mass was dissolved in diethyl ether (500 mL), filtered on celite bed and washed with diethyl ether (750 mL) to completely remove the unwanted impurity. The filtrate was concentrated under reduced pressure at 30° C. to get Int-4 as a colourless liquid as a mixture of diastereomers, which was taken to the next step without further purification. The $^1$H NMR showed all the characteristic resonances reported in Org. Lett. 2009, 11, 1103. Yield: 39 g, 98%.

Step 4: To a solution of Int-4 (39 g, 246.5 mol) in MeOH (390 mL, 10 v/w), was added glyoxal (40% in water, 97.5 mL, 2.5 v/w). To the above mixture cooled to 10° C., was added 28% aqueous ammonia (120 mL, 3 v/w). The ice bath was removed, and the reaction mixture temperature allowed to run at room temperature for 4 h. After completion of the reaction, as monitored by TLC and LC-MS, the reaction mixture was concentrated under reduced pressure. The crude product was purified by column chromatography (SiO2 60-120 mesh, eluted with 80-100% EtOAc in Pet ether) to get 2-((1S)-1-((tetrahydro-2H-pyran-2-yl)oxy)ethyl)-1H-imidazole (Int-5) as an off white solid as a mixture of diastereomers. The $^1$H NMR recorded in DMSO-d6 and LCMS were supportive of the structure. For $^1$H NMR values recorded in $CDCl_3$, see WO 2018216822A1. Yield: 27 g, 56%. LC MS: Calculated for $C_{10}H_{16}N_2O_2$ is 196.25, Observed: 197.1 $[M+H]^+$.

Example 2: Preparation of 1-(3-(4-iodophenyl)prop-2-yn-1-yl)-2-((1S)-1-((tetrahydro-2H-pyran-2-yl)oxy)ethyl)-1H-imidazole (Int-9)

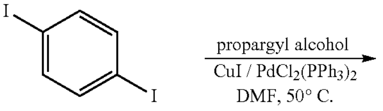

Int-8

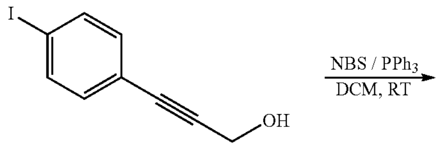

Int-7

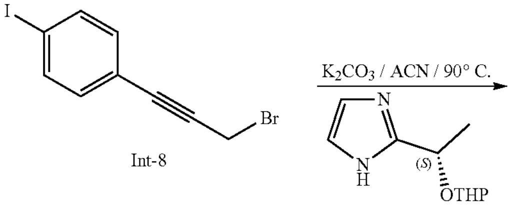

Int-8

Int-5

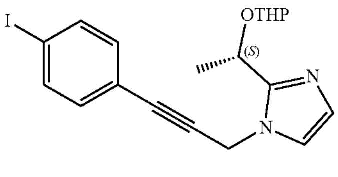

Int-9

Step 1: To a stirred solution of 2,4-diiodobenzene (Int-6) (5 g, 15 mmol) in DMF (20 mL), propargyl alcohol (0.26 mL, 3 mmol) was added followed by the addition of CuI (5 mol %) and $PdCl_2(PPh_3)_2$(5 mol %). The reaction was heated at 50° C. Two equal portions of propargyl alcohol (0.26 ml×2, 3 mmol) was added over the next 90 minutes with an interval of over 45 minutes and stirred for an additional 2 h. The reaction mixture was quenched with ice cold water (25 mL) and extracted with Ethyl acetate (2×35 mL). The organic layer was further washed with brine, dried ($MgSO_4$) and concentrated under vacuum to give the crude mixture. The compound was further purified on a silica gel column eluted with hexanes in ethyl acetate to give the desired compound Int-7 in about 52% yield.

Step 2: A solution of Int-7 (2 g, 7.6 mmol) in DCM (30 mL) was cooled to 0° C. To this cooled solution, N-bromo-succinimide (8.1 mmol) and $PPh_3$ (7.6 mmol) was added and stirred at 0° C. for 2 h. After consumption of starting material, the reaction mixture was diluted with DCM and quenched by pouring to the cooled sat. $NaHCO_3$ solution and extracted twice with DCM. The combined organic layers were dried over anhydrous $Na_2SO_4$, filtered and concentrated under reduced pressure to afford crude product Int-8. The compound was purified on a silica gel column eluted with hexanes in ethyl acetate to afford the desired Int-8 (2.01 g, 84%) as a thick oil. LC MS: Calculated for $C_9H_8BrI$ is 322.97, not ionized.

Step 3: A solution of Int-5 (1 g, 5.1 mmol, see part II) in acetonitrile (5 mL) was added to the slurry of potassium carbonate (10 mmol) in acetonitrile (10 mL) and the reaction mixture heated to 70° C. for 30 min. To the preheated reaction mixture, a solution of Int-8 (1.64 g, 5.1 mmol) in acetonitrile (5 mL) was added and the heating continued at 80° C. for 3 h. After consumption of the starting materials, the reaction mixture was cooled to rt and quenched with sat. $NH_4Cl$. The reaction mixture was diluted with water and extracted twice with EtOAc. The combined organic layers were dried over $Na_2SO_4$, filtered and concentrated under reduced pressure. The crude product was purified by column chromatography using silica gel (230-400 mesh) by eluting with 1-2% methanol in DCM to afford pure compound Int-9 (1.35 g, 78%). LC MS: Calculated for $C_{19}H_{23}IN_2O_2$ is 438.31, Observed: 439.2 $[M+H]^+$.

Example 3: Preparation of (2S)-4-(4-bromophenyl)-2-(2-((1S)-1-((tetrahydro-2H-pyran-2-yl)oxy)ethyl)-1H-imidazol-1-yl)but-3-yn-1-ol (Int-15)

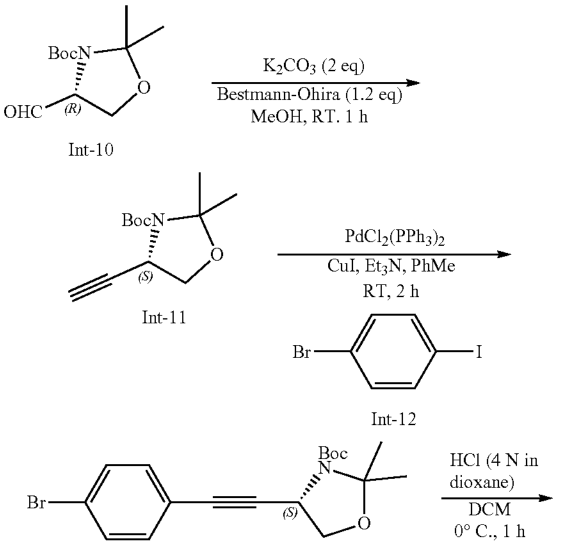

Int-10, Int-11, Int-12, Int-13

-continued

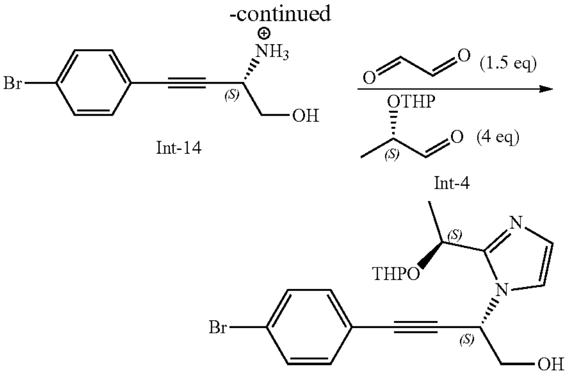

Int-14, Int-4, Int-15

Step 1: To a stirred 0° C. cooled solution of Int-10 (5 g, 0.0218 mol) in dry MeOH (50 mL), Dimethyl (1-diazo-2-oxo propyl) phosphonate (Bestmann-Ohira Reagent, 5.02 g, 0.0261 mol) was added dropwise and the reaction mixture was stirred at 0° C. for 5 min. Then $K_2CO_3$ (6 g, 0.0436 mol) was added to the reaction mixture and stirred at 0° C. for 10 min. Then ice cold water bath was removed, and the reaction mixture stirred at RT for 1 h. After the completion of the reaction, the reaction mixture was concentrated under reduced pressure. The crude residue was diluted with EtOAc (500 mL) and washed with water. The organic layer was separated, dried over anhydrous $Na_2SO_4$, filtered and concentrated under reduced pressure. The crude product was purified by column chromatography on silica gel (60-120 mesh) by eluting with 10-12% ethyl acetate in petrol ether to afford Int-11 (3.79 g, 77%). LC MS: Calculated for $C_{12}H_{19}NO_3$ is 225.29, not ionized.

Step 2: To a stirred solution of Int-11 (3.79 g, 16.82 mmol) in dry Toluene (40 mL), were added 1-bromo-4-iodobenzene (Int-12) (5.71 g, 20.18 mmol) and TEA (6.9 mL, 49.26 mmol), the reaction mixture was degassed with nitrogen for 5 min. then bis(triphenylphosphine)palladium chloride (230 mg, 0.326 mmol) and CuI (187 mg, 0.985 mmol) were added and stirred at RT for 2 h. After the completion of the reaction, the reaction mixture was concentrated under reduced pressure. The crude residue was diluted with DCM (500 mL) and washed with water. The organic layer was separated, dried over anhydrous $Na_2SO_4$, filtered and concentrated under reduced pressure. The crude product was purified by column chromatography on silica gel (60-120 mesh) by eluting with 10-12% ethyl acetate in petrol ether to afford Int-13 (5.4 g, 84.5%). LC MS: Calculated for $C_{18}H_{22}BrNO_3$ is 380.280, Observed: 282 $[M\text{-}Boc+2]^+$.

Step 3: To a stirred 0° C. cooled solution of Int-13 (5.4 g, 0.0142 mol) in dry DCM (54 mL), HCl (4 N in dioxane, 18 mL) was added and the reaction mixture stirred at RT for 2 h.

After completion of the reaction, the solvent was concentrated under reduced pressure to afford the crude product as an off-white solid Int-14 (4.2 g). LC MS: Calculated for $C_{10}H_{11}BrNO+$ is 241.11, Observed: 242[M+2 for the free base].

Step 4: To a stirred solution of Int-14 (2 g, 0.0072 mol) in MeOH (20 mL) were added (2S)-2-((tetrahydro-2H-pyran-2-yl)oxy)propanal (Int-4, 4.5 g, 0.021 mol), $NH_4OAc$ (1.1 g, 0.0144 mol) and Glyoxal (40% in $H_2O$ 1.6 mL, 0.0108 mol) at RT. The reaction mixture was stirred at 80° C. for 2 h. After completion of the reaction, the reaction mixture was concentrated under reduced pressure to get the crude residue (By LCMS analysis, the desired product was around 46% and 2-unsubstituted imidazole was 19%). The crude residue was diluted with EtOAc (250 mL) and washed with water (100 mL). The organic layer was dried over anhydrous $Na_2SO_4$ and concentrated under reduced pressure to afford the crude product. The crude product was purified by column chromatography on silica gel (230-400 mesh) by eluting with 50-60% ethyl acetate in petrol ether to afford product Int-15 (790 mg, 22.76%). LC-MS: Calculated for $C_{20}H_{23}BrN_2O_2$ is 419.230, Observed: 421 $[M+2H]^+$.

Example 4: Preparation of tert-butyl ((2S)-4-(4-bromophenyl)-2-(2-((1S)-1-((tetrahydro-2H-pyran-2-yl)oxy)ethyl)-1H-imidazol-1-yl)but-3-yn-1-yl)carbamate (Int-21)

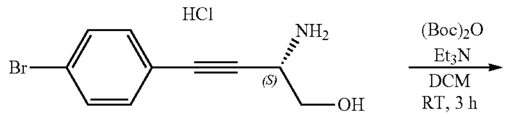

Int-14

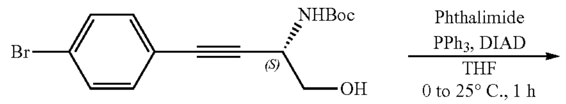

Int-16

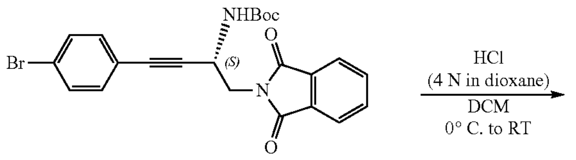

Int-17

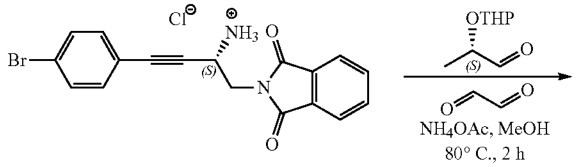

Int-18

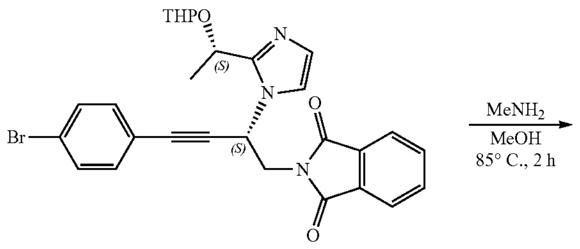

Int-19

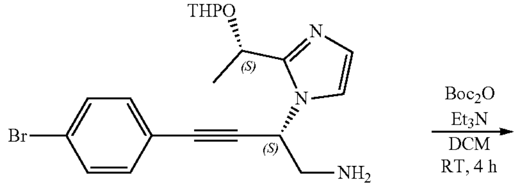

Int-20

-continued

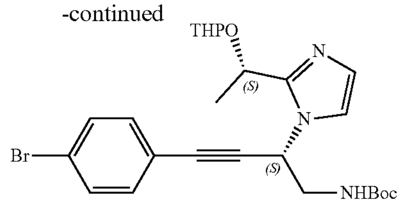

Int-21

Step 1: To a stirred solution of Int-14 (5.5 g, 22.91 mmol) in DCM (55 mL), were added Boc-anhydride (5.85 mL, 25.2 mmol) and triethylamine (9.37 mL, 68.7 mmol) at room temperature. The reaction mixture was stirred for 3 h. After complete consumption of the starting material, the reaction mixture was diluted with DCM (200 mL) and washed with water (100 mL). The organic layer was dried over anhydrous sodium sulphate, filtered and concentrated under reduced pressure. The crude product was purified by flash column chromatography ($SiO_2$, 100-200 mesh size; 15-20% EtOAc in hexane) to afford Int-16 (5.0 g, 63.5%) as an off-white solid. LC-MS: Calculated for $C_{15}H_{18}BrNO_3$ is 340.22, Observed: 284.0 $[M-56]^+$ and 286.0 $[M-56+2]^+$ Step 2: To a stirred solution of Int-16 (5.0 g, 14.70 mmol) in THF (37 mL), were added phthalamide (2.378 g, 16.17 mmol) and triphenylphosphine (7.71 g, 29.4 mmol) and cooled to 0° C. To this reaction mixture, was added DIAD (5.8 mL, 29.4 mmol) slowly and continued stirring for 1 h. After completion of the reaction, the reaction mixture was diluted with EtOAc (200 mL) and washed with water (100 mL). The organic layer was dried over anhydrous sodium sulphate, filtered and concentrated under reduced pressure to afford crude Int-17 (6.9 g (crude), which was carried for the next step without any purification. The sample showed contamination with $PPh_3O$. LC-MS: Calculated for $C_{23}H_{21}BrN_2O_4$ is 469.34, Observed: 413.0 $[M-56]^+$.

Step 3: To a stirred solution of crude Int-17 (6.9 g, 14.70 mmol) in DCM (70 mL) was added HCl (4 M in dioxane, 36.8 mL, 147 mmol) at 0° C. The reaction mixture was stirred for 3 h at room temperature. The reaction was followed by TLC. After completion of the reaction, the solids formed were filtered under vacuum and washed with hexane to afford Int-18 (4.5 g, 75%) as a white solid. LC-MS: Calculated for $C_{18}H_{14}BrN_2O_2$ is 369 for the ammonium ion, Observed: 369.0 $[M]^+$ and 371.0 $[M+2]^+$.

Step 4: To a stirred solution of Int-18 (4.5 g, 11.09 mmol) in MeOH (45 mL) was added ammonium acetate (1.710 g, 22.19 mmol) and stirred at room temperature for 10 min. To this reaction mixture was added (2S)-2-((tetrahydro-2H-pyran-2-yl)oxy)propanal (7.02 g, 44.4 mmol) and continued the stirring for 10 min. Finally, glyoxal (40% aqueous solution, 1.916 mL, 16.64 mmol) was added. After stirring for 10 min at room temperature, the reaction mixture was heated at 80° C. for 2 h. After completion of the reaction, volatiles were evaporated under reduced pressure. The resulting residue was added water (100 mL) and extracted with 5% MeOH in DCM (100 mL×2). The combined organic layer was dried over anhydrous sodium sulphate, filtered and concentrated under reduced pressure. The crude product was purified by flash column chromatography ($SiO_2$, 230-400 mesh size; 80-90% EtOAc in hexane) to afford Int-19 (2.8 g, 46%) as a pale-yellow gummy solid as mixture of diastereoisomers as seen in the LC profile without baseline separation. LC-MS: Calculated for $C_{28}H_{26}BrN_3O_4$ is 548.44, Observed: 548.0 [M]$^+$, 550.0 [M+2]$^+$.

Step 5: To a stirred solution of Int-19 (2.8 g, 5.11 mmol) in MeOH (28 mL) was added methylamine (40% in water; 3.71 mL, 51.1 mmol) at room temperature. The pressure tube was sealed and heated at 85° C. for 2 h. After completion of the reaction, the reaction mixture was diluted with DCM (150 mL) and washed with water (100 mL). The organic layer was dried over anhydrous sodium sulphate and concentrated under reduced pressure to afford Int-20 (2.0 g, 94%) as a pale-yellow liquid. The crude was carried for next step without any purification. LC-MS: Calculated for $C_{20}H_{24}BrN_3O_2$ is 418.34, Observed: 418.2 [M] and 420.2 [M+2]$^+$.

Step 6: To a stirred solution of Int-20 (2.4 g, 5.74 mmol) in DCM (27 mL), were added triethylamine (2.347 mL, 17.21 mmol), Boc-anhydride (1.598 mL, 6.88 mmol) at room temperature. After stirring for 4 h, the reaction mixture was diluted with DCM (150 mL) and washed with water (100 mL). The organic layer was dried over anhydrous sodium sulphate, filtered and concentrated under reduced pressure. The resulting crude product was purified by flash column chromatography ($SiO_2$, 230-400 mesh size; 40% EtOAc in hexane) to afford Int-21 (1.0 g, 32%) as a brown gummy solid. LC-MS: Calculated for $C_{25}H_{32}BrN_3O_4$ is 518.45, Observed: 518.0 [M]$^+$, 520.0 [M+2]$^+$.

Example 5: Preparation of (3S)-5-(4-bromophenyl)-3-(2-((1S)-1-((tetrahydro-2H-pyran-2-yl)oxy)ethyl)-1H-imidazol-1-yl)pent-4-yn-1-ol (Int-109a)

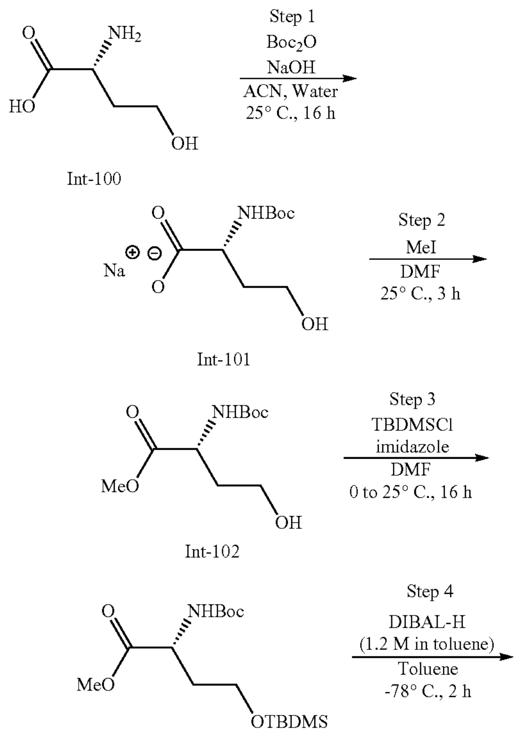

Int-100

Int-101

Int-102

Int-103

-continued

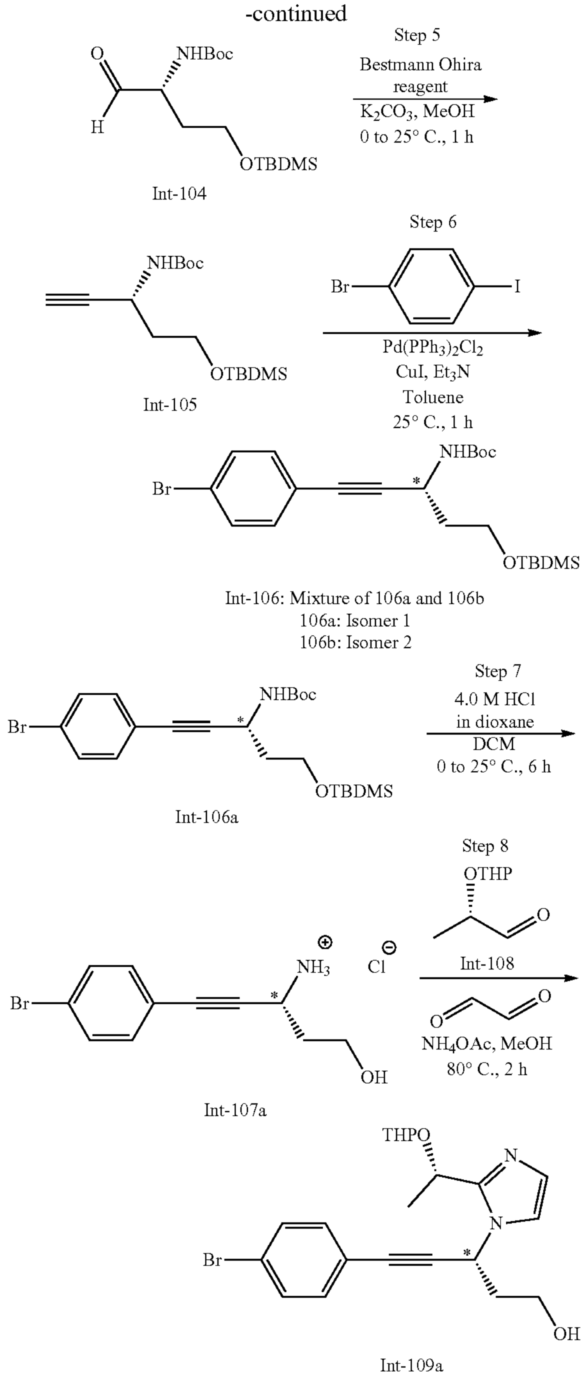

Int-104

Int-105

Int-106: Mixture of 106a and 106b
106a: Isomer 1
106b: Isomer 2

Int-106a

Int-107a

Int-109a

Step 1: To a stirred solution of D-homoserine (Int-100, 25.0 g, 210 mmol) in acetonitrile: water (1:1; 500 mL), was added NaOH (10.07 g, 252 mmol) at 0° C. After stirring for 1 h at 25° C., to the reaction mixture, was added Boc-anhydride (10.07 g, 252 mmol). The reaction mixture was stirred for 16 h. The reaction mixture was concentrated under reduced pressure and azeotroped with toluene (200 mL) to afford Int-101 as an off-white gummy solid, which was taken to the next step without any purification. Yield=50.0 g (Crude product weight).

Step 2: To a stirred solution of Int-101 (50.0 g, 207 mmol) in DMF (300 mL), was added iodomethane (25.9 mL, 415 mmol) at 0° C. The reaction mixture was stirred at 25° C. for 3 h. After completion of the reaction, the reaction mixture was concentrated under reduced pressure to afford Int-102 as an off-white gummy solid. $^1$HNMR showed presence of DMF. This was taken for the next step without any further purification. Yield=49.0 g (Crude product weight).

Step 3: To a stirred solution of Int-102 (48.0 g, 206 mmol) in DMF (300 mL), were added imidazole (28.0 g, 412 mmol) and tert-butyldimethyllsilyl chloride (46.5 g, 309 mmol) at 0° C. The reaction mixture was stirred at 25° C. for 16 h. After completion of reaction, the reaction mixture was concentrated under reduced pressure. The resulting residue was taken in EtOAc (200 mL), washed with ice cold water (200 mL×2), brine (100 mL), dried over anhydrous sodium sulphate, filtered and concentrated under reduced pressure to afford the crude product. The crude product was purified by column chromatography ($SiO_2$ 100-200 mesh; 5-7% EtOAc in pet ether) to afford Int-103 as a yellow liquid. Yield=47.0 g (89%)

Step 4: To a stirred solution of Int-103 (20.0 g, 57.5 mmol) in dry toluene (200 mL), was added DIBAL-H (1.2 M in toluene; 71.9 mL, 86 mmol) at −78° C. After stirring for 2 h at −78° C., the reaction was quenched by the addition of MeOH (100 mL). After stirring for 15 min, to this was added 50% sodium potassium tartrate solution (150 mL) and allowed to stir at room temperature for 1 h. This was extracted with EtOAc (300 mL×2). The combined organic layers were dried over anhydrous sodium sulphate, filtered and concentrated under reduced pressure to afford the crude product Int-104 as a colorless liquid. The crude material was used in the next step without any further purification. Yield=13.8 g (76%).

Step 5: To a stirred solution of Int-104 (13.8 g, 43.5 mmol) in MeOH (140 mL), was added potassium carbonate (12.01 g, 87 mmol) followed by Bestmann Ohira reagent (11.92 mL, 15.26 g, 79.42 mmol) at 0° C. After 10 min stirring, the ice-bath was removed, and the reaction mixture was stirred at 25° C. for 1 h. The reaction was followed by TLC. The reaction mixture was concentrated under reduced pressure. The resulting residue was quenched with water (100 mL) and extracted with EtOAc (250 mL×2). The combined organic layer was washed with brine (100 mL), dried over anhydrous sodium sulphate, filtered and concentrated under reduced pressure. The crude product was purified by flash column chromatography ($SiO_2$ 230-400 mesh; 5% EtOAc in pet ether) to obtain Int-105 as pale-yellow liquid. Yield=9.6 g (70%).

Step 6: To a stirred solution of Int-105 (9.5 g, 30.3 mmol) in toluene (100 mL), were added 4-bromo-1-iodobenzene (7, 10.29 g, 36.4 mmol), triethylamine (12.67 ml, 91 mmol) and copper (I) iodide (0.346 g, 1.818 mmol) at 25° C. and degassed with nitrogen for 15 min. To this reaction mixture, was added bis(triphenylphosphine)palladium (II) chloride (0.425 g, 0.606 mmol) and stirred for 1 h. The reaction as monitored by TLC (Hexane: EtOAc 95:5) showed complete consumption of starting material. The reaction was quenched by the addition of water (200 mL) and extracted with EtOAc (250 mL×2). The combined organic layers were washed with brine (200 mL), dried over anhydrous sodium sulphate, filtered and concentrated under reduced pressure. The resulting crude product was purified by flash column chromatography (SiO2 100-200 mesh size; 7% EtOAc in hexane) to obtain Int-106 as a brown color liquid as a 60:40 mixture of two epimers. Yield=11.03 g (77%) (before SFC; mixture of epimers). LC-MS: Calculated for $C_{22}H_{34}BrNO_3Si$ is 468.507, Observed: 412.0 $[M-56]^+$ and 414.0 $[M-56+2]^+$.

The isomers (11.03 g) were separated by SFC to obtain 106a (isomer 1) and 106b (isomer 2). Int-106a: Isomer 1: 3.0 g; Single enantiomer with unknown stereochemistry. Int-106b: Isomer 2: 6.9 g; Single enantiomer with unknown stereochemistry. Independently, both isomers (Int-106a and Int-106b) were taken on to the next step(s).

Step 7: To a stirred solution of Int-106a (3.0 g, 6.40 mmol) in DCM (30 mL), was added HCl (4.0 M in dioxane; 11.2 mL, 44.8 mmol) at 0° C. The reaction mixture was stirred at 25° C. for 6 h. The reaction was monitored by TLC. After completion of the reaction, the solids formed were filtered under vacuum, washed with hexane and dried under vacuum to afford Int-107a as an off-white solid. Yield=1.7 g (85%). LC-MS: Calculated for the ammonium salt $C_{11}H_{13}BrNO+$ is 254.24, Observed: 254.0 $[M]^+$ and 256 $[M+2]^+$.

Step 8: To a stirred solution of Int-107a (1.7 g, 5.85 mmol) in MeOH (17 mL), was added ammonium acetate (0.902 g, 11.70 mmol) at 25° C. and stirred for 10 min. To this reaction mixture was added Int-108 (3.70 g, 23.40 mmol); after 10 min stirring, added glyoxal (40% in water; 1.0 mL, 8.78 mmol). After 10 min stirring, the reaction mixture was heated at 80° C. for 2 h. The reaction was monitored by TLC. The reaction mixture was cooled to room temperature; quenched with water (20 mL) and extracted with DCM (150 mL×2). The combined organic layer was washed with ice cold water (50 mL), brine (25 mL), dried over anhydrous sodium sulphate, filtered and concentrated under reduced pressure. The resulting crude product was purified by flash column chromatography ($SiO_2$ 230-400 mesh; 5% Methanol in DCM) to obtain Int-109a as yellow color gum. Yield=1.5 g (58%). LC-MS: Calculated for $C_{21}H_{25}BrN_2O_3$ is 433.35, Observed: 433.0 [M] and 435.0 $[M+2]^+$.

Example 6: Preparation of 4-((4-bromophenoxy) methyl)-2,2-dimethyl-1,3-dioxolane (Int-25a)

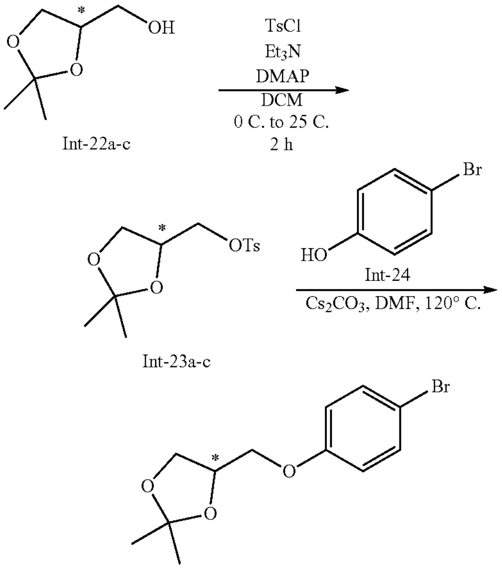

Int-22a-c
Int-23a-c
Int-25a-c a = racemic b = (S)-isomer and c = (R) isomer

Step 1: To a solution of (1,2-O-Isopropylideneglycerol (Int-22a, 1.0 g, 7.57 mmol) in DCM (10 mL), were added triethylamine (3.16 mL, 22.70 mmol), tosyl chloride (1.875 g, 9.84 mmol) and DMAP (92 mg, 0.757 mmol) at 0° C. The reaction mixture was then stirred at 25° C. for 2 h. The reaction was monitored by TLC, showed complete consumption of starting material. The reaction was quenched by the addition of saturated sodium bicarbonate solution, extracted with DCM (50 mL×2). The combined organic layers were washed with brine (50 mL), dried over anhydrous sodium sulphate, filtered and concentrated under reduced pressure. The resulting crude product was purified by flash column chromatography ($SiO_2$ 230-400 mesh; 15% EtOAc in pet ether) to obtain Int-23a as a white solid. Yield: 1.5 g (68%). LC-MS: Calculated for $C_{13}H_{18}O_5S$ is 286.34, Observed: 287.1 $[M+1]^+$.

Step 2: To a solution of Int-23a (384 mg, 1.75 mmol) in DMF (5 mL), was added cesium carbonate (569 mg, 1.75 mmol) at 25° C. under nitrogen atmosphere and stirred for 20 min. To this reaction mixture was added Int-24 (500 mg, 1.75 mmol) and heated at 90° C. for 4 h. The reaction was monitored by TLC, showed complete consumption of starting material. The reaction mixture was cooled to room temperature, quenched by the addition of ice-cold water (30 mL), extracted with DCM (50 mL×3). The combined organic layers were washed with brine (50 mL), dried over anhydrous sodium sulphate, filtered and concentrated under reduced pressure. The resulting crude product (600 mg) was purified by flash column chromatography ($SiO_2$ 230-400 mesh; 10% EtOAc in pet ether) to afford Int-25a. Yield: 250 mg (29%). LC-MS: Calculated for $C_{18}H_{27}BO_5$ is 334.21, Observed: 335.2 $[M+1]^+$ (64% by LCMS).

A similar strategy was carried out to synthesize (R) and (S) isomer derivatives from their appropriate chiral starting materials to afford Int-25b and Int-25c.

Example 7: Preparation of 5-((4-bromophenoxy) methyl)-2,2-dimethyl-1,3-dioxane (Int-28)

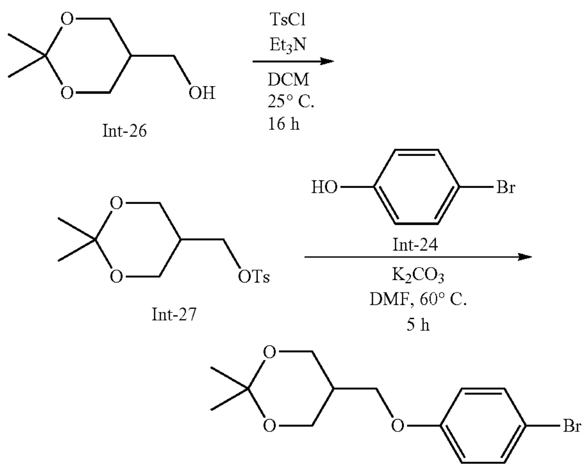

Int-26

Int-27

Int-28

Step 1: To a stirred solution of (2,2-dimethyl-1,3-dioxan-5-yl)methanol (Int-26) (5.0 g, 34.2 mmol) in DCM (50 mL) were added triethylamine (9.53 mL, 68.4 mmol) and p-toluenesulfonyl chloride (7.17 g, 37.6 mmol) at 25° C. After stirring for 16 h, the reaction mixture followed by TLC showed complete consumption of starting material. The reaction was quenched by the addition of water (50 mL) and extracted with DCM (50 mL×2). The combined organic layers were washed with brine (100 mL), dried over anhydrous sodium sulphate, filtered and concentrated under reduced pressure. The resulting crude product was purified by flash column chromatography ($SiO_2$; 230-400 mesh; 8-10% EtOAc in hexane) to afford Int-27 as a pale-yellow liquid. Yield: 8.0 g (78%). LCMS: Calculated for $C_{14}H_{20}O_5S$ is 300.37, Observed: 301.2 $[M+1]^+$.

Step 2: To a stirred solution of Int-27 (8.0 g, 26.6 mmol) in DMF (80 mL), were added potassium carbonate (8.1 g, 58.6 mmol) and 4-bromophenol (Int-24) (5.07 g, 29.3 mmol) at 25° C. Then the reaction mixture was heated at 60° C. for 5 h. The reaction was followed by TLC, showed complete consumption of starting material. The reaction was quenched by the addition of water (100 mL) and extracted with EtOAc (100 mL×2). The combined organic layers were washed with brine (100 mL), dried over anhydrous sodium sulphate, filtered and concentrated under reduced pressure. The resulting crude residue was purified by flash column chromatography (SiO2; 230-400 mesh; 8% EtOAc in hexane) to afford Int-28. Yield: 5.0 g (62%). LC MS: Calculated for $C_{13}H_{17}BrO_3$ is 301.18, Observed: 301.2 $[M]^+$ and 303.2 $[M+2]^+$.

Example 8: Preparation of tert-butyl 4-(((4-bromophenyl)oxy)methyl)-2,2-dimethyloxazolidine-3-carboxylate (Int-31a)

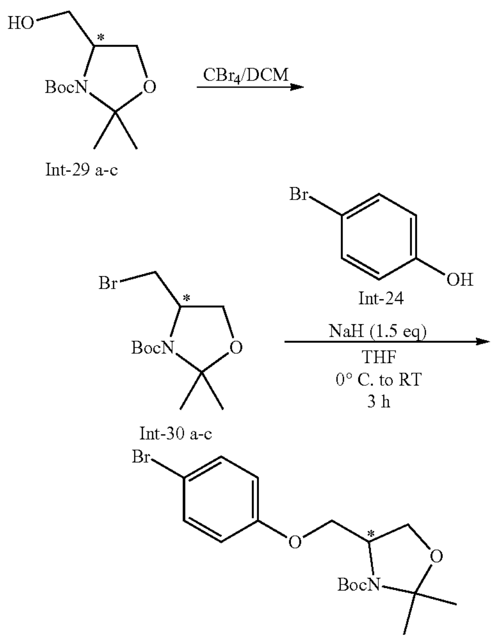

Int-29 a-c

Int-24

Int-30 a-c

Int-31 a-c a = racemic, b = (R)-isomer and c = (S)-isomer

Step 1: To a stirred solution of Int-29a (2.5 g, 0.0108 mol) in DCM (50 mL), $CBr_4$ (3.95 g, 0.012 mol) was added and stirred for a period of 6 h. After 6 h, the reaction mixture is diluted with DCM (25 ml) and washed with satd. $NaHCO_3$ (15 mL), followed by satd. NaCl (15 mL), dried ($Na_2SO_4$) and concentrated under vacuum. The crude mixture obtained as a yellow oil which yielded 78% was taken up to the next step without further purification. LC MS: Calculated for $C_{11}H_{20}BrNO_3$ is 294.19, Observed: Not observed Step 2: To a stirred solution of Int-30a (0.0064 mol) in dry THE (15 mL) and NaH (60% dispersion in mineral oil) (0.0097 mol) was added portion wise at 0° C. The reaction mixture was stirred at 0° C. for 30 minutes. Then 4-bromophenol (Int-24) (0.0084 mol) was dissolved in THE and slowly added to the reaction mixture, stirred at 0° C. for 30 minutes. Then reaction mixture was stirred at RT for 2 h. After the completion of the reaction, the reaction mixture was quenched with sat. $NH_4Cl$ solution, diluted with EtOAc (500 mL) and washed with ice cold water (200 mL), dried over anhydrous $Na_2SO_4$, filtered and concentrated under reduced pressure. The crude product was purified by column chromatography on silica gel (230-400 mesh) by eluting with 6-10% ethyl acetate in petrol ether to afford product Int-31a. Yield: 1.49 g (57.32%). LC MS: Calculated for $C_{17}H_{24}BrNO_4$ is 386.2, Observed: Not observed A similar strategy was carried out to synthesize (R) and (S) isomer derivatives from their appropriate chiral starting materials to afford Int-31b and Int-31c.

Example 9: Preparation of tert-butyl ((1S,2S)-2-(4-iodophenoxy)cyclopropyl)carbamate (Int-37a)

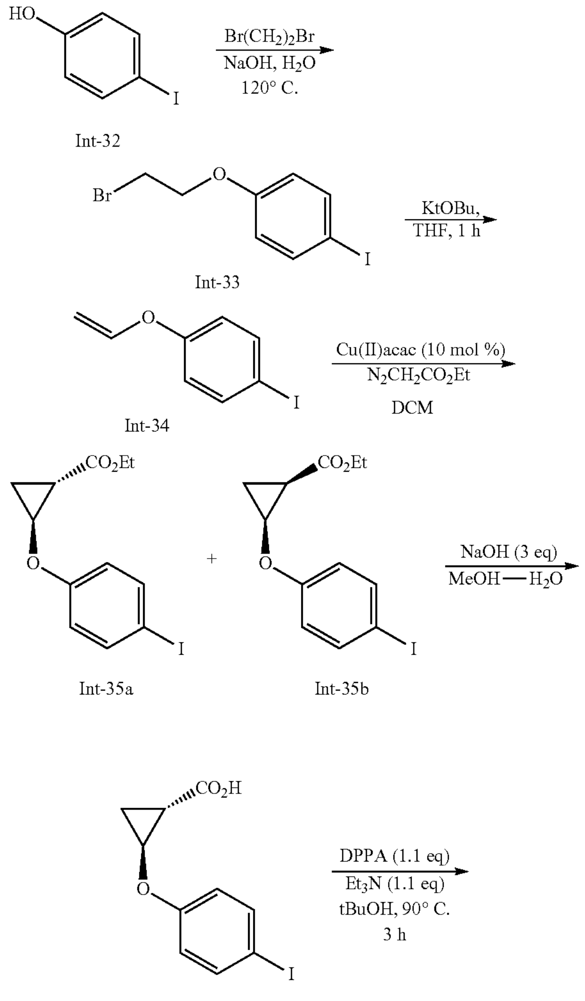

Int-32

Int-33

Int-34

Int-35a

Int-35b

Int-36a

-continued

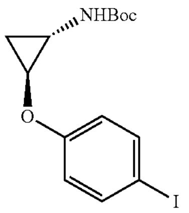

Int-37a

Step 1: To a stirred solution of 4-iodo phenol (Int-32 38 g, 172 mmol) in water (200 mL), NaOH (14.5 g, 362 mmol) and dibromoethane (162.2 g, 863 mmol) were added and the mixture was heated to 120° C. overnight. After completion of the reaction, reaction mass was extracted with EtOAc (1000 mL×2). The combined organic layers were dried over anhydrous $Na_2SO_4$ and concentrated under reduced pressure. The crude product was purified by column chromatography using silica gel (60-120 mesh) by eluting with ethyl acetate in pet. ether to afford pure product Int-33 as off solid. Yield: 53 g, (94%)

Step 2: To a stirred solution of Int-33 (67 g, 204 mmol) in THF (670 mL) was added t-BuOK (34.4 g, 307 mmol) and stirred at room temperature for 1 h. After completion of the reaction, reaction mass was diluted with water and extracted with EtOAc (1000 mL×2). The combined organic layers were dried over anhydrous $Na_2SO_4$ and concentrated under reduced pressure. The crude product was purified by column chromatography using silica gel (60-120 mesh) by eluting with ethyl acetate in pet ether to afford pure product Int-34 as a colorless liquid. Yield: 49 g, (97%).

Step 3: To a stirred solution of Int-34 (20 g, 81.3 mmol) in DCM (200 mL) and copper (II) acetyl acetonate (2.12 g, 8.13 mmol), ethyl diazo acetate (50.27 g, 440 mmol) was added through syringe pump at a rate of 0.2 mL/min at 0° C. After completion of the addition, the reaction mixture was stirred at room temperature 18 h. After completion of the reaction the DCM was removed under reduced pressure. The residue was dissolved in EtOAc (500 mL) and washed with water and brine solution. The organic layer was dried over anhydrous $Na_2SO_4$, filtered and concentrated under reduced pressure. The crude product was purified by column chromatography using silica gel (230-400 mesh) by eluting with 2-5% of ethyl acetate in pet. ether to afford Int-35a (trans; non-polar) & Int-35b (cis; polar) as a liquid. Yield: Compound Int-35a—11.7 g, (22%) and Compound Int-35b—28 g (contaminated with ethyl diazoacetate).

Step 4: To a stirred solution of Int-35a (38 g, 114 mmol) in water (200 mL) and MeOH (200 mL), NaOH (22.8 g, 570 mmol) was added and stirred at room temperature for 1 h. After the completion of the reaction, the reaction mixture was concentrated under reduced pressure, aqueous layer was washed with EtOAc (500 mL×2) and acidified the aqueous layer with dil HCl, extracted with EtOAc (500 mL×2). The combined organic layers were dried over anhydrous $Na_2SO_4$ and concentrated under reduced pressure. The crude product obtained Int-36a was used without further purification. Yield: 30 g, (88%). LC MS: m/z calculated for $C_{10}H_9IO_3$ is 304.08 Observed: 302.9 [M–H]+.

Step 5: To a stirred solution of Int-36a (30 g, 98.6 mmol) in dry t-BuOH (300 mL), were added TEA (15.1 mL, 108 mmol) and DPPA (29.9 g, 108 mmol) and stirred the reaction mixture at 90° C. for 3 h. After the completion of reaction, the reaction mixture was concentrated under reduced pressure, diluted with EtOAc (500 mL) and washed with $NaHCO_3$ and water. The organic layer was dried over anhydrous $Na_2SO_4$ and concentrated under reduced pressure to afford the crude product. The crude product was purified by column chromatography using silica gel (60-120 mesh and 230-400 mesh of 1:1 ratio) by eluting with 5-6% ethyl acetate in petrol ether to afford pure product Int-37a as off white solid. Yield: 26.6 g, (70%). LC MS: m/z calculated for $C_{14}H_{11}NO_3$ is 375.21, Observed: 276 $[M-100+H]^+$.

A similar strategy was carried out to prepare the cis derivative Int-35b from Int-37b.

Example 10: Preparation of (trans)-4-(4-bromophenoxy)tetrahydrofuran-3-ol (Int-39)

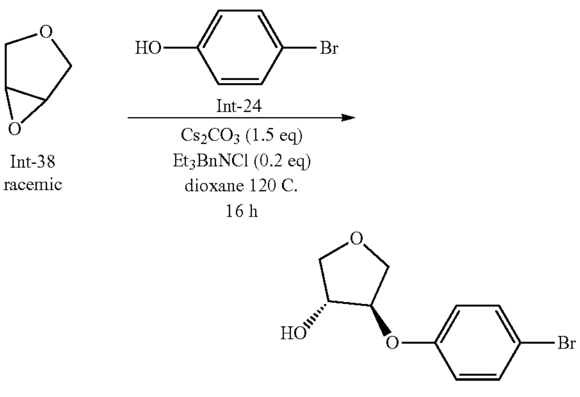

Int-38 racemic

Int-24

Int-39 racemic

Step 1: To a stirred solution of 4-bromophenol (Int-24) (4 g, 23.12 mmol) in 1,4-Dioxane (40 mL), were added 3,6-dioxabicyclo[3.1.0]hexane (Int-38, 1.98 g, 23.12 mmol), $Cs_2CO_3$ (11.3 g, 34.68 mmol) and Benzyltriethylammonium chloride (1.05 g, 4.62 mmol) at RT and the reaction mixture heated for 16 h at 120° C. After completion of the reaction, the reaction mixture was diluted in EtOAc (200 mL) and washed with sat. $NaHCO_3$ solution (100 mL), water (100 mL). The organic layer was dried over $Na_2SO_4$ and concentrated under reduced pressure. The crude product was triturated with petroleum ether and dried to afford Int-39. Yield: 5 g, (84%). LC-MS: Calculated for $C_{10}H_{11}BrO_3$ is 259.10, Observed: no ionization observed. trans and cis isomers were separated to provide Int-39a and Int-39b respectively.

Example 11: Preparation of tert-butyl ((trans)-4-(4-bromophenoxy)tetrahydrofuran-3-yl)carbamate (Int-45)

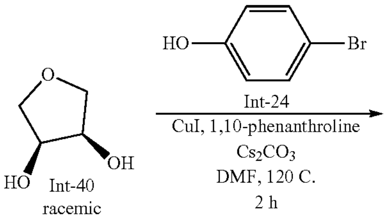

Int-24

Int-40 racemic

-continued

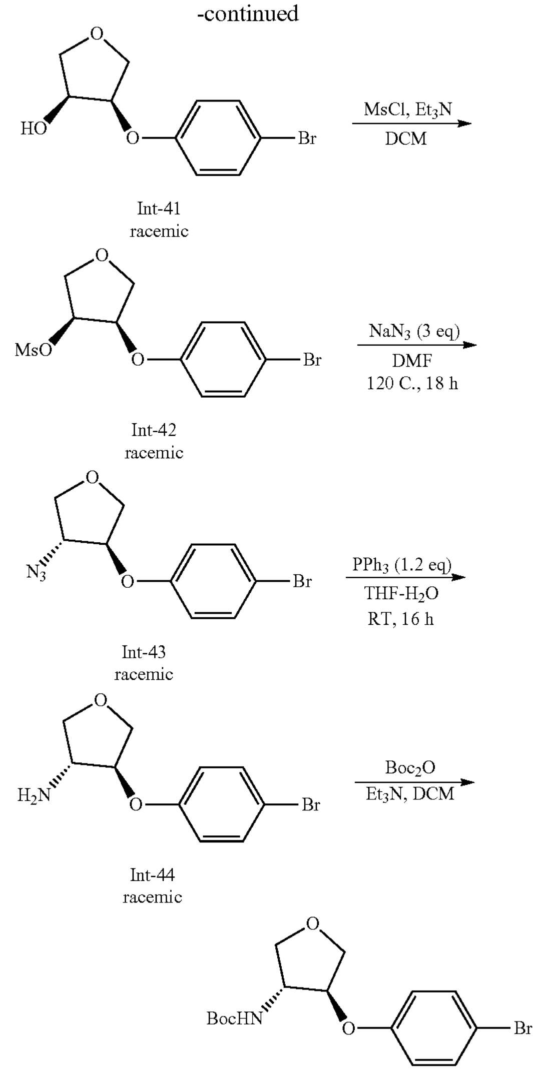

Int-41 racemic

Int-42 racemic

Int-43 racemic

Int-44 racemic

Int-45 racemic

Step 1: To a stirred solution of 4-bromophenol (Int-24) (4 g, 23.12 mmol) in 1,4-Dioxane (40 mL), were added 3,6-dioxabicyclo[3.1.0]hexane (Int-40, 1.98 g, 23.12 mmol), $Cs_2CO_3$ (11.3 g, 34.68 mmol) and benzyltriethylammonium chloride (1.05 g, 4.62 mmol) at RT and the reaction mixture heated for 16 h at 120° C. After completion of the reaction, the reaction mixture was diluted in EtOAc (200 mL) and washed with sat. $NaHCO_3$ solution (100 mL), water (100 mL). The organic layer was dried over $Na_2SO_4$ and concentrated under reduced pressure. The crude product was triturated with petroleum ether and dried to afford Int-41. Yield: 5 g, (84%). LC-MS: Calculated for $C_{10}H_{11}BrO_3$ is 259.10, Observed: no ionization observed.

Step 2: To a stirred solution of Int-1 (0.600 g, 2.31 mmol) in DCM (6 mL), were added $Et_3N$(0.5 mL, 3.47 mmol) and Mesyl Chloride (0.2 mL, 2.54 mmol) at 0° C. and the reaction mixture stirred at RT for 1 h. After completion of the reaction, the reaction mass was diluted with DCM (50 mL) and then washed with water (20 mL). The organic layer was dried over $Na_2SO_4$ and concentrated under reduced pressure. The crude mesylate Int-42 was used in the next step without any further purification. Yield: 0.75 g (Crude). LC-MS: Calculated for $C_{11}H_{13}BrO_5S$ is 337.18, Observed: mass was not ionized.

Step 3: To a stirred solution of the mesylate (Int-42, 0.750 g, 2.22 mmol) in DMF (10 mL), was added sodium azide (0.433 g, 6.67 mmol) at RT and the reaction mixture heated for 18 h at 120° C. After completion of the reaction, the reaction mass was dissolved in water and extracted with EtOAc (2×50 mL). The combined organic layers were washed with brine (50 mL), the organic layer dried over $Na_2SO_4$ and concentrated under reduced pressure. The crude product Int-43 was used in the next step without any further purification. Yield: 0.600 g, (Crude).

Step 4: To a stirred solution of Int-43 (0.600 g, 2.11 mmol) in THE (9 mL) and water (3 mL), was added $PPh_3$ (0.663 g, 2.53 mmol) at 0° C. and the reaction mixture stirred at RT for 16 h. After completion of the reaction, the reaction mixture was concentrated under reduced pressure. The resulting residue was acidified with 1.5 N HCl and extracted with EtOAc. The aqueous layer was basified with 10% NaOH solution and extracted with EtOAc (2×50 mL). The combined organic layers were dried over $Na_2SO_4$ and concentrated under reduced pressure to afford crude product Int-44 which was used in the next step without any further purification.

Yield: 0.22 g (40%). LC-MS: Calculated for $C_{10}H_{12}BrNO_2$ is 258.12, Observed: 258 [M] and 260.0 $[M+2]^+$.

Step 5: The stirred solution of Int-44 (0.220 g, 0.852 mmol) in dry DCM (3 mL) were added $Et_3N$(0.35 mL, 2.55 mmol) and $(Boc)_2O$ (0.3 mL, 1.279 mmol) at 0° C. and the reaction mixture stirred at RT for 2 h. After completion of the reaction, the reaction mixture was diluted with dichloromethane (40 mL) and washed with water (20 mL). The organic layer was dried over anhydrous $Na_2SO_4$, filtered and concentrated under reduced pressure to afford crude product Int-45 which was used in the next step without any further purification. Yield: 0.250 g (Crude).

Example 12: Preparation of (R)-1-(4-bromophenoxy)-3-methoxypropan-2-ol (Int-47)

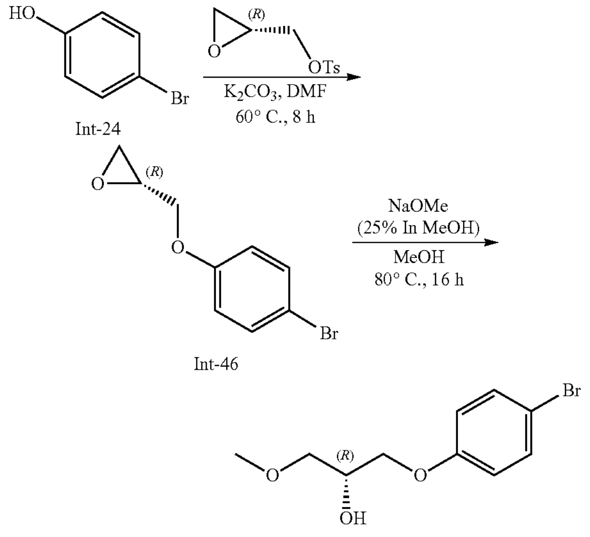

Int-24

Int-46

Int-47

Step 1: To a stirred solution of 4-bromophenol (Int-24, 10.0 g, 57.80 mmol) in DMF (100 mL), were added $K_2CO_3$ (9.59 g, 69.40 mmol) and (R)-Glycidyl tosylate (13.19 g, 57.8 mmol) at room temperature. The reaction mixture stirred at 60° C. for 8 h. The reaction was monitored by TLC; after completion of reaction, it was cooled to room temperature, quenched with water (200 mL) and extracted with EtOAc (300 mL×2). The combined organic layers were washed with brine (200 mL), dried over anhydrous sodium sulphate, filtered and concentrated under reduced pressure. The resulting crude product was purified by flash column chromatography (SiO2 100-200 mesh size 20-30% EtOAc in hexane) to obtain Int-46 (10 g, 43.7 mmol, 76% yield) as a colourless oil. Yield=10.0 g (76%). LC MS: Calculated for $C_9H_9BrO_2$ is 229.07, Observed: No ionization observed Step 2: To a stirred solution of Int-46 (10.0 g, 43.70 mmol) in MeOH (100 mL), were added 25% sodium methoxide in MeOH (48.9 mL, 214.00 mmol) at 25° C. and the reaction mixture stirred at 80° C. for 16 h. The reaction was monitored by TLC. After completion of reaction, it was cooled to room temperature, quenched with water (200 mL) and extracted with EtOAc (300 mL×2). The combined organic layers were washed with brine (200 mL), dried over anhydrous sodium sulphate, filtered and concentrated under reduced pressure to obtain Int-47 as a colourless liquid. Yield: 10.0 g (88%). LC MS: Calculated for $C_{10}H_{13}BrO_3$ is 261.12, Observed: No ionization observed.

Example 13: Preparation of (R)-1-(4-bromophenoxy)-3-methoxypropan-2-ol (Int-51)

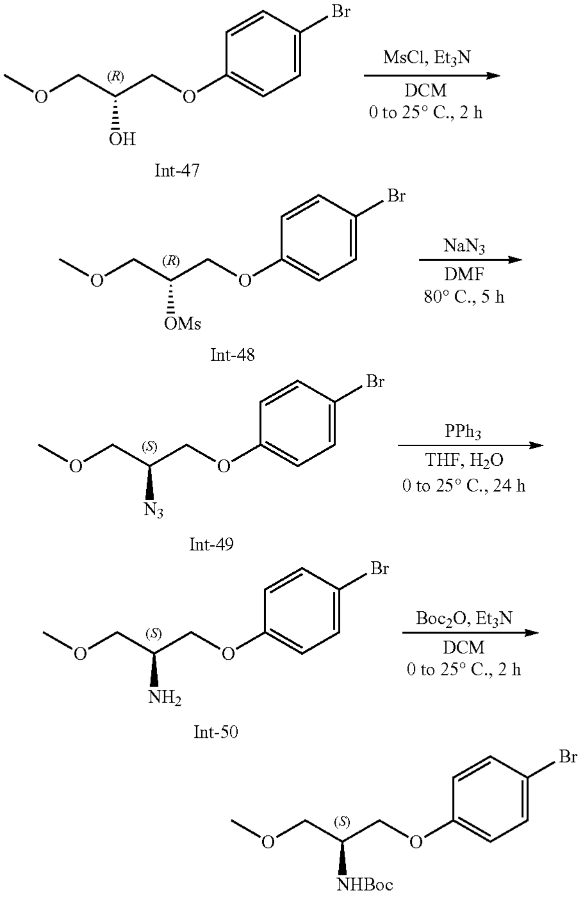

Int-47

Int-48

Int-49

Int-50

Int-51

Step 1: To a stirred solution of Int-47 (9.0 g, 34.50 mmol) in DCM (135 mL), were added $Et_3N$(9.62 mL, 68.90 mmol) and mesyl chloride (3.20 mL, 41.40 mmol) at 0° C. and the reaction mixture stirred at RT for 2 h. The reaction was monitored by TLC. After completion of reaction, the reaction mixture was quenched with water (200 mL) and extracted with DCM (200 mL×2). The combined organic layers were washed with brine (200 mL), dried over anhydrous sodium sulphate, filtered and concentrated under reduced pressure to obtain Int-48 as a colourless liquid. The crude material was used in next step without any further purification. Yield: 9.0 g (77%). LC MS: Calculated for $C_{11}H_{15}BrO_5S$ is 339.20, Observed: No ionization observed.

Step 2: To a stirred solution of Int-48 (3.0 g, 8.84 mmol) in DMF (30 mL), was added sodium azide (2.9 g, 44.20 mmol) at RT. The reaction mixture was heated for 5 h at 80° C. After completion, the reaction was cooled to RT and quenched by the addition of water (150 mL) and extracted with EtOAc (100 mL×2). The combined organic layers were washed with brine (30 mL), dried over anhydrous $Na_2SO_4$ and concentrated under reduced pressure to give Int-49 as a colourless liquid. The crude product 6 was used in the next step without any further purification. Yield: 2.50 g, (99%). LC MS: Calculated for $C_{10}H_{12}BrN_3O_2$ is 286.13, Observed: 258 (M-$N_2$)+ and 260 (M-$N_2$+2)$^+$ and 180 (M-$N_2$—Br)*. Total three batches of step 2 were carried out. The combined product was taken up for next step.

Step 3: To a stirred solution of Int-49 (7.50 g, 26.20 mmol) in THF (75 mL) and water (37.5 mL), was added triphenylphosphine (8.25 g, 31.5 mmol) at 0° C. The reaction mixture was stirred at 25° C. for 24 h. After completion of the reaction, the reaction mixture was concentrated under reduced pressure. The resulting residue was acidified with 1.5 N HCl and extracted with EtOAc (30 mL×2). The aqueous layer was basified with 10% NaOH solution and extracted with 10% MeOH in DCM (100 mL×2). The combined organic layers were dried over $Na_2SO_4$ and concentrated under reduced pressure to afford Int-50. The crude product was taken up for next step without any further purification. Yield: 5 g (73%).

Step 4: The stirred solution of Int-50 (5.0 g, 19.22 mmol) in DCM (75 mL) were added triethylamine (8.04 mL, 557.7 mmol) and Boc-anhydride (6.62 mL, 28.80 mmol) at 0° C. and the reaction mixture stirred at 25° C. for 2 h. After completion of the reaction, the reaction mixture was diluted with dichloromethane (50 mL) and washed with water (50 mL). The organic layer was dried over anhydrous $Na_2SO_4$, filtered and concentrated under reduced pressure to afford Int-51 a pale-yellow liquid. The crude product was used in the next step without any further purification. Yield: 6.50 g (78%). LC MS: Calculated for $C_{15}H_{22}BrNO_4$ is 360.25, Observed: 260.2 [M-Boc]$^+$ and 262.2 [M-Boc+2].

Example 14: Preparation of 6-(4-bromophenoxy)-2,2,3,3,10,10,11,11-octamethyl-4,9-dioxa-3,10-disiladodecane (Int-54)

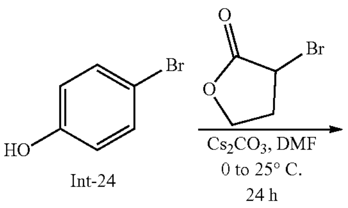

-continued

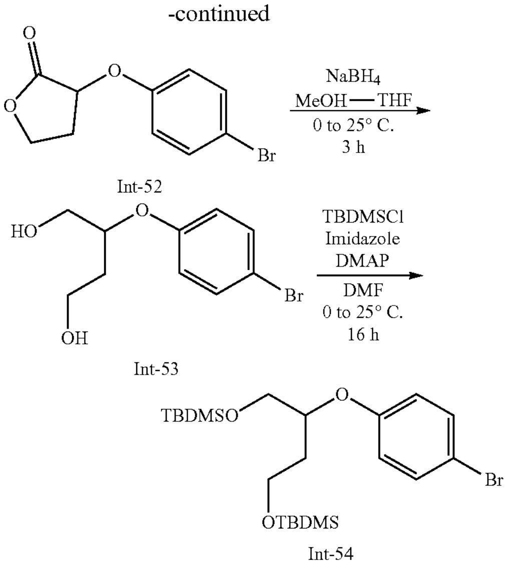

Step 1: To a stirred solution of 4-bromophenol (Int-24) (2.0 g, 11.56 mmol) in DMF (20 mL), was added cesium carbonate (5.65 g, 17.34 mmol) at 0° C. and stirred for 5 min. To this reaction mixture, was added α-bromo-γ-butyrolactone (2.67 g, 16.18 mmol) at 0° C. and the reaction mixture stirred at 25° C. for 24 h. The reaction was monitored by TLC, showed complete consumption of starting material. The reaction was quenched with the addition of ice-cold water (100 mL) and extracted with EtOAc (50 mL×2). The combined organic layer was washed with brine (30 mL), dried over anhydrous sodium sulphate, filtered and concentrated at reduced pressure. The resulting crude product was purified by flash column chromatography (SiO2 230-400 mesh size; 15-20% EtOAc in pet ether) to obtain Int-52 as a white solid. Yield=2.1 g (71%). LC MS: Calculated for $C_{10}H_9BrO_3$ is 257.08, Observed: No ionization observed.

Step 2: To a stirred solution of Int-52 (2.1 g, 8.17 mmol) in a mixture of THF:MeOH (1:1; 40 mL), was added sodium borohydride (0.309 g, 8.17 mmol) in portions under nitrogen atmosphere at 0° C. The resulting reaction mixture was stirred at 25° C. for 3 h. The reaction was followed by TLC, showed complete consumption of starting material. The reaction was quenched with the addition of the ice water (20 mL), volatiles evaporated under reduced pressure. The resulting residue was extracted with EtOAc (40 mL×3). The combined organic layers were washed with brine (50 mL), dried over anhydrous sodium sulphate, filtered and concentrated under reduced pressure. The resulting crude product was purified by flash column chromatography (SiO2 230-400 mesh; 60% EtOAc in hexane) to obtain Int-53 as a pale-yellow liquid. Yield=2.0 g (94%). LC MS: Calculated for $C_{10}H_{13}BrO_3$ is 261.12, Observed: No ionization observed.

Step 3: To a stirred solution of Int-53 (2.0 g, 7.66 mmol) in DMF (20 mL), were added imidazole (1.56 g, 22.98 mmol), DMAP (0.19 g, 1.53 mmol) and TBDMS-Cl (2.89 g, 19.15 mmol) at 0° C. After the addition, the reaction was stirred at 25° C. for 16 h. The reaction was followed by TLC, showed complete consumption of starting material. The reaction mixture was diluted with water (100 mL) and extracted with EtOAc (250 mL×2). The combined organic layer was washed with cold water (200 mL×2) and brine (100 mL), dried over anhydrous sodium sulfate, filtered and concentrated under reduced pressure. The crude was purified by column chromatography (SiO2 100-200 mesh size; 5% EtOAc in hexane) to afford Int-54 as a yellow liquid. Yield=2.8 g (75%) LC MS: Calculated for $C_{22}H_{41}BrO_3Si_2$ is 489.64, Observed: No ionization observed.

Example 15: Preparation of 5-(4-bromophenoxy)pentane-1,4-diol (Int-57)

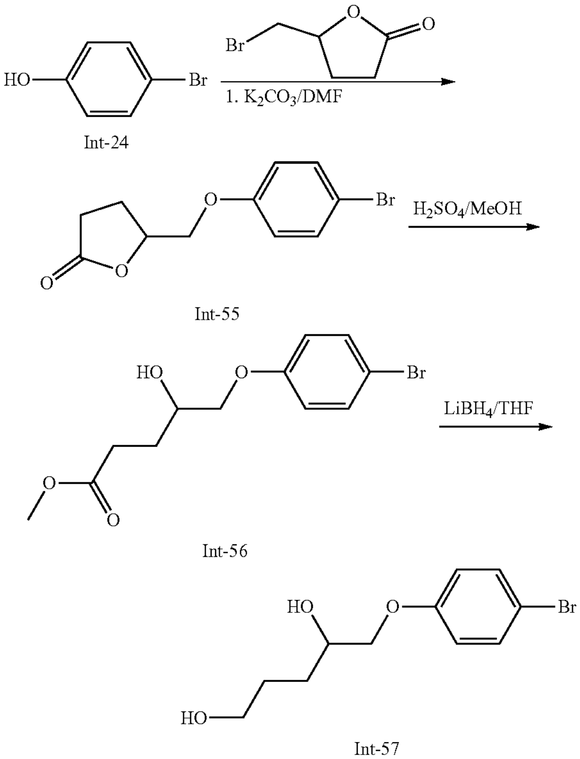

Int-24

Int-55

Int-56

Int-57

Step 1: To a stirred solution of 4-bromophenol (Int-24) (11.56 mmol) in DMF (20 mL), was added potassium carbonate (17.34 mmol) at 0° C. and stirred for 5 min. To this reaction mixture, was added 5-(bromomethyl)dihydrofuran-2(3H)-one (16.18 mmol) at 0° C. and the reaction mixture stirred at 25° C. for 24 h. The reaction was monitored by TLC, showed complete consumption of starting material. The reaction was quenched with the addition of ice-cold water (100 mL) and extracted with EtOAc (50 mL×2). The combined organic layer was washed with brine (30 mL), dried over anhydrous sodium sulphate, filtered and concentrated at reduced pressure. The resulting crude product was purified by flash column chromatography (SiO2 230-400 mesh size; 15-20% EtOAc in pet ether) to obtain Int-55 as a white solid. Yield=65%. LC MS: Calculated for $C_{11}H_{11}BrO_3$ is 271.11, Observed: No ionization observed.

Step 2: To a stirred solution of Int-55 (16.0 mmol) in Methanol (50 mL), $H_2SO_4$ (7 mL) was added and heated at 60° C. for a period of 2 h. The reaction is concentrated under vacuum. The reaction mixture was cooled and carefully poured into ice-cold water and basified with Satd. $NaHCO_3$ solution. The aqueous layer was extracted with EtOAc (50 mL×2). The combined organic layer was washed with brine (30 mL), dried over anhydrous sodium sulphate, filtered and concentrated at reduced pressure. The resulting crude product was purified by flash column chromatography ($SiO_2$ 230-400 mesh size; 50% EtOAc in pet ether) to obtain Int-56 as a white solid. Yield=56%.

Step 3: To a stirred solution of Int-56 (7.00 mmol) in a mixture of THF:MeOH (8:2; 40 mL), was added lithium borohydride (7.00 mmol) in portions under nitrogen atmosphere at 0° C. The resulting reaction mixture was stirred at 25° C. for 3 h. The reaction was followed by TLC, showed complete consumption of starting material. The reaction was quenched with the addition of the ice water (20 mL), volatiles evaporated under reduced pressure. The resulting residue was extracted with EtOAc (40 mL×3). The combined organic layers were washed with brine (50 mL), dried over anhydrous sodium sulphate, filtered and concentrated under reduced pressure. The resulting crude product was purified by flash column chromatography ($SiO_2$ 230-400 mesh; 60% EtOAc in hexane) to obtain Int-57 as a pale-yellow liquid. Yield=82%. LC MS: Calculated for $C_{11}H_{15}BrO_3$ is 275.14, Observed: No ionization observed.

Example 16: Preparation of 4-(4-bromophenyl)-2,2-dimethyl-1,3-dioxolane (Int-59)

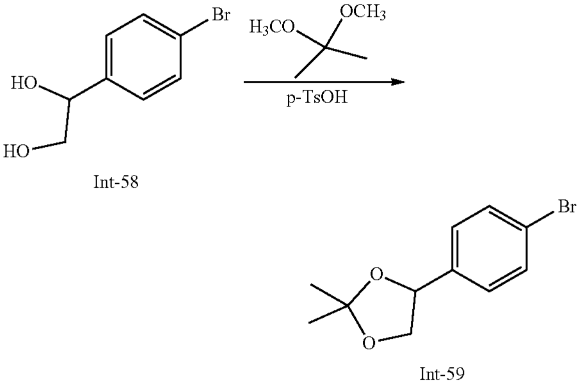

Int-58

Int-59

To as stirred solution of 1-(4-Bromophenyl)-1,2-ethanediol (Int-58) (500 mg, 2.3 mmol) was dissolved in 15 mL of 2,2-dimethoxypropane. A catalytic amount of p-toluenesulfonic acid was added and the solution was stirred at 50° C. for 18 h. After addition of 50 mL of toluene the resulting mixture was washed with a saturated solution of $NaHCO_3$. The organic phase was collected and dried over $MgSO_4$, the solvent completely removed. The procedure yielded Int-59 compound, which was used without any further purification Yellow oil, yield 521 mg. Yield=88%. LC MS: Calculated for $C_{11}H_{13}BrO_2$ is 257.12, Observed: No ionization observed.

Example 17: Preparation of 2-(3-(4-bromophenyl)azetidin-1-yl)-2-oxoethyl acetate (Int-61)

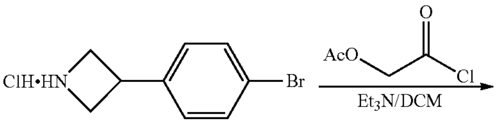

Int-60

-continued

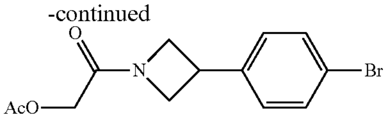

Int-61

To a stirred solution of the Int-60 (500 mg, 2.00 mmol) in DCM (10 ml), triethylamine (0.700 ml, 2.5 eq) was added followed by the addition of the acetoxyacetyl chloride (0.328 g, 2.41 mmol, 1.2 eq) and stirred for a period of 45 minutes. TLC indicated completion of the reaction. The reaction mixture was poured into water (15 ml) and extracted with DCM (2×25 mL). The combined organic layer was washed with 3 M HCl soln (10 mL), satd. $NaHCO_3$ (15 mL), satd. NaCl solution (25 mL), dried ($Na_2SO_4$) and concentrated to dryness. The crude Int-61 was isolated as a yellow oil which yielded (95%) and was taken up to the next without further purification. LC MS: Calculated for $C_{13}H_{14}BrNO_3$ is 312.0, Observed: No ionization observed.

Example 18: Preparation of N-((trans)-3-(4-bromophenyl)cyclobutyl)methanesulfonamide (Int-63) and N-((1r,3r)-3-(4-bromophenyl)cyclobutyl)-2-cyanoacetamide (Int-110)

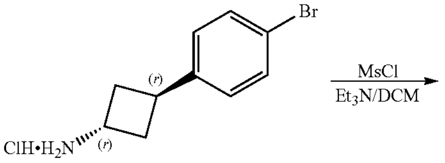

Int-62

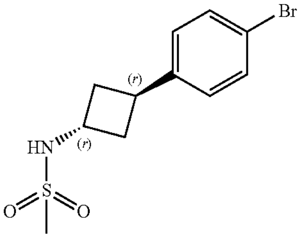

Int-63

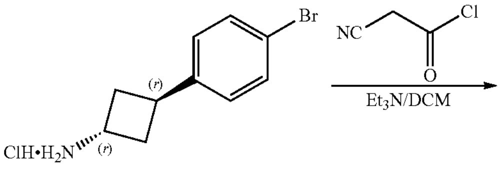

Int-62

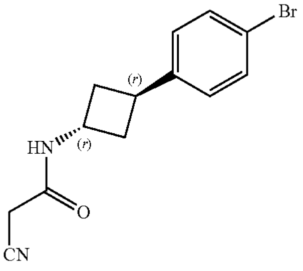

Int-110

To a stirred solution of the Int-62 (500 mg, 1.90 mmol) in DCM (15 ml), triethylamine (0.67 mL, 4.76 mmol, 2.5 eq) was added followed by the addition of the methylsulfonyl chloride (0.260 g, 2.28 mmol, 1.2 eq) and stirred for a period of 45 minutes. TLC indicated completion of the reaction. The reaction mixture was poured into water (15 ml) and extracted with DCM (2×20 mL). The combined organic layer was washed with 3M HCl (10 mL), satd. $NaHCO_3$ (15 mL), satd. NaCl solution (20 mL), dried ($Na_2SO_4$) and concentrated to dryness. The crude Int-63 was obtained as a yellow oil yielding (90%) was taken up to the next without further purification.

To a stirred solution of the Int-62 (500 mg, 1.90 mmol) in DCM (15 ml), triethylamine (0.67 mL, 4.76 mmol, 2.5 eq) was added followed by the addition of the 2-cyanoacetyl chloride (0.300 g, 2.28 mmol, 1.2 eq) and stirred for a period of 45 minutes. TLC indicated completion of the reaction. The reaction mixture was poured into water (15 ml) and extracted with DCM (2×20 mL). The combined organic layer was washed with 3M HCl (10 mL), satd. $NaHCO_3$ (15 mL), satd. NaCl solution (20 mL), dried ($Na_2SO_4$) and concentrated to dryness. The crude Int-110 was obtained as a yellow oil yielding (90%) was taken up to the next without further purification.

Example 19: Preparation of 4,4,5,5-tetramethyl-2-(4-(((3R,4S)-4-((tetrahydro-2H-pyran-2-yl)oxy)tetrahydrofuran-3-yl)methyl)phenyl)-1,3,2-dioxaborolane (Int-118)

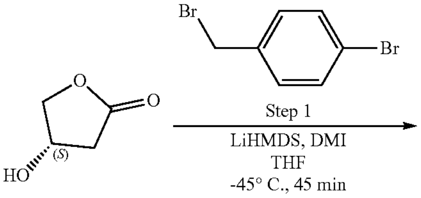

Int-111

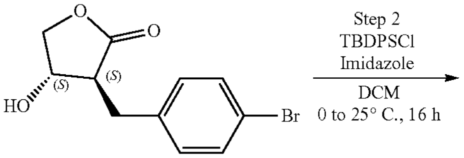

Int-112

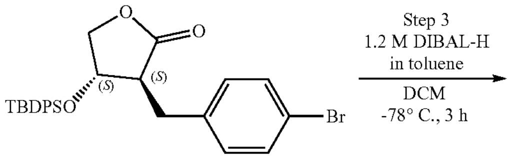

Int-113

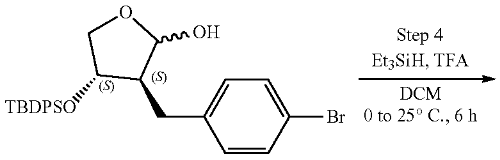

Int-114

-continued

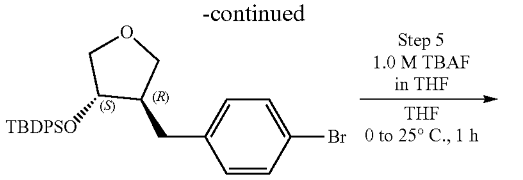

Int-115

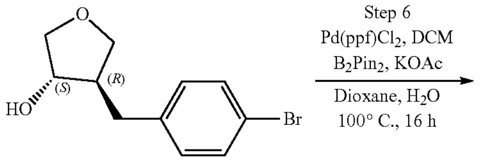

Int-116

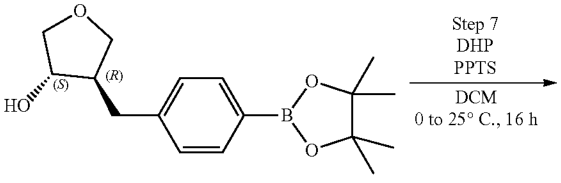

Int-117

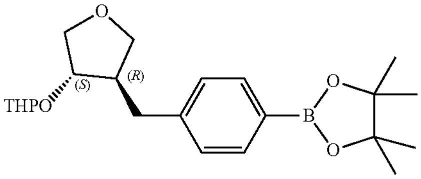

Int-118

Step-1: To a solution of LiHMDS (1.0 M in THF; 245 mL, 245 mmol) in THE (90 mL), was added (S)-4-hydroxydihydrofuran-2(3H)-one (Int-111, 10 g, 98 mmol) at −45° C. under nitrogen atmosphere and stirred for 30 min. To this reaction mixture, were added a solution of 1-bromo-4-(bromomethyl)benzene (29.4 g, 118 mmol) and in THE (90 mL) followed by 1,3-dimethyl-2-imidazolidinone (28.6 mL, 264 mmol) at −45° C. After stirring for 45 min at the same temperature, the reaction mixture was quenched by the addition of saturated ammonium chloride solution (100 mL). This was extracted with EtOAc (400 mL×2). The combined organic layers were washed with brine (100 mL), dried over anhydrous $Na_2SO_4$, filtered and concentrated under reduced pressure. The resulting crude was purified by flash column chromatography ($SiO_2$ 100-200 mesh; 45% EtOAc in hexanes) to afford Int-112 as an off-white solid. Yield: 15 g (56%). LC MS: Calculated for $C_{11}H_{11}BrO_3$ is 271.11, Observed: 271.0 $[M]^+$ and 273.0 $[M+2]^+$ The assignment of absolute stereochemistry is based on U.S. Pat. No. 6,268,515.

Step-2: To a stirred solution of Int-112 (15 g, 55.3 mmol) in DCM (150 mL), were added imidazole (7.53 g, 111 mmol) followed by TBDPS-Cl (21.32 mL, 83 mmol) at 0° C. The reaction mixture was stirred at 25° C. for 16 h. The reaction was quenched with water (150 mL) and extracted with DCM (300 mL×3). The combined organic layer was washed with brine (100 mL), dried over anhydrous $Na_2SO_4$, filtered and concentrated under reduced pressure. The crude product was purified by flash column chromatography ($SiO_2$ 100-200 mesh; 5% EtOAc in hexane) to afford Int-113 as a colorless liquid. UPLC showed 68% purity; the product was taken to the next step. Yield: 35 g (84%). LC MS: Calculated for $C_{27}H_{29}BrO_3Si$ is 509.51, Observed: 526 $[M+OH]^+$ and 528 $[M+OH+2]^+$, 509.1 $[M]^+$ and 511.1 $[M+2]^+$.

Step-3: To a stirred solution of Int-113 (35 g, 34.3 mmol) in DCM (30 mL), was added DIBAL-H (1.2 M in toluene; 48.7 mL, 58.4 mmol) at −78° C. under nitrogen atmosphere. The resulting reaction mixture was stirred at −78° C. for 3 h. The reaction was quenched with $NH_4Cl$ solution (350 mL) and extracted with DCM (800 mL×2). The combined organic layer was washed with brine (200 mL), dried over anhydrous $Na_2SO_4$, filtered and concentrated under reduced pressure. The crude product was purified by flash column chromatography ($SiO_2$ 100-200 mesh; 18% EtOAc in Hexanes) to afford Int-114 as a colourless gum. Yield: 17 g. LC MS: Calculated for $C_{27}H_{31}BrO_3Si$ is 511.53, Observed: 510.9 $[M]^+$.

Step-4: To a solution of Int-114 (17 g, 33.2 mmol) in DCM (200 mL), was added TFA (26.8 mL, 166 mmol) at 0° C. and the reaction mixture stirred for 30 min. To this reaction mixture was added triethylsilane (5.12 mL, 66.5 mmol) at 0° C. The reaction mixture was stirred at 25° C. for 6 h. After complete consumption of starting material, the reaction was quenched with water (300 mL) and extracted with DCM (300 mL×2). The combined organic layer was washed with brine (100 mL), dried over anhydrous $Na_2SO_4$, filtered and concentrated under reduced pressure. The resulting crude product was purified by flash column chromatography ($SiO_2$ 100-200 mesh; 11% EtOAc in hexane) to afford Int-115 as a colourless liquid. Yield: 10.1 g (61%).

Step-5: To a stirred solution of Int-115 (10.1 g, 20.38 mmol) in THE (100 mL), was added TBAF (1.0 M in THF; 30.6 mL, 30.6 mmol) dropwise at 0° C. The reaction mixture was stirred at 25° C. for 1 h. The reaction mixture was diluted with water (200 mL) and extracted with EtOAc (250 mL×2). The combined organic layer was washed with brine (100 mL), dried over anhydrous $Na_2SO_4$, filtered and concentrated under reduced pressure. The resulting residue was purified by flash column chromatography ($SiO_2$ 100-200 mesh; 60% EtOAc in hexane) to afford Int-116 as white solid. Yield: 4.9 g (91%).

Step-6: To a stirred solution of Int-116 (4.8 g, 18.67 mmol) in dioxane (130 mL), were added KOAc (5.5 g, 56.0 mmol) and bis(pinacolato)diboron (7.11 g, 28.0 mmol) at 25° C. The reaction mixture was degassed with nitrogen for 10 min. To this reaction mixture, was added Pd(dppf)$Cl_2$·DCM complex (1.52 g, 1.86 mmol) and stirred at 110° C. for 16 h. The reaction mixture was diluted with EtOAc (100 mL), filtered through Celite bed and the Celite bed was washed with EtOAc (50 mL). To the filtrate, was added water (100 mL), extracted with EtOAc (100 mL×2). The combined organic layers were washed with brine (100 mL), dried over anhydrous $Na_2SO_4$, filtered and concentrated under reduced pressure to give the crude product. The crude product was purified by flash column chromatography ($SiO_2$ 230-400 mesh; 50% EtOAc in hexanes) to afford Int-117 as pale-yellow liquid. Yield: 4.8 g (84%). LC MS: Calculated for $C_{17}H_{25}BO_4$ is 304.19, Observed: 305.4 $[M+1]^+$.

Step-7: To a solution of Int-117 (5.1 g, 16.77 mmol) in DCM (120 mL), were added 3,4-dihydro-2H-pyran (2.3 mL, 25.1 mmol) and pyridinium p-toluene sulphonate (0.33 g, 1.34 mmol) at 0° C. The reaction mixture was stirred at 25° C. for 16 h. The reaction was quenched with water (50 mL) and extracted with DCM (100 mL). The combined organic layer was washed with brine solution (50 mL), dried over anhydrous $Na_2SO_4$, filtered and concentrated under reduced pressure to get crude product. The crude was purified by flash column chromatography ($SiO_2$ 230-400 mesh; 15% EtOAc in hexane) to afford Int-118 as colorless liquid. Yield: 4.4 g (66%).

Example 20: Preparation of (3R,4R)-1-(2-methoxyethyl)-4-(4-(4,4,5,5-tetramethyl-1,3,2-dioxaborolan-2-yl)phenoxy)pyrrolidine-3-ol (Int-121) and 2-((3R,4R)-3-hydroxy-4-(4-(4,4,5,5-tetramethyl-1,3,2-dioxaborolan-2-yl)phenoxy)pyrrolidine-1-yl) acetonitrile (Int-122)

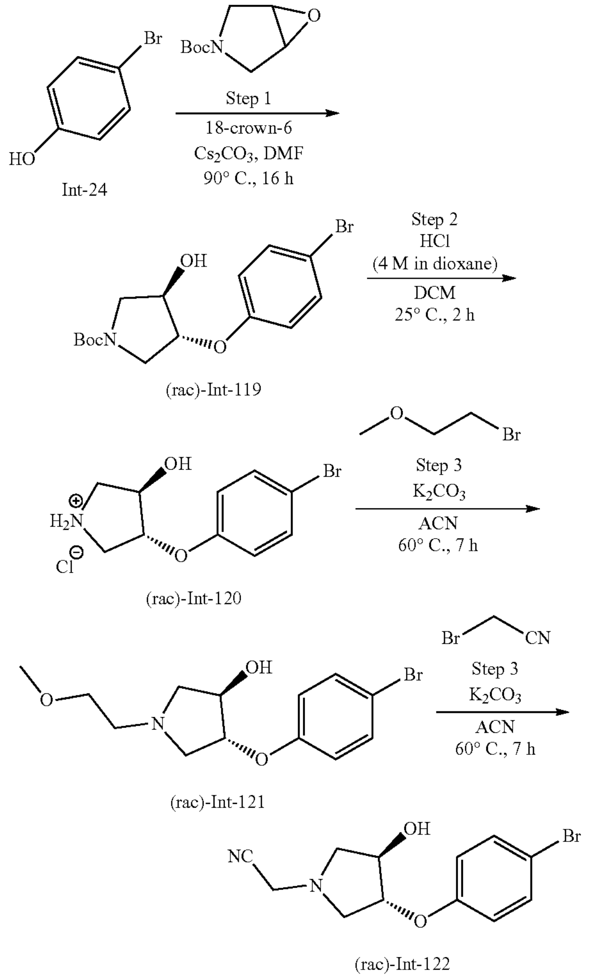

Step 1: To a stirred solution of 4-bromophenol (Int-24, 12 g, 69.4 mmol) in DMF (100 mL), were added 18-crown-6 (0.055 g, 0.208 mmol), cesium carbonate (27.1 g, 83 mmol) at room temperature. After 10 min, to this reaction mixture, was added tert-butyl 6-oxa-3-azabicyclo[3.1.0]hexane-3-carboxylate (10.28 g, 55.5 mmol) and stirred at 90° C. for 16 h. The reaction was quenched with ice water (200 mL) and the precipitates formed were filtered, washed with hexane, dried under vacuum to afford (rac)-Int-119 as a brown solid. LC-MS: Calculated for $C_{15}H_{20}BrNO_4$ is 358.23, observed: 257.8 $[M\text{-}Boc]^+$, 259.8 $[M\text{-}Boc+2]^+$, 301.8 $[M-56]^+$, 303.7 $[M-56+2]^+$. Yield: 18.0 g (72%).

Step 2: To a stirred solution of (rac)-Int-119 (4.5 g, 11.30 mmol) in DCM (40 mL), was added HCl (4 M in dioxane, 10 mL, 11.72 mmol) at 0° C. The reaction mixture was stirred at 25° C. for 2 h. The progress of the reaction was monitored by TLC showed complete consumption of the starting material (10% MeOH in DCM; SM stains purple, and the product yellow with ninhydrin).). The volatiles were evaporated under reduced pressure and the resulting crude product was triturated with hexane (20 mL), filtered and dried under vacuum to afford (rac)-Int-120 as a pale brown solid. LC MS: Calculated for $C_{10}H_{13}BrNO_2+$ is 258.01, Observed: 258.0 $[M]^+$ and 260.0 $[M+2]^+$ Yield: 3.45 g (99%).

Step 3a: To a stirred solution of (rac)-Int-120 (1.8 g, 6.11 mmol) in acetonitrile (20 mL), were added potassium carbonate (573 mg, 4.15 mmol) and 1-bromo-2-methoxyethane (0.636 mL, 6.72 mmol) at 0° C. The reaction mixture was heated at 60° C. for 7 h. The progress of the reaction was monitored by TLC. The volatiles were evaporated under reduced pressure, added water (50 mL) and extracted with DCM (150 mL×2). The combined organic layer was washed with brine (20 mL), dried over anhydrous sodium sulphate, filtered and concentrated under reduced pressure to afford (rac)-Int-121 as a brown Liquid. LCMS: Calculated for $C_{13}H_{18}BrNO_3$ is 316.2, Observed: 315.9 $[M]^+$ and 317.9 $[M+2]^+$. Yield: 1.2 g (58%).

The same method as above was followed for making the nitrile derivative using bromoacetonitrile in 6.11 mmol scale to give the desired (rac)-Int-122 as a brown liquid. Yield 1.3 g (62%). LCMS: Calculated for $C_{12}H_{13}BrN_2O_2$ is 296.15, Observed: 297.9 $[M]^+$ and 299.9 $[M+2]^+$.

Example 21: Preparation of 4-(4,4,5,5-tetramethyl-1,3,2-dioxaborolan-2-yl)phenol (Int-66)

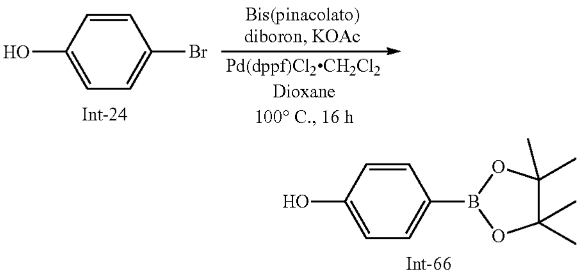

Step 1: To a stirred solution of Int-24 (2.0 g, 9.09 mmol) in 1,4-dioxane (20 mL), were added bis(pinacolato)diboron (3.46 g, 13.64 mmol) and potassium acetate (2.2 g, 22.73 mmol) at room temperature. The reaction mixture was degassed using nitrogen gas for 10 min. To this mixture, was added $Pd(dppf)Cl_2$ (665 mg, 0.91 mmol) and degassing continued for 2 min. The reaction mixture was then heated at 90° C. for 4 h. The reaction was monitored by TLC; TLC showed complete consumption of starting material. The reaction was filtered through Celite bed. The filtrate was diluted with EtOAc (100 mL), washed with water (50 mL), brine (50 mL), dried over sodium sulphate, filtered and concentrated under reduced pressure. The resulting crude product (2.5 g) was purified by flash column chromatography (SiO2 230-400 mesh; 5% EtOAc in pet ether) to obtain Int-66 as a white solid. Yield=1.8 g (82%). LC-MS: Calculated for $C_{12}H_{17}BO_3$ is 220.08, Observed: 218.9 $[M-1]^+$.

The following compounds were prepared according to Example 21 using the appropriate starting material. Int-80 was prepared from commercially available 4-bromophenylcyclobutanone (Int-64). Int-81 was prepared from commercially available (4-bromophenyl)methanol (Int-65).

| Intermediate | Structure | Starting Material |
|---|---|---|
| Int-67a; Int-67b; Int-67c | 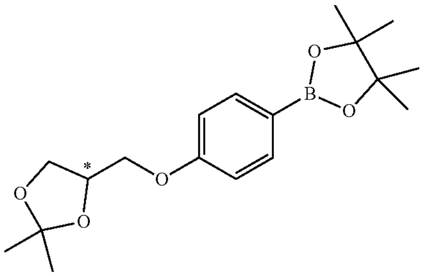 | Int-25a; Int-25b; Int-25c |
| Int-68 | 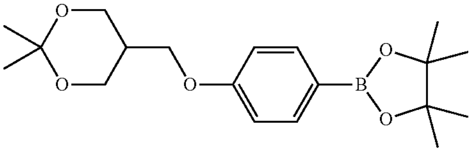 | Int-28 |
| Int-69a; Int-69b; Int-69c | 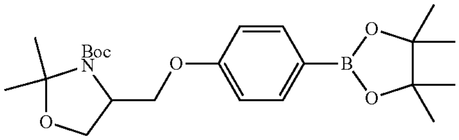 | Int-31a; Int-31b; Int-31c |
| Int-70a; Int-70b | 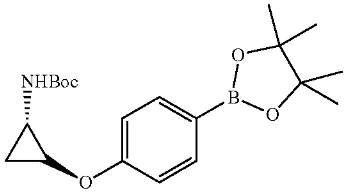 | Int-37a; Int-37b |
| Int-71a | 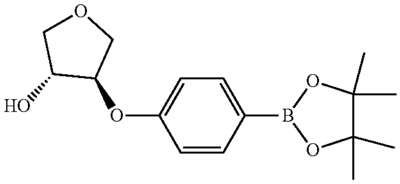 [SMILES: CC1(C)OB(c2ccc(O[C@@H]3COC[C@H]3O)cc2)OC1(C)C] | Int-39a |
| Int-71b | 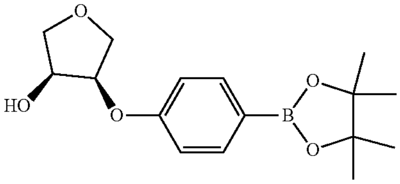 [SMILES: CC1(C)OB(c2ccc(O[C@@H]3COC[C@@H]3O)cc2)OC1(C)C] | Int-39b |
| Int-72 | 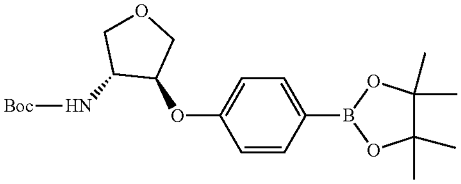 [SMILES: CC(C)(C)OC(=O)N[C@@H]1COC[C@H]1Oc1ccc(B2OC(C)(C)C(C)(C)O2)cc1] | Int-45 |
| Int-73 | 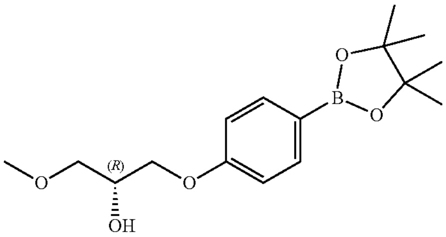 | Int-47 |

-continued
| Intermediate | Structure | Starting Material |
|---|---|---|
| Int-74 | 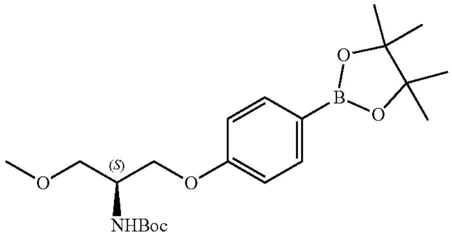 | Int-51 |
| Int-75 | 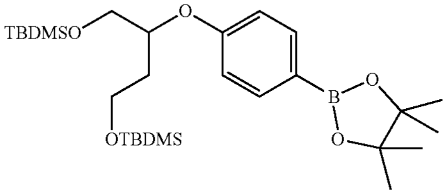 [SMILES: CC1(C)OB(c2ccc(OC(CCO[Si](C)(C)C(C)(C)C)CO[Si](C)(C)C(C)(C)C)cc2)OC1(C)C] | Int-54 |
| Int-76 | 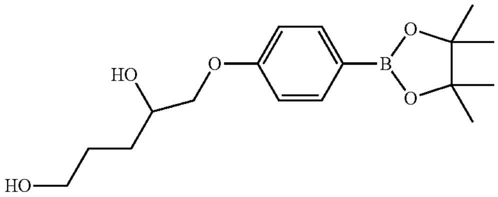 [SMILES: CC1(C)OB(c2ccc(OCC(O)CCCO)cc2)OC1(C)C] | Int-57 |
| Int-77 | 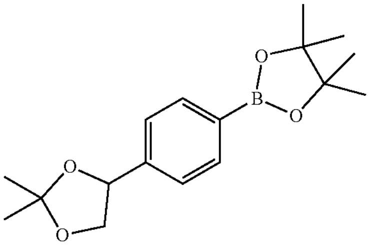 | Int-59 |
| Int-78 | 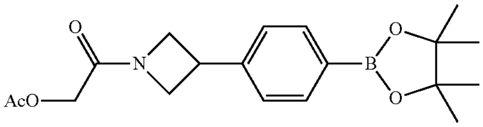 [SMILES: CC(=O)OCC(=O)N1CC(c2ccc(B3OC(C)(C)C(C)(C)O3)cc2)C1] | Int-61 |
| Int-79 | 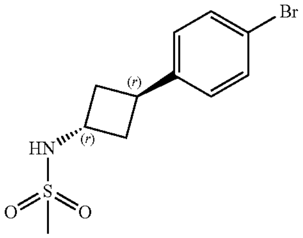 [SMILES: CS(=O)(=O)N[C@H]1C[C@H](c2ccc(Br)cc2)C1] | Int-63 |

-continued
| Intermediate | Structure | Starting Material |
|---|---|---|
| Int-123 | 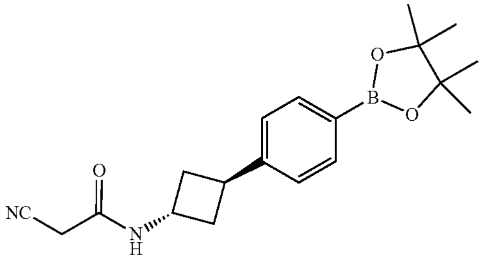 [SMILES: CC1(C)OB(c2ccc([C@H]3C[C@H](NC(=O)CC#N)C3)cc2)OC1(C)C] | Int-110 |
| Int-80 | 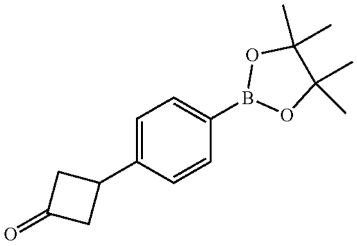 [SMILES: CC1(C)OB(c2ccc(C3CC(=O)C3)cc2)OC1(C)C] | 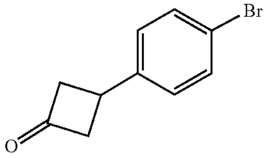 [SMILES: O=C1CC(c2ccc(Br)cc2)C1] (Int-64) |
| Int-81 | 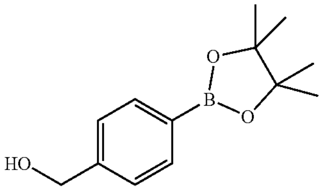 [SMILES: CC1(C)OB(c2ccc(CO)cc2)OC1(C)C] | 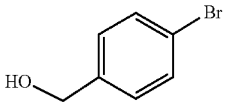 (Int-65) |
| Int-124 | 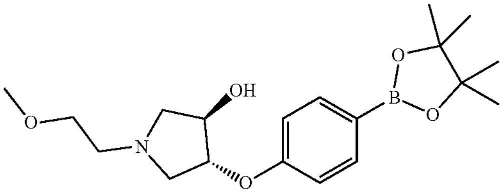 | Int-121 |
| Int-125 | 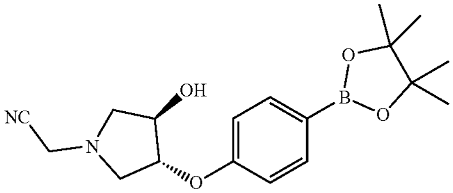 [SMILES: CC1(C)OB(c2ccc(O[C@@H]3CN(CC#N)C[C@H]3O)cc2)OC1(C)C] | Int-122 |

Example 19: Preparation of tert-butyl (2-fluoroethyl)((1R,2R)-2-(4-(4,4,5,5-tetramethyl-1,3,2-dioxaborolan-2-yl)phenoxy)cyclopropyl)carbamate (Int-82)

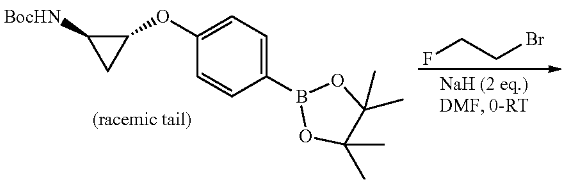

Int-70a

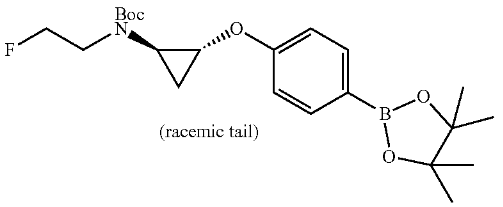

Int-82

To a stirred solution of Int-70a (0.5 g, 1.33 mmol) in dry DMF (5 mL), was added NaH (60% dispersion in mineral oil, 0.106 g, 2.66 mmol) at 0° C. Then 1-Bromo-2-fluoroethane (0.253 g, 1.99 mmol) was added and the reaction mixture was stirred at 0° C. to 25° C. for 2 h. After completion of the reaction, the reaction mixture was quenched with sat. $NH_4Cl$ solution, diluted with EtOAc (50 mL) and washed with ice cold water (20 mL), dried over anhydrous $Na_2SO_4$, filtered and concentrated under reduced pressure. The crude product was purified by column chromatography on silica gel (230-400 mesh) by eluting with 6-20% ethyl acetate in petroleum ether to afford product Int-82. Yield: 0.4 g (71%). LC-MS: Calculated for C22H33BFNO5 is 421.32, Observed: 366.1 $[M-56+1]^+$.

Example 20: Preparation of Certain Compounds of Formula (I) Via Suzuki Reaction

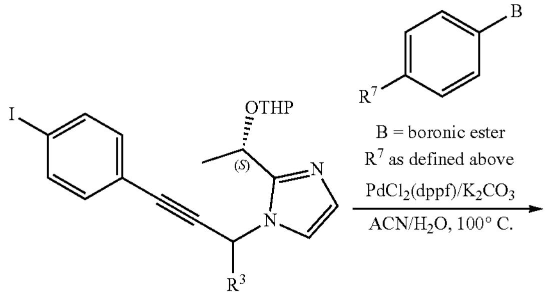

Int-9: $R^3$ = H
Int-15: $R^3$ = $CH_2OH$
Int-21: $R^3$ = $CH_2NHBoc$

-continued

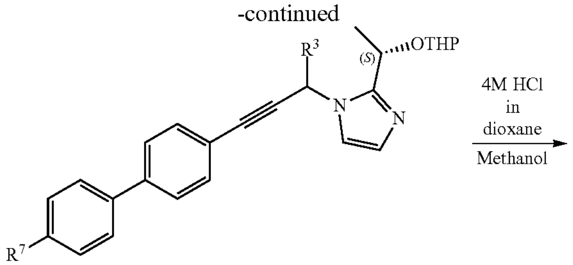

Int-83: $R^3$ = H
Int-84: $R^3$ = $CH_2OH$
Int-85: $R^3$ = $CH_2NHBoc$

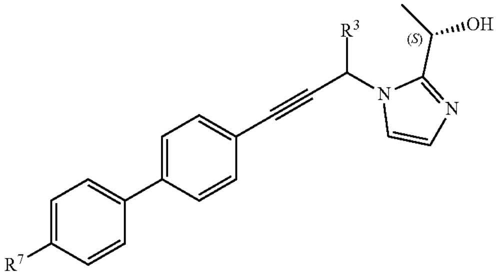

Certain Compounds of Formula (I)

Step 1: To a stirred solution of appropriate aryl iodide (Int-9, Int-15, or Int-21) (0.45 mmol) in DMF (1 mL), were added an appropriate aryl boronic ester intermediate (see Example 18) (0.32 mmol), potassium phosphate tribasic (0.96 mmol) and water (0.5 mL) at room temperature. The reaction mixture was degassed with nitrogen gas for 5 min. To this reaction mixture was added $PdCl_2$(dppf) (11.7 mg, 0.02 mmol) and degassing continued for 2 min. The reaction mixture was then subjected to microwave irradiation at 100° C., for 3 h. After completion of the reaction, the inorganic solids were filtered through Celite pad. The filtrate was diluted in EtOAc (50 mL) and washed with water (30 mL), brine (30 mL), dried over anhydrous sodium sulphate, filtered and concentrated under reduced pressure. The resulting crude product was purified by flash column chromatography ($SiO_2$ 230-400 mesh; 3% MeOH in DCM) to afford intermediates Int-83, Int-84, and Int-85 compounds.

Some of the Int-83, Int-84, and Int-85 compounds were deprotected to give the desired final compounds:

Step 2: To a stirred solution of the Int-83, Int-84, and Int-85 compound (0.219 mmol) in DCM (2 mL), was added 4.0 M HCl in dioxane (1 mL) at 0° C. The reaction mixture was then stirred for 2 h at 25° C. The reaction was monitored by TLC, showed complete consumption of starting material. The volatiles were evaporated under reduced pressure. The resulting crude product was purified by reversed phase preparative HPLC (10 mM ammonium bicarbonate in water and acetonitrile) to afford desired Certain Compounds of Formula (I) as a white solid. Yields ranged between 28-45%.

Step 2a: In some cases, an alternative procedure was used to give the desired compounds. For example, to a stirred solution of Int-83 (200 mg, 0.267 mmol) in DCM (5 mL), was added trifluoroacetic acid (1.4 mL) in drop wise fashion at 0° C. After complete addition, the reaction mixture was stirred at 25° C. for 2 h. The reaction was followed by TLC. The volatiles were evaporated under reduced pressure. The resulting residue was basified with saturated sodium bicarbonate solution (10 mL) and extracted with DCM (10 mL×2). The combined organic layers were washed with water (10 mL), brine (10 mL), dried over anhydrous sodium sulphate, filtered and concentrated under reduced pressure. The resulting crude compound was purified by reversed phase preparative HPLC (10 mM ammonium bicarbonate buffer and acetonitrile) to afford Certain Compounds of Formula (I) as an off-white solid. Yield=13-40%.

The following compounds were prepared according to Example 20:

| Compound No. | Aryl Iodide | Boronic Ester | Mass $[M+H]^+$ |
|---|---|---|---|
| 1 | Int-15 | Int-69a | 422.5 |
| 2 | Int-15 | Int-69b | 422.5 |
| 3 | Int-15 | Int-74 | 436.5 |
| 4 | Int-15 | Int-70a | 404.4 |
| 5 | Int-15 | Int-77 | 393.5 |
| 7 | Int-9 | Int-69a | 392.5 |
| 8 | Int-15 | Int-67b | 423.5 |
| 10 | Int-15 | Int-71a | 435.5 |
| 11 | Int-15 | Int-68 | 437.24 |
| 12 | Int-15 | Int-82 | 450.5 |
| 14 | Int-15 | Int-73 | 437.5 |
| 15 | Int-15 | Int-72 | 434.5 |
| 21 | Int-15 | Int-78 | 437.2 |
| 22 | Int-15 | Int-75 | 437.2 |
| 23 | Int-15 | Int-76 | 451.4 |
| 24 | Int-21 | Int-71a | 434.5 |
| 36 | Int-15 | Int-79 | 480.2 |
| 40 | Int-15 | Int-123 | 469.4 |
| 41 | Int-15 | Int-118 | 433.3 |
| 42 | Int-9 | Int-71a | 405.4 |
| 43 | Int-109a | Int-71a | 449.5 |
| 44 | Int-15 | Int-121 | 492.4 |
| 45 | Int-15 | Int-122 | 473.5 |
| 46 | Int-15 | Int-71b | 469.4 |

For some compounds, final derivatizations were carried out before deprotection to give the desired final targets. For example, hydrolysis of the acetyl group protecting group was done using NaOH in THF and water before deprotection.

Example 21: Preparation of Certain Compounds of Formula (I) Via O-Alkylation of Intermediate Int-84

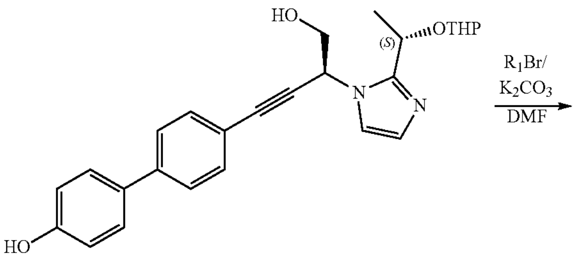

Int-84

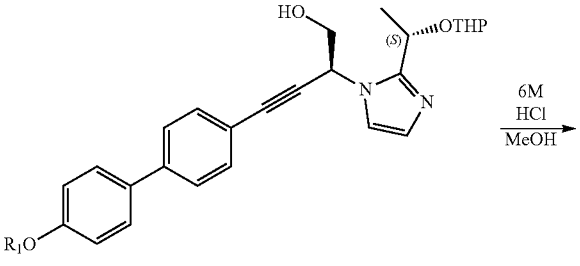

Int-86a-c

-continued

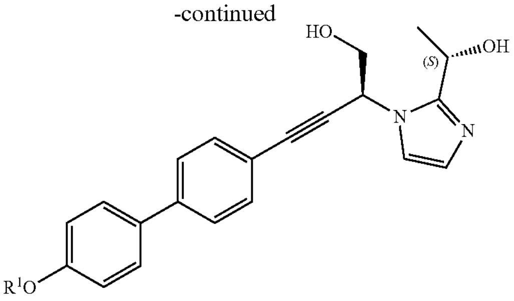

Certain compounds of Formula I

Step 1: To a stirred solution of Int-84 (1.50 g, 6.58 mmol) in DMF (7 mL) was added $K_2CO_3$. The reaction mixture was stirred at 30 minutes. To this, corresponding alkyl halide (6.58 mmol) was added and heated at 80° C. for a period of 8 h. After completion of the reaction, the reaction mixture poured into ice cold water and extracted with Ethyl acetate. The aqueous layer was further extracted with Ethyl acetate (50 mL×2). The combined organic layer was dried over anhydrous sodium sulphate, filtered and concentrated under reduced pressure. The resulting crude was purified by flash column chromatography ($SiO_2$ 100-200 mesh size, 0-5% methanol in DCM) to afford the intermediate compounds Int-86a-c as solids. Yield 30-45%.

Step 2: To a stirred solution of Int-86a-c (0.2476 mmol) in dry DCM (2 mL), was added HCl (4 M in 1,4-Dioxane, 2 mL) at 0° C. The reaction mixture was stirred at 0° C. to RT for 1 h. After the completion of the reaction, the reaction mixture was concentrated under reduced pressure to afford the crude product. The crude product was purified by using 0.1% HCOOH in $H_2O$ and ACN to afford desired Certain Compounds of Formula (I) as off white semi-solids. Yields ranged between 23.5-50%.

The following compounds were prepared according to Example 21:

| Compound No. | Alkyl halide | Mass $[M+H]^+$ |
|---|---|---|
| 13 | 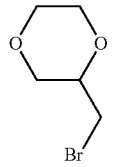 (a) | 449.54 |
| 16 | 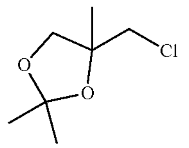 (b) | 437.2 |
| 17 | 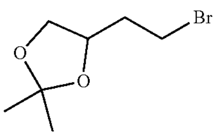 (c) | 437.2 |

Example 22: Preparation of Certain Compounds of Formula (I) Via Reductive Amination Starting with Cyclobutanone Intermediate Int-87/88)

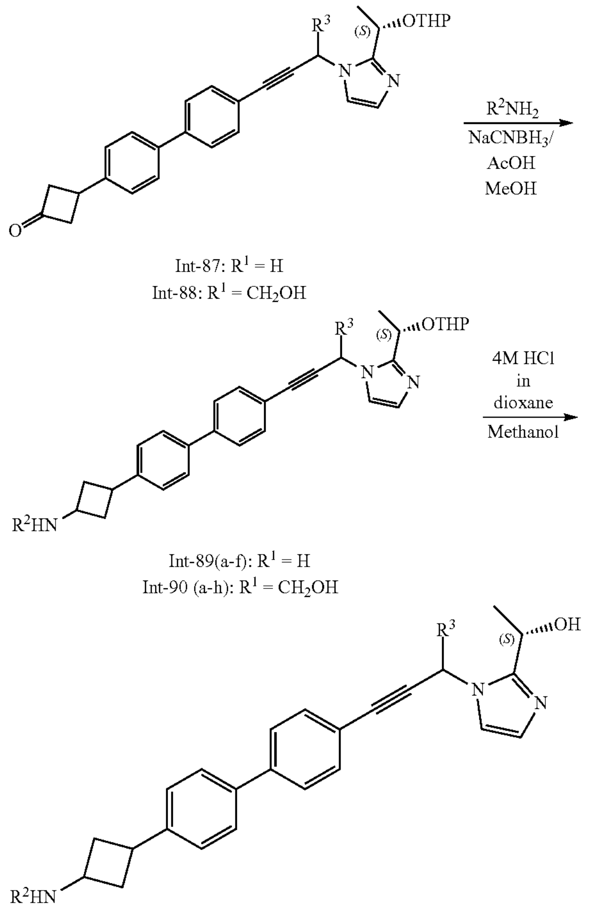

Int-87: $R^1$ = H
Int-88: $R^1$ = $CH_2OH$

Int-89(a-f): $R^1$ = H
Int-90 (a-h): $R^1$ = $CH_2OH$

Certain Compounds of Formula (I)

Step 1: The same procedure of Step 1 of Example 20 was followed to prepare Int-87 and Int-88 using appropriate Int-9 or Int-15 along with Int-80.

Step 2: To a stirred solution of Int-87 (or Int-88) (60 mmol) in methanol (10 mL), and appropriate respective amine ($R^2NH_2$) was added (78 mmol, 1.3 eq) followed by a drop of acetic acid. The reaction was stirred for a period of 45 minutes. To this sodium cyanoborohydride (66 mol, 1.1 eq) was added and the reaction was stirred for a period of 4 h. After 4 h reaction mixture was concentrated, diluted with water and extracted with ethyl acetate (2×25 mL). The organic layer was washed with satd. NaCl (15 mL), dried $MgSO_4$ and concentrated to give the crude product of Int-89 (or Int-90). Yields ranged between 75-90%. The reaction mixture is taken up to the next step without further purification.

Step 3: To a stirred solution of Int-89 (or Int-90) (50 mmol) in methanol (5 mL), was added 4 M HCl in dioxane (1.0 mL) at 0° for 30 minutes. The reaction was monitored by TLC, showed complete consumption of starting material. After completion of reaction, the volatiles were evaporated under reduced pressure. The resulting crude product was purified by reversed phase preparative HPLC (10 mM ammonium bicarbonate buffer and acetonitrile) to afford desired Certain Compounds of Formula (I). Yields ranged between 57-89%.

The following compounds were prepared according to Example 21:

| Compound No. | Ketone | Amine | Mass $[M + H]^+$ |
|---|---|---|---|
| 18 | Int-9 | 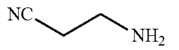 | 425.5 |
| 19 | Int-9 | 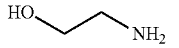 | 416.5 |
| 20 | Int-9 | 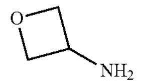 | 428.5 |
| 25 | Int-9 | 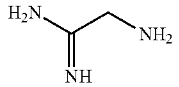 | 428.5 |
| 26 * | Int-9 | 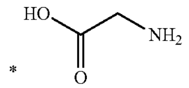 | 430.4 |
| 27 | Int-9 | 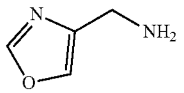 | 453.5 |
| 28 | Int-15 | 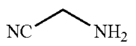 | 441.5 |
| 29 | Int-15 | 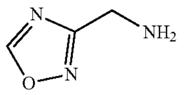 | 484.4 |
| 30 ** | Int-15 | ** | 403.5 |
| 31 | Int-15 | 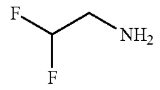 | 466.5 |
| 32 | Int-15 | 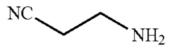 | 455.5 |
| 33 | Int-15 | 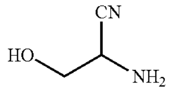 | 471.5 |
| 34 | Int-15 | 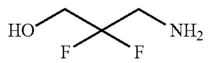 | 496.5 |
| 35 | Int-15 | 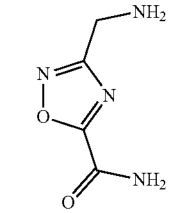 | 527.5 |
| 37* | Int-15 | 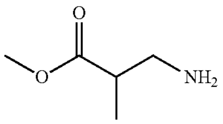 | 488.1 |

-continued

| Compound No. | Ketone | Amine | Mass [M + H]+ |
|---|---|---|---|
| 38 | Int-15 | 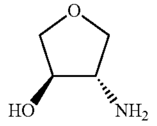 | 488.5 |
| 39 | Int-15 | 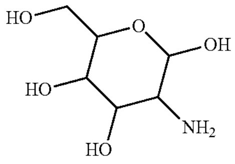 [SMILES: NC1C(O)OC(CO)C(O)C1O] | 564.6 |

* Ester hydrolysis using NaOH in water and THF afforded the acid before deprotection.

** Ketone reduction to alcohol directly using $NaBH_4$ before deprotection.

Example 22

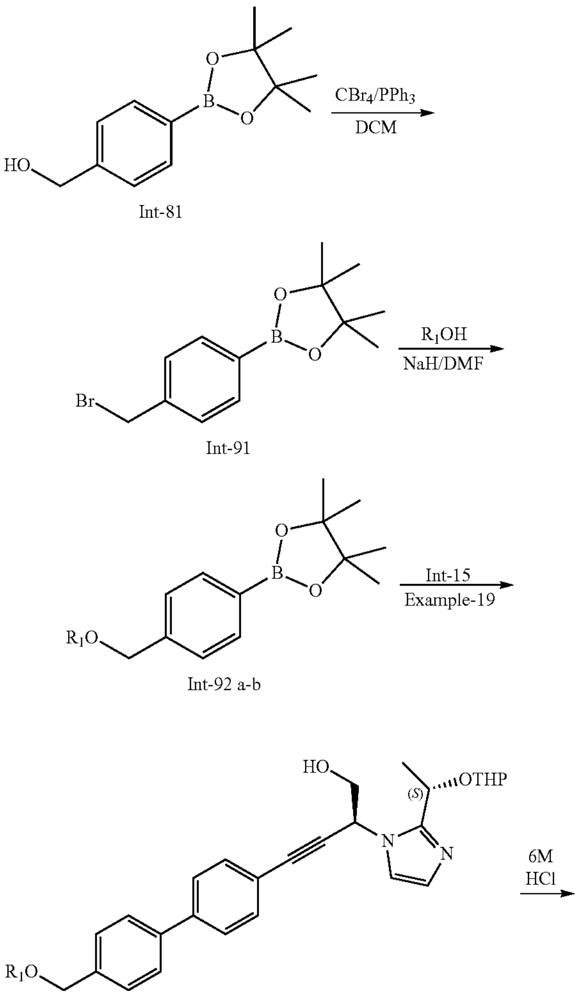

Int-81

Int-91

Int-92 a-b

Int-93a-b

-continued

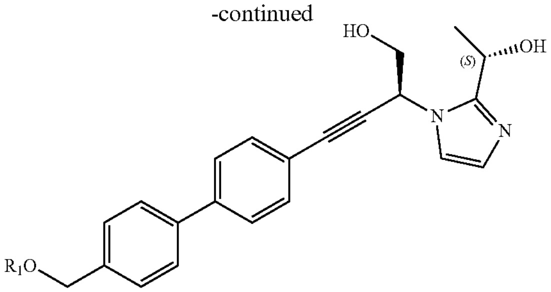

Certain compounds of Formula I

Step 1: To a stirred solution of Int-81 (3.0 g, 0.0128 mol) in DCM (25 mL), $PPh_3$ (3.5 g, 0.0134 mol) was added followed by the addition of $CBr_4$ (4.67 g, 0.0140 mol). The reaction mixture was stirred for a period of 6 h. After 6 h, the reaction mixture was concentrated and purified on silica gel column eluted with 1-8% EtOAc in hexanes to obtain the desired compound Int-91 in around 85% yield as a thick yellow oil. LC-MS: Calculated for $C_{13}H_{18}BBrO_2$ is 297.0, Observed: No ionization (not observed)

Step 2: To a stirred solution of the alcohol Int-29a (0.0064 mol) in dry THE (15 mL) and NaH (60% dispersion in mineral oil) (0.0097 mol) was added portion wise at 0° C. The reaction mixture was stirred at 0° C. for 30 minutes. Then (Int-91) (0.0084 mol) was dissolved in THE and slowly added to the reaction mixture, stirred at 0° C. for 30 minutes. Then reaction mixture was stirred at RT for 2 h. After the completion of the reaction, the reaction mixture was quenched with sat. $NH_4Cl$ solution, diluted with EtOAc (500 mL) and washed with ice cold water (200 mL), dried over anhydrous $Na_2SO_4$, filtered and concentrated under reduced pressure. The crude product Int-92a was taken directly taken to the next step without further Yield: 1.49 g (57.32%). LC-MS: Calculated for $C_{24}H_{38}BNO_6$ is 448.2, Observed: No ionization (not observed).

The same procedure was followed by starting with tert-butyl ((1R,2R)-2-hydroxycyclopropyl)carbamate to obtain Int-92b.

The following compounds were prepared according to Example 22 using similar procedures to those in Example 20 from appropriate Int 92 a-b and Int-15 to give the desired compounds as a white solid which yielded between 28-32%.

| Compound No. | Alcohol | Mass [M + H]+ |
|---|---|---|
| 6 | Int-29a | 436.5 |
| 9 | 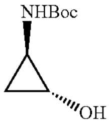 | 418.5 |

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example A-2: Oral Solution

To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

II. Biological Evaluation

Example B-1: In Vitro Assays to Screen Compounds and Metalloprotein Modulators Bacterial Susceptibility Testing Minimal inhibitory concentrations (MIC) were determined by the broth microdilution method in accordance with the Clinical and Laboratory Standards Institute (CLSI) guidelines. In brief, organism suspensions were adjusted to a final inoculum between $3\times10^5$ and $7\times10^5$ colony-forming units (CFU)/mL. Drug dilutions and inocula were made in sterile, cation adjusted Mueller-Hinton Broth (Beckton Dickinson). In wells, an inoculum volume of 100 μL was mixed to 2 μL of DMSO with 2-fold serial dilutions of drug. All inoculated microdilution trays were incubated in ambient air at 35° C. for 18-24 h. Following incubation, the lowest concentration of the drug that prevented visible growth (OD600 nm<0.05) was recorded as the MIC. Performance of the assay was monitored by the use of laboratory quality-control strains and compounds with defined MIC spectrum, in accordance with CLSI guidelines Exemplary in vitro assay data against select bacteria for compounds in embodiments of the disclosure is provided in Table A. Compounds of the disclosure do not inhibit *S. aureus*.

TABLE A

| Com- | MIC (μg/mL) | | | |
|---|---|---|---|---|
| pound No. | *E. coli* ATCC25922 | *K. pneumoniae* ATCC13883 | *P. aeruginosa* 209 PAO1 | *P. aeruginosa* ATCC27835 |
| 1 | 8 | 32 | 1 | 1 |
| 2 | 8 | 16 | 2 | 2 |
| 3 | 2 | 4 | 1 | 2 |
| 4 | 0.25 | 0.5 | 2 | 2 |
| 5 | 8 | 16 | 4 | 4 |
| 6 | 16 | 32 | 2 | 4 |
| 7 | 2 | 4 | 2 | 2 |
| 8 | — | 4 | 2 | 2 |
| 9 | — | 4 | 2 | 4 |
| 10 | — | 2 | 1 | 2 |
| 11 | — | 8 | 2 | 4 |
| 12 | — | 2 | 2 | 4 |
| 13 | — | 1 | 2 | 4 |
| 14 | — | 2 | 1 | 2 |
| 15 | — | 1 | 0.5 | 2 |
| 16 | — | 4 | 2 | 4 |
| 17 | — | 2 | 1 | 2 |
| 18 | — | 0.25 | 2 | 2 |
| 19 | — | 1 | 4 | 4 |
| 20 | — | 0.5 | 4 | 4 |
| 21 | — | 1 | 4 | 4 |
| 22 | — | 4 | 1 | 4 |
| 23 | — | 2 | 2 | 2 |
| 24 | — | 4 | 2 | 4 |
| 25 | — | 0.5 | 2 | 4 |
| 26 | — | 4 | 4 | 4 |
| 27 | — | 0.5 | 2 | 4 |
| 28 | — | 0.5 | 2 | 4 |
| 29 | — | 0.5 | 2 | 2 |
| 30 | — | 0.5 | 0.5 | 2 |
| 31 | — | 0.25 | 2 | 4 |
| 32 | — | 0.5 | 1 | 4 |
| 33 | — | 4 | 2 | 2 |
| 34 | 0.5 | 2 | 2 | 4 |
| 35 | 0.5 | 2 | 4 | 4 |
| 36 | 0.25 | 1 | 1 | 2 |
| 37 | 2 | 8 | 4 | 4 |
| 38 | 2 | 8 | 4 | 4 |
| 39 | 8 | 32 | 4 | 8 |
| 40 | 0.5 | 2 | 4 | 2 |
| 41 | 0.5 | 2 | 4 | 2 |
| 42 | 0.5 | 0.5 | 2 | 2 |
| 43 | 1 | 2 | 4 | 2 |
| 44 | 2 | 4 | 4 | 4 |
| 45 | 16 | 8 | 2 | 2 |
| 46 | 1 | 2 | 1 | 2 |

LpxC Binding Assay $IC_{50}$ values against *E. coli* and *P. aeruginosa* LpxC are determined using a Rapid Fire MS assay as previously described J. Med. Chem. 2012, 55, 1662-1670.

Exemplary in vitro assay data against select bacteria for compounds in embodiments of the disclosure is provided in Table B.

TABLE B

| Compound No. | *E. coli* LpxC $IC_{50}$ (nM) | *K. pneumoniae* LpxC $IC_{50}$ (nM) | *P. aeruginosa* LpxC $IC_{50}$ (nM) |
|---|---|---|---|
| 3 | 1.5 | 2.2 | 15.1 |
| 7 | 13.6 | — | 25.5 |
| 8 | 1.0 | 1.9 | 9.6 |
| 9 | 1.8 | 3.9 | 47.7 |
| 10 | <0.5 | 0.9 | 5.1 |
| 11 | 1.0 | 1.8 | 6.6 |
| 12 | <0.5 | 1.1 | 6.0 |
| 13 | <0.5 | 0.9 | 5.5 |
| 14 | <0.5 | 0.9 | 6.4 |

TABLE B-continued

| Compound No. | *E. coli* LpxC $IC_{50}$ (nM) | *K. pneumoniae* LpxC $IC_{50}$ (nM) | *P. aeruginosa* LpxC $IC_{50}$ (nM) |
|---|---|---|---|
| 15 | 1.0 | 1.6 | 9.8 |
| 16 | 1.3 | 2.2 | 8.3 |
| 17 | 0.5 | 1.0 | 6.6 |
| 18 | <0.5 | 0.6 | 8.6 |
| 19 | <0.5 | 0.7 | 15.9 |
| 20 | <0.5 | 0.7 | 11.8 |
| 21 | <0.5 | 0.7 | 12.6 |
| 22 | 0.8 | 1.5 | 8.0 |
| 23 | 0.5 | 1.0 | 7.8 |
| 24 | 1.9 | 4.1 | 42.9 |

The examples and embodiments described herein are for illustrative purposes only and various modifications or changes suggested to persons skilled in the art are to be included within the spirit and purview of this application and scope of the appended claims.

What is claimed is:

1. A compound of Formula (I):

Formula (I)

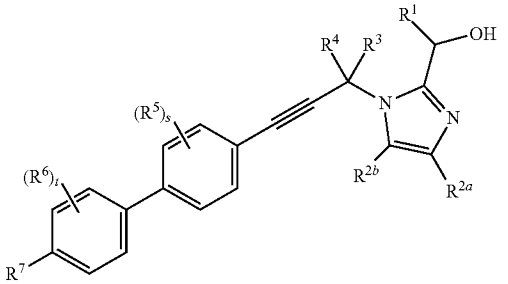

or a pharmaceutically acceptable salt, solvate, or prodrug thereof, wherein:

$R^1$ is $C_1$-$C_4$ alkyl;

$R^{2a}$ and $R^{2b}$ are each independently hydrogen, halogen, or $C_1$-$C_4$ alkyl;

$R^3$ is hydrogen, —($C_1$-$C_4$ alkylene)-OH, or —($C_1$-$C_4$ alkylene)-$NH_2$;

$R^4$ is hydrogen or $C_1$-$C_4$ alkyl;

each $R^5$ and $R^6$ is independently hydrogen, halogen, or $C_1$-$C_4$ alkyl;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O—($C_3$-$C_6$ cycloalkyl), —O-(4- to 6-membered heterocycloalkyl), —($C_1$-$C_4$ alkylene)-($C_3$-$C_6$ cycloalkyl), —($C_1$-$C_4$ alkylene)-(4- to 6-membered heterocycloalkyl), —O—($C_1$-$C_4$ alkylene)-($C_3$-$C_6$ cycloalkyl), —O—($C_1$-$C_4$ alkylene)-(4- to 6-membered heterocycloalkyl), —($C_1$-$C_4$ alkylene)-O—($C_3$-$C_6$ cycloalkyl), or —($C_1$-$C_4$ alkylene)-O-(4- to 6-membered heterocycloalkyl); wherein the alkyl, alkoxy, heteroalkyl, cycloalkyl, or heterocycloalkyl is unsubstituted or substituted by 1, 2, or 3 groups independently selected from —$OR^8$, —$N(R^8)_2$, —$CO_2R^8$, —$CON(R^8)_2$, —$CH_2N(R^8)_2$, —$NHCOR_8$, —$NHSO_2R^8$, —$CH_2CN$, $C_1$-$C_4$ alkyl, $C_1$-$C_4$ hydroxyalkyl, —C(═O)—$C_1$-$C_4$ hydroxyalkyl, $C_1$-$C_4$ methoxyalkyl, and $C_1$-$C_4$ aminoalkyl;

each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$NH_2$, —OMe, —$N(CH_3)_2$, —$CO_2H$, —$CONH_2$, —$SO_2CH_3$, —C(═NH) $NH_2$, phenyl, and monocyclic heteroaryl which is unsubstituted or substituted by 1 or 2 groups selected from —F, —CN, —OH, —$NH_2$, —OMe, —$N(CH_3)_2$, —$CO_2H$, —$CONH_2$, and —$SO_2CH_3$;

or two $R^8$ attached to the same nitrogen are taken together to form a 4- to 6-membered heterocycloalkyl which is unsubstituted or substituted by 1, 2, or 3 groups independently selected from —F, —CN, —OH, —$NH_2$, —OMe, —$CO_2H$, —$CONH_2$, and —$SO_2CH_3$;

s is 1 or 2; and t is 1 or 2.

2. The compound of claim 1, or a pharmaceutically acceptable salt, or solvate thereof, wherein:

$R^1$ is —$CH_3$;

$R^{2a}$ is hydrogen;

$R^{2b}$ is hydrogen; and $R^4$ is hydrogen.

3. The compound of claim 1, or a pharmaceutically acceptable salt, or solvate thereof, wherein:

each $R^5$ is independently hydrogen, fluoro, chloro, or —$CH_3$; and s is 1.

4. The compound of claim 1, or a pharmaceutically acceptable salt, or solvate thereof, wherein:

each $R^6$ is independently hydrogen, fluoro, chloro, or —$CH_3$; and tis 1.

5. The compound of claim 1, or a pharmaceutically acceptable salt, or solvate thereof, having the structure of Formula (IIa):

Formula (IIa)

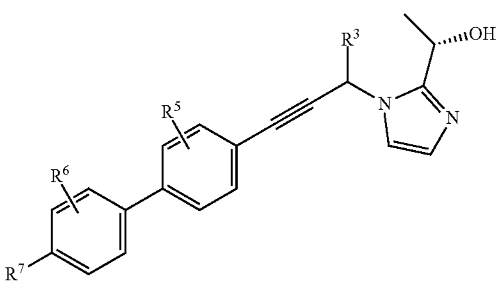

or a pharmaceutically acceptable salt, or solvate thereof, wherein:

$R^5$ is hydrogen or fluoro; and $R^6$ is hydrogen or fluoro.

6. The compound of claim 1, or a pharmaceutically acceptable salt, or solvate thereof, having the structure of Formula (IIIa):

Formula (IIIa)

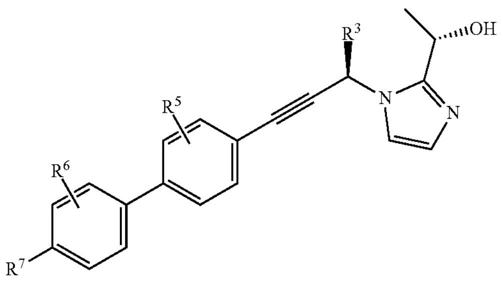

or a pharmaceutically acceptable salt, or solvate thereof, wherein;

$R^5$ is hydrogen or fluoro;

$R^6$ is hydrogen or fluoro; and $R^3$ is hydrogen or —($C_1$-$C_4$ alkylene)-OH.

7. The compound of claim 6, or a pharmaceutically acceptable salt, or solvate thereof, wherein:

$R^3$ is —$CH_2OH$.

8. The compound of claim 1, or a pharmaceutically acceptable salt, or solvate thereof, wherein:

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —NH-$SOR_8$, —$CH_2CN$, $C_1$-$C_4$ alkyl, —C(═O)—$C_1$-$C_4$ hydroxyalkyl, $C_1$-$C_4$ methoxyalkyl, and $C_1$-$C_4$ hydroxyalkyl;

each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH) $NH_2$, and monocyclic heteroaryl which is unsubstituted or substituted by 1-$CONH_2$ group.

9. The compound of claim 1, or a pharmaceutically acceptable salt, or solvate thereof, wherein:

$R^7$ is $C_1$-$C_6$ alkyl, $C_1$-$C_6$ alkoxy, $C_1$-$C_6$ heteroalkyl, $C_3$-$C_4$ cycloalkyl, 4- to 6-membered heterocycloalkyl, —O—($C_3$-$C_4$ cycloalkyl), —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ hydroxyalkyl, and $C_1$-$C_4$ methoxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl is unsubstituted or substituted by 1, 2, or 3 groups independently selected from —F, —CN, —OH, —$CO_2H$, —C(═NH) $NH_2$, and 5-membered monocyclic heteroaryl which is unsubstituted or substituted by 1-$CONH_2$ group.

10. The compound of claim 1, or a pharmaceutically acceptable salt, or solvate thereof, wherein;

$R^7$ is $C_1$-$C_5$ alkoxy, $C_3$-$C_4$ cycloalkyl, —O—($C_3$-$C_4$ cycloalkyl), or —O-(4- to 6-membered heterocycloalkyl); wherein the alkoxy, cycloalkyl, or heterocycloalkyl is substituted by 1 or 2 groups independently selected from —OH, —OMe, —$N(R^8)_2$, —$NHSO_2R^8$, and —$CH_2CN$; and each $R^8$ is independently hydrogen, $C_1$-$C_2$ alkyl, or —C(═O)—$C_1$-$C_2$ alkyl, wherein the alkyl is unsubstituted or substituted by 1 or 2 groups independently selected from —CN, —OH, and oxadiazolyl.

11. The compound of claim 1, or a pharmaceutically acceptable salt, or solvate thereof, wherein:

$R^7$ is —O—($C_3$-$C_4$ cycloalkyl); wherein the cycloalkyl is substituted by 1 or 2 groups independently selected from —OH, —$OCH_3$, —$NH_2$, and —$N(CH_3)_2$.

12. The compound of claim 1, or a pharmaceutically acceptable salt, or solvate thereof, wherein:

$R^7$ is —O-(4- to 6-membered heterocycloalkyl); wherein the heterocycloalkyl is substituted by 1 or 2 groups independently selected from —OH, —$OCH_3$, —$NH_2$, —$N(CH_3)_2$, —$CH_2CN$, —$CH_3$, and —$CH_2CH_2OCH_3$.

13. The compound of claim 1, or a pharmaceutically acceptable salt, or solvate thereof, wherein:

$R^7$ is

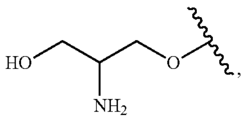, 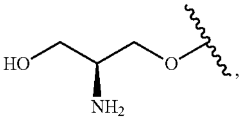,

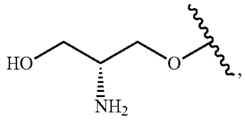, 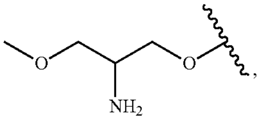,

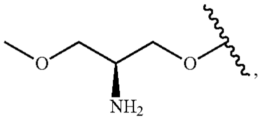, 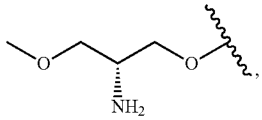,

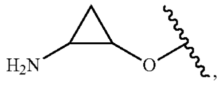, 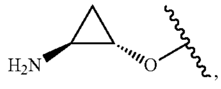,

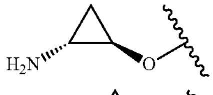, 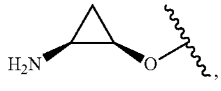,

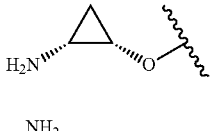, 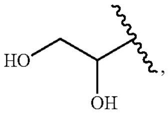,

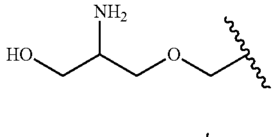, 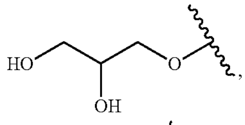,

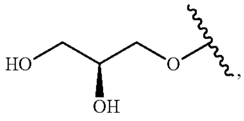, 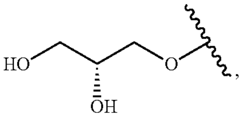,

-continued
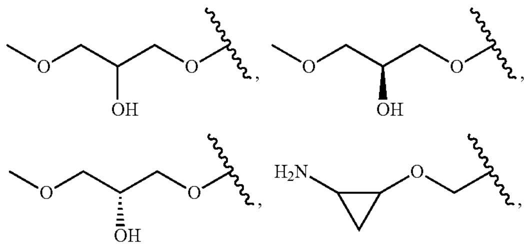
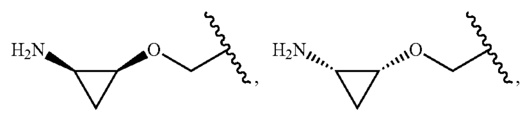
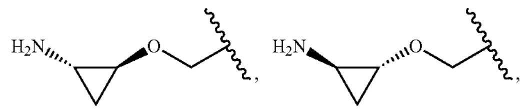
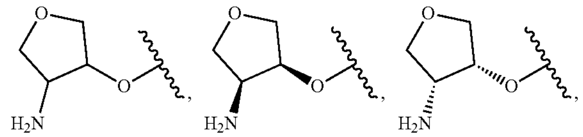
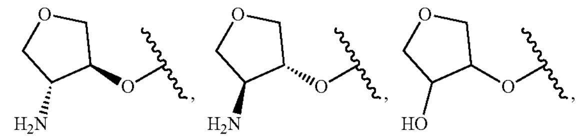
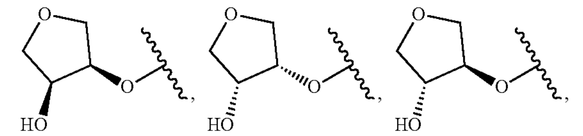
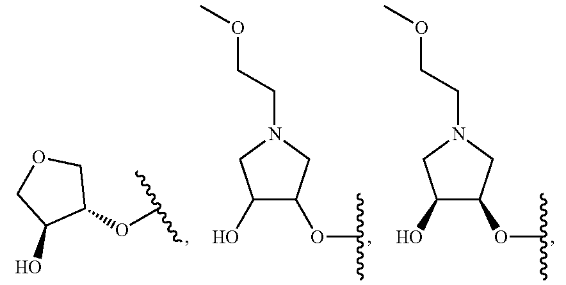
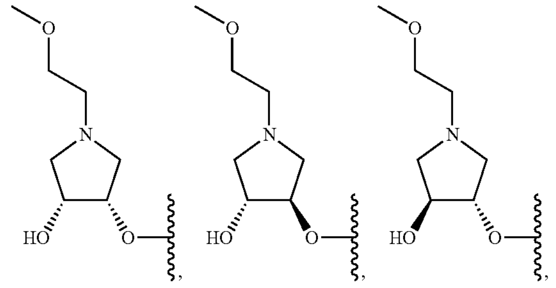
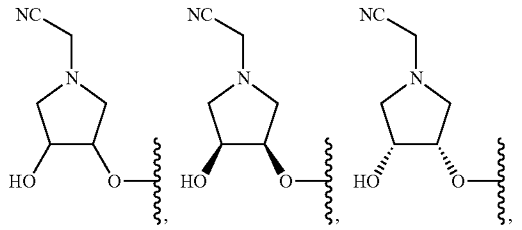
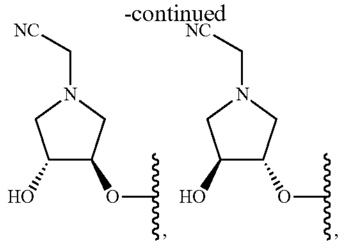
-continued
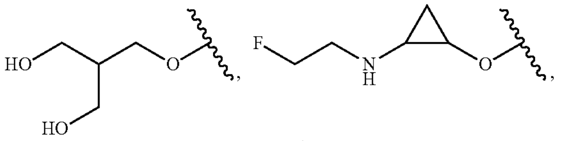
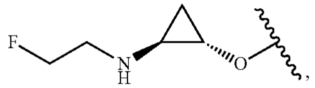
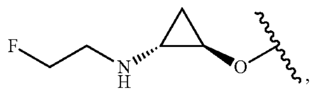
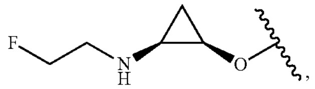
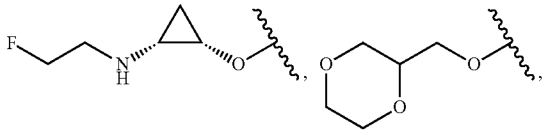
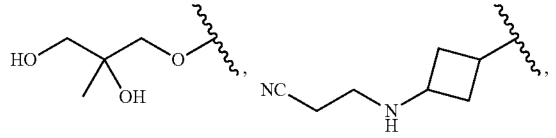
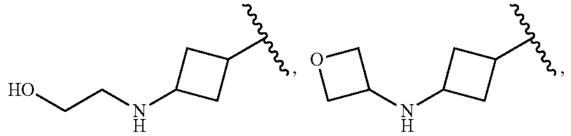
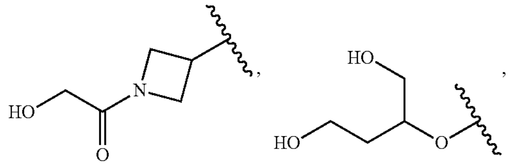
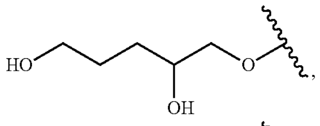
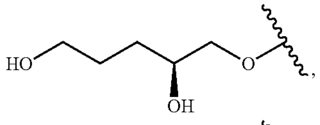
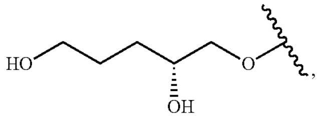
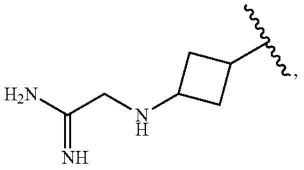

-continued

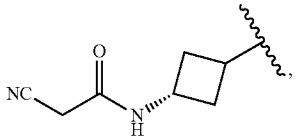

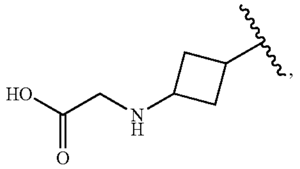

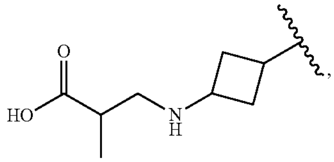

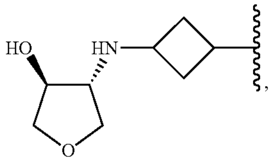

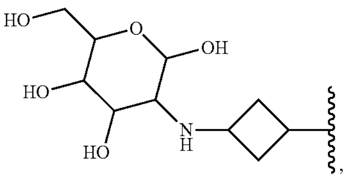

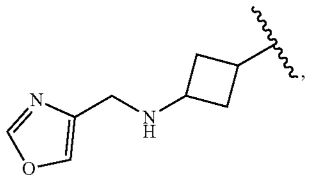

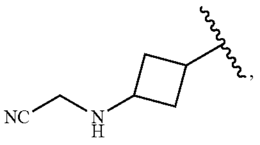

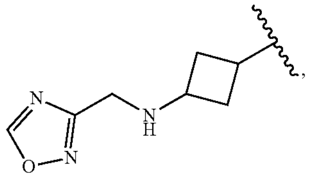

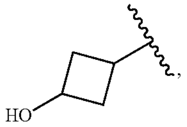

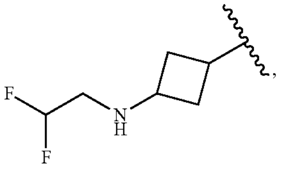

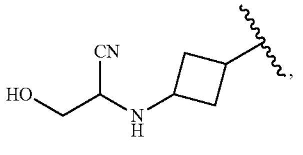

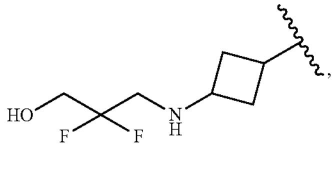

-continued

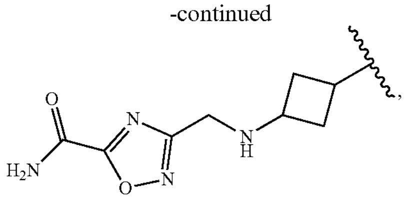

or

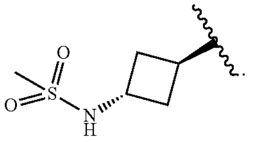

14. The compound of claim 1, or a pharmaceutically acceptable salt, or solvate thereof, wherein:

$R^1$ is —$CH_3$;

$R^{2a}$ and $R^{2b}$ are each hydrogen;

$R^3$ is hydrogen, —($C_1$-$C_4$ alkylene)-OH, or —($C_1$-$C_4$ alkylene)-$NH_2$;

$R^4$ is hydrogen;

each $R^5$ and $R^6$ is hydrogen;

$R^7$ is $C_1$-$C_6$ alkyl, $C_1$-$C_6$ alkoxy, $C_1$-$C_6$ heteroalkyl, $C_3$-$C_6$ cycloalkyl, 4- to 6-membered heterocycloalkyl, —O-(4- to 6-membered heterocycloalkyl), —O—($C_1$-$C_4$ alkylene)-(4- to 6-membered heterocycloalkyl), or —($C_1$-$C_4$ alkylene)-O—($C_3$-$C_6$ cycloalkyl); wherein the alkyl, alkoxy, heteroalkyl, cycloalkyl, or heterocycloalkyl is unsubstituted or substituted by 1 or 2 groups independently selected from —$OR^8$, —$N(R^8)_2$, —$NHSO_2R^8$, —$CH_2CN$, $C_1$-$C_4$ alkyl, —C(═O)—$C_1$-$C_4$ hydroxyalkyl, $C_1$-$C_4$ methoxyalkyl, and $C_1$-$C_4$ hydroxyalkyl; and each $R^8$ is independently hydrogen, $C_1$-$C_4$ alkyl, —C(═O)—$C_1$-$C_4$ alkyl, or 4- to 6-membered heterocycloalkyl, wherein the alkyl or heterocycloalkyl is unsubstituted or substituted by 1, 2, 3, or 4 groups independently selected from —F, —CN, —OH, —$CH_2OH$, —$CO_2H$, —C(═NH) $NH_2$, and monocyclic heteroaryl which is unsubstituted or substituted by 1-$CONH_2$ group.

15. The compound of claim 1, selected from:

1: (2R)-4-(4'-(2-amino-3-hydroxypropoxy)-[1,1'-biphenyl]-4-yl)-2-(2-((R)-1-hydroxyethyl)-1H-imidazol-1-yl) but-3-yn-1-ol;

2: (R)-4-(4'-((S)-2-amino-3-hydroxypropoxy)-[1,1'-biphenyl]-4-yl)-2-(2-((S)-1-hydroxyethyl)-1H-imidazol-1-yl) but-3-yn-1-ol;

3: (2S)-4-(4'-(2-amino-3-methoxypropoxy)-[1,1'-biphenyl]-4-yl)-2-(2-((S)-1-hydroxyethyl)-1H-imidazol-1-yl) but-3-yn-1-ol;

4: (S)-4-(4'-((trans)-2-aminocyclopropoxy)-[1,1'-biphenyl]-4-yl)-2-(2-((S)-1-hydroxyethyl)-1H-imidazol-1-yl) but-3-yn-1-ol;

5:1-(4'-((S)-4-hydroxy-3-(2-((S)-1-hydroxyethyl)-1H-imidazol-1-yl) but-1-yn-1-yl)-[1,1'-biphenyl]-4-yl) ethane-1,2-diol;

6: (2S)-4-(4'-((2-amino-3-hydroxypropoxy)methyl)-[1,1'-biphenyl]-4-yl)-2-(2-((S)-1-hydroxyethyl)-1H-imidazol-1-yl) but-3-yn-1-ol;

7: 2-amino-3-((4'-(3-(2-((S)-1-hydroxyethyl)-1H-imidazol-1-yl) prop-1-yn-1-yl)-[1,1'-biphenyl]-4-yl)oxy) propan-1-ol;

8: (S)-3-((4'-((S)-4-hydroxy-3-(2-((S)-1-hydroxyethyl)-1H-imidazol-1-yl) but-1-yn-1-yl)-[1,1'-biphenyl]-4-yl) oxy) propane-1,2-diol;

9: (S)-4-(4'-(((trans)-2-aminocyclopropoxy)methyl)-[1,1'-biphenyl]-4-yl)-2-(2-((S)-1-hydroxyethyl)-1H-imidazol-1-yl) but-3-yn-1-ol;

10: (trans)-4-((4'-((S)-4-hydroxy-3-(2-((S)-1-hydroxyethyl)-1H-imidazol-1-yl) but-1-yn-1-yl)-[1,1'-biphenyl]-4-yl)oxy) tetrahydrofuran-3-ol;

11: 2-(((4'-((S)-4-hydroxy-3-(2-((S)-1-hydroxyethyl)-1H-imidazol-1-yl) but-1-yn-1-yl)-[1,1'-biphenyl]-4-yl) oxy) methyl) propane-1,3-diol;

12: (S)-4-(4'-((trans)-2-((2-fluoroethyl)amino) cyclopropoxy)-[1,1'-biphenyl]-4-yl)-2-(2-((S)-1-hydroxyethyl)-1H-imidazol-1-yl) but-3-yn-1-ol;

13: (2S)-4-(4'-((1,4-dioxan-2-yl) methoxy)-[1,1'-biphenyl]-4-yl)-2-(2-((S)-1-hydroxyethyl)-1H-imidazol-1-yl) but-3-yn-1-ol;

14: (S)-4-(4'-((R)-2-hydroxy-3-methoxypropoxy)-[1,1'-biphenyl]-4-yl)-2-(2-((S)-1-hydroxyethyl)-1H-imidazol-1-yl) but-3-yn-1-ol;

15: (S)-4-(4'-(((trans)-4-aminotetrahydrofuran-3-yl)oxy)-[1,1'-biphenyl]-4-yl)-2-(2-((S)-1-hydroxyethyl)-1H-imidazol-1-yl) but-3-yn-1-ol;

16: 3-((4'-((S)-4-hydroxy-3-(2-((S)-1-hydroxyethyl)-1H-imidazol-1-yl) but-1-yn-1-yl)-[1,1'-biphenyl]-4-yl) oxy)-2-methylpropane-1,2-diol;

17: 4-((4'-((S)-4-hydroxy-3-(2-((S)-1-hydroxyethyl)-1H-imidazol-1-yl) but-1-yn-1-yl)-[1,1'-biphenyl]-4-yl) oxy) butane-1,2-diol;

18: (S)-3-((3-(4'-(3-(2-(1-hydroxyethyl)-1H-imidazol-1-yl) prop-1-yn-1-yl)-[1,1'-biphenyl]-4-yl)cyclobutyl) amino) propanenitrile;

19: (S)-2-((3-(4'-(3-(2-(1-hydroxyethyl)-1H-imidazol-1-yl) prop-1-yn-1-yl)-[1,1'-biphenyl]-4-yl)cyclobutyl) amino) ethan-1-ol;

20: (S)-1-(1-(3-(4'-(3-(oxetan-3-ylamino)cyclobutyl)-[1,1'-biphenyl]-4-yl) prop-2-yn-1-yl)-1H-imidazol-2-yl) ethan-1-ol;

21: (S)-2-hydroxy-1-(3-(4'-(3-(2-(1-hydroxyethyl)-1H-imidazol-1-yl) prop-1-yn-1-yl)-[1,1'-biphenyl]-4-yl) azetidin-1-yl) ethan-1-one;

22: 2-((4'-((S)-4-hydroxy-3-(2-((S)-1-hydroxyethyl)-1H-imidazol-1-yl) but-1-yn-1-yl)-[1,1'-biphenyl]-4-yl) oxy) butane-1,4-diol;

23: 5-((4'-((S)-4-hydroxy-3-(2-((S)-1-hydroxyethyl)-1H-imidazol-1-yl) but-1-yn-1-yl)-[1,1'-biphenyl]-4-yl) oxy) pentane-1,4-diol;

24: (trans)-4-((4'-((S)-4-amino-3-(2-((S)-1-hydroxyethyl)-1H-imidazol-1-yl) but-1-yn-1-yl)-[1,1'-biphenyl]-4-yl)oxy) tetrahydrofuran-3-ol;

25: (S)-2-((3-(4'-(3-(2-(1-hydroxyethyl)-1H-imidazol-1-yl) prop-1-yn-1-yl)-[1,1'-biphenyl]-4-yl)cyclobutyl) amino) acetimidamide;

26: (S)-(3-(4'-(3-(2-(1-hydroxyethyl)-1H-imidazol-1-yl) prop-1-yn-1-yl)-[1,1'-biphenyl]-4-yl)cyclobutyl) glycine;

27: (S)-1-(1-(3-(4'-(3-((oxazol-4-ylmethyl)amino)cyclobutyl)-[1,1'-biphenyl]-4-yl) prop-2-yn-1-yl)-1H-imidazol-2-yl) ethan-1-ol;

28: 2-((3-(4'-((S)-4-hydroxy-3-(2-((S)-1-hydroxyethyl)-1H-imidazol-1-yl) but-1-yn-1-yl)-[1,1'-biphenyl]-4-yl) cyclobutyl) amino) acetonitrile;

29: (S)-4-(4'-(3-(((1,2,4-oxadiazol-3-yl)methyl) amino) cyclobutyl)-[1,1'-biphenyl]-4-yl)-2-(2-((S)-1-hydroxyethyl)-1H-imidazol-1-yl) but-3-yn-1-ol;

30: 3-(4'-((S)-4-hydroxy-3-(2-((S)-1-hydroxyethyl)-1H-imidazol-1-yl) but-1-yn-1-yl)-[1,1'-biphenyl]-4-yl)cyclobutan-1-ol;

31: (S)-4-(4'-(3-((2,2-difluoroethyl)amino) cyclobutyl)-[1,1'-biphenyl]-4-yl)-2-(2-((S)-1-hydroxyethyl)-1H-imidazol-1-yl) but-3-yn-1-ol;

32: 3-((3-(4'-((S)-4-hydroxy-3-(2-((S)-1-hydroxyethyl)-1H-imidazol-1-yl) but-1-yn-1-yl)-[1,1'-biphenyl]-4-yl) cyclobutyl) amino) propanenitrile;

33: 3-hydroxy-2-((3-(4'-((S)-4-hydroxy-3-(2-((S)-1-hydroxyethyl)-1H-imidazol-1-yl) but-1-yn-1-yl)-[1,1'-biphenyl]-4-yl)cyclobutyl) amino) propanenitrile;

34: (S)-4-(4'-(3-((2,2-difluoro-3-hydroxypropyl)amino) cyclobutyl)-[1,1'-biphenyl]-4-yl)-2-(2-((S)-1-hydroxyethyl)-1H-imidazol-1-yl) but-3-yn-1-ol;

35: 3-(((3-(4'-((S)-4-hydroxy-3-(2-((S)-1-hydroxyethyl)-1H-imidazol-1-yl) but-1-yn-1-yl)-[1,1'-biphenyl]-4-yl) cyclobutyl) amino)methyl)-1,2,4-oxadiazole-5-carboxamide; and 36: N-((1S,3r)-3-(4'-((S)-4-hydroxy-3-(2-((S)-1-hydroxyethyl)-1H-imidazol-1-yl) but-1-yn-1-yl)-[1,1'-biphenyl]-4-yl)cyclobutyl) methanesulfonamide;

37: 3-((3-(4'-((S)-4-hydroxy-3-(2-((S)-1-hydroxyethyl)-1H-imidazol-1-yl) but-1-yn-1-yl)-[1,1'-biphenyl]-4-yl) cyclobutyl) amino)-2-methylpropanoic acid;

38: (3R,4S)-4-((3-(4'-((S)-4-hydroxy-3-(2-((S)-1-hydroxyethyl)-1H-imidazol-1-yl) but-1-yn-1-yl)-[1,1'-biphenyl]-4-yl)cyclobutyl) amino)tetrahydrofuran-3-ol;

39: 3-((3-(4'-((S)-4-hydroxy-3-(2-((S)-1-hydroxyethyl)-1H-imidazol-1-yl) but-1-yn-1-yl)-[1,1'-biphenyl]-4-yl) cyclobutyl) amino)-6-(hydroxymethyl)tetrahydro-2H-pyran-2,4,5-triol;

40: 2-cyano-N-(3-(4'-((S)-4-hydroxy-3-(2-((S)-1-hydroxyethyl)-1H-imidazol-1-yl) but-1-yn-1-yl)-[1,1'-biphenyl]-4-yl)cyclobutyl) acetamide;

41: (3S,4R)-4-((4'-((S)-4-hydroxy-3-(2-((S)-1-hydroxyethyl)-1H-imidazol-1-yl) but-1-yn-1-yl)-[1,1'-biphenyl]-4-yl)methyl) tetrahydrofuran-3-ol;

42: (3R,4R)-4-((4'-(3-(2-((S)-1-hydroxyethyl)-1H-imidazol-1-yl) prop-1-yn-1-yl)-[1,1'-biphenyl]-4-yl)oxy) tetrahydrofuran-3-ol;

43: (3R,4R)-4-((4'-((R)-5-hydroxy-3-(2-((S)-1-hydroxyethyl)-1H-imidazol-1-yl) pent-1-yn-1-yl)-[1,1'-biphenyl]-4-yl)oxy) tetrahydrofuran-3-ol;

44: (3R,4R)-4-((4'-((S)-4-hydroxy-3-(2-((S)-1-hydroxyethyl)-1H-imidazol-1-yl) but-1-yn-1-yl)-[1,1'-biphenyl]-4-yl)oxy)-1-(2-methoxyethyl) pyrrolidin-3-ol;

45: 2-((3R,4R)-3-hydroxy-4-((4'-((S)-4-hydroxy-3-(2-((S)-1-hydroxyethyl)-1H-imidazol-1-yl) but-1-yn-1-yl)-[1,1'-biphenyl]-4-yl)oxy) pyrrolidin-1-yl) acetonitrile;

46: (cis)-4-((4'-((S)-4-hydroxy-3-(2-((S)-1-hydroxyethyl)-1H-imidazol-1-yl) but-1-yn-1-yl)-[1,1'-biphenyl]-4-yl)oxy) tetrahydrofuran-3-ol;

or a pharmaceutically acceptable salt, or solvate thereof.

16. A pharmaceutical composition comprising the compound of claim 1, or a pharmaceutically acceptable salt, or solvate thereof, and a pharmaceutically acceptable excipient.

17. A method of treating a gram-negative bacterial infection in a patient in need thereof comprising administering a therapeutically effective amount to the patient the compound of claim 1, or a pharmaceutically acceptable salt, or solvate thereof, or the pharmaceutical composition of claim 16.

18. The method of claim 17, wherein the gram-negative bacterial infection is associated with *Pseudomonas aeruginosa* or is a respiratory infection.

19. A method of treating a *P. aeruginosa* infection in a patient in need thereof comprising administering a therapeutically effective amount to the patient the compound of claim 1, or a pharmaceutically acceptable salt, or solvate thereof, or the pharmaceutical composition of claim 16.

20. The method of claim 19, wherein the patient has been identified as having a lung disease, wherein the lung disease is cystic fibrosis, bronchiectasis, emphysema, chronic obstructive pulmonary disease (COPD), chronic destroyed lung disease, or a combination thereof.

* * * * *